(12) United States Patent
Bachelet et al.

(10) Patent No.: US 10,420,842 B2
(45) Date of Patent: *Sep. 24, 2019

(54) NON-IMMUNOGENIC AND NUCLEASE RESISTANT NUCLEIC ACID ORIGAMI DEVICES AND COMPOSITIONS THEREOF

(71) Applicant: BAR-ILAN UNIVERSITY, Ramat Gan (IL)

(72) Inventors: Ido Bachelet, Modiin (IL); Almogit Abu-Horowitz, Hertzeliya (IL); Eldad Ben-Ishay, Shoham (IL); Yaniv Amir, Yehud (IL); Ariel Munitz, Jerusalem (IL); Anastasia Shapiro, Rishon Lezion (IL); Amir Shemer, Petach Tikva (IL); Zeev Zalevsky, Rosh HaAyin (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 689 days.

This patent is subject to a terminal disclaimer.

(21) Appl. No.: 14/785,185

(22) PCT Filed: Apr. 13, 2014

(86) PCT No.: PCT/IL2014/050356
§ 371 (c)(1),
(2) Date: Oct. 16, 2015

(87) PCT Pub. No.: WO2014/170898
PCT Pub. Date: Oct. 23, 2014

(65) Prior Publication Data
US 2016/0082122 A1    Mar. 24, 2016

Related U.S. Application Data

(60) Provisional application No. 61/813,412, filed on Apr. 18, 2013.

(51) Int. Cl.
*C12N 15/115* (2010.01)
*A61K 47/48* (2006.01)
(Continued)

(52) U.S. Cl.
CPC ........ *A61K 47/48776* (2013.01); *A61K 38/28* (2013.01); *A61K 47/549* (2017.08);
(Continued)

(58) Field of Classification Search
None
See application file for complete search history.

(56) References Cited

U.S. PATENT DOCUMENTS

2007/0011710 A1    1/2007  Chiu
2007/0117109 A1*   5/2007  Rothemund ............ C12P 19/34
                                                        435/6.12

FOREIGN PATENT DOCUMENTS

WO    WO2004011680 A1    2/2004
WO    WO2012061719 A3    5/2012

OTHER PUBLICATIONS

Zadegan et al; "Construction of a 4 Zeptoliters Switchable 3D DNA Box Origami" ACS Nano, 6 (11), pp. 10050-10053. (2012).
(Continued)

*Primary Examiner* — Robert T. Crow
(74) *Attorney, Agent, or Firm* — Symbus Law Group, LLC; Clifford D. Hyra

(57) ABSTRACT

Nucleic acid origami devices are provided that are non-immunogenic and/or resistant to nucleases, which may be activated by one or more external cues, such as ligands, glucose concentration or electromagnetic fields; or used for attenuation or prevention of internalization of cell-surface receptors or prolongation of shelf-life of active agents.
(Continued)

Further provided are methods for treating diabetes and methods for preparing the devices.

19 Claims, 17 Drawing Sheets

Specification includes a Sequence Listing.

(51) Int. Cl.
    *C12Q 1/68*     (2018.01)
    *A61K 38/28*     (2006.01)
    *A61K 47/54*     (2017.01)
    *A61K 47/69*     (2017.01)
    *B82Y 5/00*     (2011.01)

(52) U.S. Cl.
    CPC ...... *A61K 47/6901* (2017.08); *A61K 47/6923* (2017.08); *C12N 15/115* (2013.01); *C12Q 1/68* (2013.01); *B82Y 5/00* (2013.01); *C12N 2310/16* (2013.01); *C12N 2310/351* (2013.01); *C12N 2310/3519* (2013.01); *C12N 2310/3521* (2013.01); *C12N 2310/51* (2013.01); *C12N 2320/51* (2013.01); *C12N 2320/53* (2013.01); *C12N 2730/10151* (2013.01)

(56) References Cited

OTHER PUBLICATIONS

International Search report and Written Opinion as issued in PCT/IL2014/050356 dated Aug. 4, 2014.

\* cited by examiner

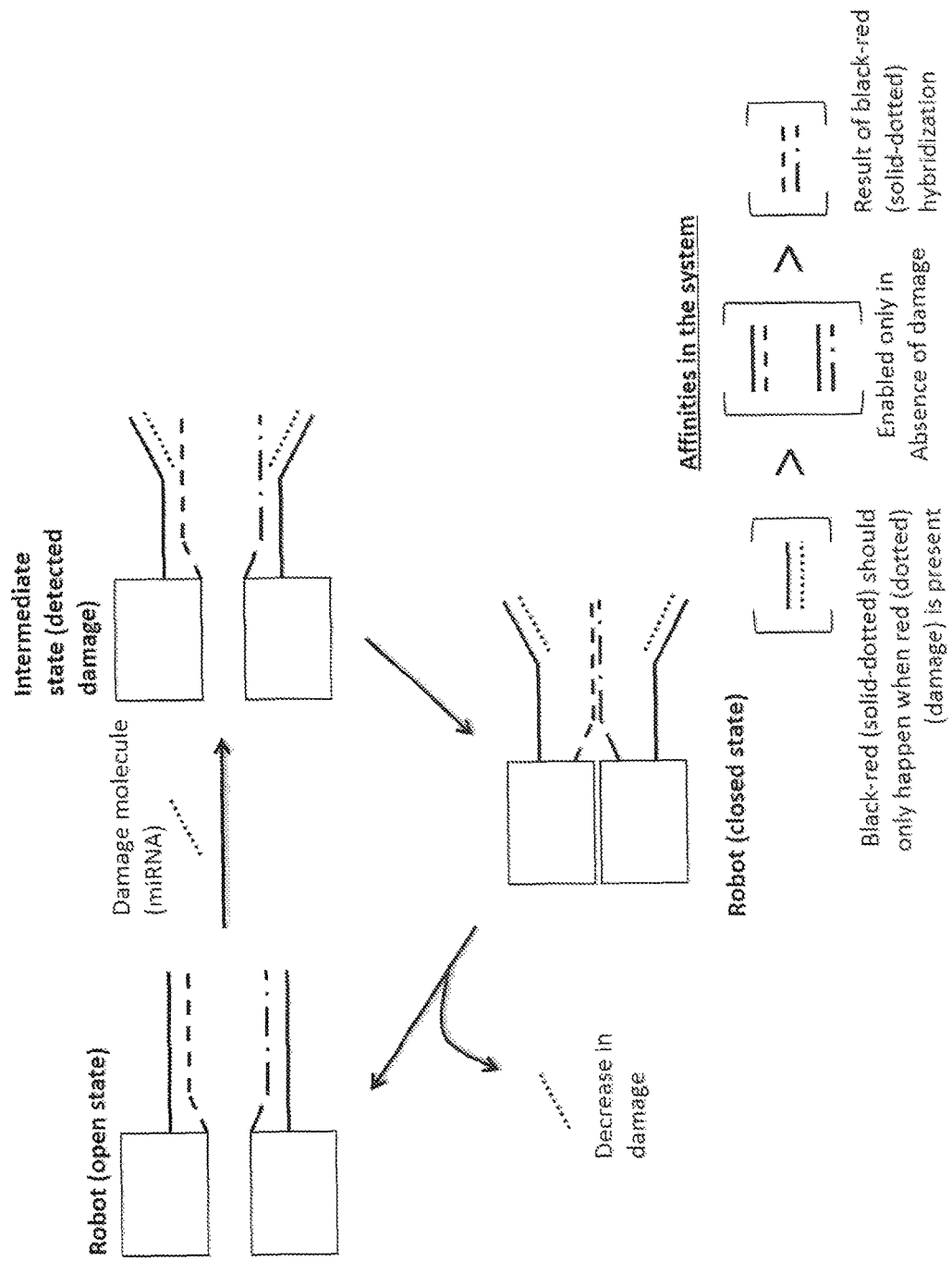

SEQUENCE LISTING

<160> NUMBER OF SEQ ID NOS: 284

<210> SEQ ID NO 1
<211> LENGTH: 7249
<212> TYPE: DNA
<213> ORGANISM: Artificial Sequence
<220> FEATURE:
<223> OTHER INFORMATION: Synthetic

<400> SEQUENCE: 1

```
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtacttta     180
gttgcatatt taaaacatgt tgagctacag cattatattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tcttttgat gcaatccgct ttgcttctga ctataatagt      420
cagggtaaag acctgatttt tgatttatgg tcattctcgt tttctgaact gtttaaagca     480
```

```
tttgaggggg attcaatgaa tatttatgac gattccgcag tattggacgc tatccagtct      540
aaacatttta ctattacccc ctctggcaaa acttcttttg caaaagcctc tcgctatttt      600 ggttttatc gtcgtctggt aaacgagggt tatgatagtg ttgctcttac tatgcctcgt      660 aattccttt ggcgttatgt atctgcatta gttgaatgtg gtattcctaa atctcaactg      720
atgaatcttt ctacctgtaa taatgttgtt ccgttagttc gttttattaa cgtagatttt      780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg gagcaggtcg cggatttcga cacaatttat     1140
caggcgatga tacaaatctc cgttgtactt tgtttcgcgc ttggtataat cgctgggggt     1200
caaagatgag tgttttagtg tattcttttg cctctttcgt tttaggttgg tgccttcgta     1260
gtggcattac gtattttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactcccT gcaagcctca gcgaccgaat atatcggtta     1440
tgcgtgggcg atggttgttg tcattgtcgg cgcaactatc ggtatcaagc tgtttaagaa     1500
attcacctcg aaagcaagct gataaaccga taatttaaa ggctcctttt ggagcctttt     1560
ttttggagat tttcaacgtg aaaaaattat tattcgcaat tcctttagtt gttcctttct     1620
attctcactc cgctgaaact gttgaaagtt gtttagcaaa atcccataca gaaaattcat     1680
ttactaacgt ctggaaagac gacaaaactt tagatcgtta cgctaactat gagggctgtc     1740
tgtggaatgc tacaggcgtt gtagtttgta ctggtgacga aactcagtgt tacggtacat     1800
gggttcctat tgggcttgct atccctgaaa atgagggtgg tggctctgag ggtggcggtt     1860
ctgagggtgg cggttctgag ggtggcggta ctaaacctcc tgagtacggt gatacaccta     1920
ttccgggcta cttatatatc aaccctctcg acggcactta tccgcctggt actgagcaaa     1980
accccgctaa tcctaatcct tctcttgagg agtctcagcc tcttaatact ttcatgtttc     2040
agaataatag gttccgaaat aggcaggggg cattaactgt ttatacgggc actgttactc     2100
aaggcactga ccccgttaaa acttattacc agtacactcc tgtatcatca aaagccatgt     2160
atgacgctta ctggaacggt aaattcagag actgcgcttt ccattctggc tttaatgagg     2220
atttatttgt ttgtgaatat caaggccaat cgtctgacct gcctcaacct cctgtcaatg     2280
ctggcggcgg ctctggtggt ggttctggtg gcggctctga gggtggtggc tctgagggtg     2340
gcggttctga gggtggcggc tctgagggag gcggttccgg tggtggctct ggttccggtg     2400
attttgatta tgaaaagatg gcaaacgcta ataaggggc tatgaccgaa aatgccgatg     2460
aaaacgcgct acagtctgac gctaaaggca aacttgattc tgtcgctact gattacggtg     2520
ctgctatcga tggtttcatt ggtgacgttt ccggccttgc taatggtaat ggtgctactg     2580
gtgattttgc tggctctaat tcccaaatgg ctcaagtcgg tgacggtgat aattcacctt     2640
taatgaataa tttccgtcaa tatttacctt ccctccctca atcggttgaa tgtcgccctt     2700
ttgtctttgg cgctggtaaa ccatatgaat tttctattga ttgtgacaaa ataaacttat     2760
tccgtggtgt ctttgcgttt cttttatatg ttgccacctt tatgtatgta ttttctacgt     2820
ttgctaacat actgcgtaat aaggagtctt aatcatgcca gttcttttgg gtattccgtt     2880
```

```
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcattttga cgttaaacaa aaaatcgttt cttatttgga    3180
ttgggataaa taatatggct gtttattttg taactggcaa attaggctct ggaaagacgc   3240
tcgttagcgt tggtaagatt caggataaaa ttgtagctgg gtgcaaaata gcaactaatc   3300
ttgatttaag gcttcaaaac ctcccgcaag tcgggaggtt cgctaaaacg cctcgcgttc   3360
ttagaatacc ggataagcct tctatatctg atttgcttgc tattgggcgc ggtaatgatt   3420
cctacgatga aaataaaaac ggcttgcttg ttctcgatga gtgcggtact tggtttaata   3480
cccgttcttg gaatgataag gaaagacagc cgattattga ttggtttcta catgctcgta   3540
aattaggatg ggatattatt tttcttgttc aggacttatc tattgttgat aaacaggcgc   3600
gttctgcatt agctgaacat gttgtttatt gtcgtcgtct ggacagaatt actttacctt   3660
ttgtcggtac tttatattct cttattactg gctcgaaaat gcctctgcct aaattacatg   3720
ttggcgttgt aaatatggc gattctcaat taagccctac tgttgagcgt tggctttata   3780
ctggtaagaa tttgtataac gcatatgata ctaaacaggc ttttttctagt aattatgatt   3840 ccggtgttta ttcttattta acgccttatt tatcacacgg tcggtatttc aaaccattaa   3900
atttaggtca gaagatgaaa ttaactaaaa tatatttgaa aaagttttct cgcgttcttt   3960
gtcttgcgat tggatttgca tcagcattta catatagtta tataacccaa cctaagccgg   4020
aggttaaaaa ggtagtctct cagacctatg attttgataa attcactatt gactcttctc   4080
agcgtcttaa tctaagctat cgctatgttt tcaaggattc taagggaaaa ttaattaata   4140
gcgacgattt acagaagcaa ggttattcac tcacatatat tgatttatgt actgtttcca   4200
ttaaaaaagg taattcaaat gaaattgtta atgtaatta attttgtttt cttgatgttt   4260
gtttcatcat cttcttttgc tcaggtaatt gaaatgaata attcgcctct gcgcgatttt   4320
gtaacttggt attcaaagca atcaggcgaa tccgttattg tttctcccga tgtaaaaggt   4380
actgttactg tatattcatc tgacgttaaa cctgaaaatc tacgcaattt ctttatttct   4440
gttttacgtg caaataattt tgatatggta ggttctaacc cttccattat tcagaagtat   4500
aatccaaaca atcaggatta tattgatgaa ttgccatcat ctgataatca ggaatatgat   4560
gataattccg ctccttctgg tggtttcttt gttccgcaaa atgataatgt tactcaaact   4620
tttaaaatta ataacgttcg ggcaaaggat ttaatacgag ttgtcgaatt gtttgtaaag   4680
tctaatactt ctaaatcctc aaatgtatta tctattgacg gctctaatct attagttgtt   4740
agtgctccta aagatatttt agataaccct cctcaattcc tttcaactgt tgatttgcca   4800
actgaccaga tattgattga gggtttgata tttgaggttc agcaaggtga tgctttagat   4860
ttttcatttg ctgctggctc tcagcgtggc actgttgcag gcggtgttaa tactgaccgc   4920
ctcacctctg ttttatcttc tgctggtggt tcgttcggta tttttaatgg cgatgtttta   4980
gggctatcag ttcgcgcatt aaagactaat agccattcaa aaatattgtc tgtgccacgt   5040
attcttacgc tttcaggtca gaagggttct atctctgttg gccagaatgt ccctttatt    5100 actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
```

| | |
|---|---|
| actaatcaaa gaagtattgc tacaacggtt aatttgcgtg atggacagac tcttttactc | 5340 |
| ggtggcctca ctgattataa aaacacttct caggattctg gcgtaccgtt cctgtctaaa | 5400 |
| atcccttaa tcggcctcct gtttagctcc cgctctgatt ctaacgagga agcacgtta | 5460 |
| tacgtgctcg tcaaagcaac catagtacgc gccctgtagc ggcgcattaa gcgcggcggg | 5520 |
| tgtggtggtt acgcgcagcg tgaccgctac acttgccagc gccctagcgc ccgctccttt | 5580 |
| cgctttcttc ccttcctttc tcgccacgtt cgccggcttt ccccgtcaag ctctaaatcg | 5640 |
| ggggctccct ttagggttcc gatttagtgc tttacggcac ctcgacccca aaaaacttga | 5700 |
| tttgggtgat ggttcacgta gtgggccatc gccctgatag acggttttc gccctttgac | 5760 |
| gttggagtcc acgttcttta atagtggact cttgttccaa actggaacaa cactcaaccc | 5820 |
| tatctcgggc tattcttttg atttataagg gattttgccg atttcggaac caccatcaaa | 5880 |
| caggattttc gcctgctggg gcaaaccagc gtggaccgct tgctgcaact ctctcagggc | 5940 |
| caggcggtga agggcaatca gctgttgccc gtctcactgg tgaaaagaaa aaccaccctg | 6000 |
| gcgcccaata cgcaaaccgc ctctccccgc gcgttggccg attcattaat gcagctggca | 6060 |
| cgacaggttt cccgactgga aagcgggcag tgagcgcaac gcaattaatg tgagttagct | 6120 |
| cactcattag gcaccccagg ctttacactt tatgcttccg gctcgtatgt tgtgtggaat | 6180 |
| tgtgagcgga taacaatttc acacaggaaa cagctatgac catgattacg aattcgagct | 6240 |
| cggtacccgg ggatcctcta gagtcgacct gcaggcatgc aagcttggca ctggccgtcg | 6300 |
| ttttacaacg tcgtgactgg gaaaaccctg gcgttaccca acttaatcgc cttgcagcac | 6360 |
| atcccccttt cgccagctgg cgtaatagcg aagaggcccg caccgatcgc ccttcccaac | 6420 |
| agttgcgcag cctgaatggc gaatggcgct ttgcctggtt tccggcacca gaagcggtgc | 6480 |
| cggaaagctg gctggagtgc gatcttcctg aggccgatac tgtcgtcgtc ccctcaaact | 6540 |
| ggcagatgca cggttacgat gcgcccatct acaccaacgt gacctatccc attacggtca | 6600 |
| atccgccgtt tgttcccacg gagaatccga cgggttgtta ctcgctcaca tttaatgttg | 6660 |
| atgaaagctg gctacaggaa ggccagacgc gaattatttt tgatggcgtt cctattggtt | 6720 |
| aaaaaatgag ctgatttaac aaaaatttaa tgcgaatttt aacaaaatat taacgtttac | 6780 |
| aatttaaata tttgcttata caatcttcct gttttgggg cttttctgat tatcaaccgg | 6840 |
| ggtacatatg attgacatgc tagttttacg attaccgttc atcgattctc ttgtttgctc | 6900 |
| cagactctca ggcaatgacc tgatagcctt tgtagatctc tcaaaaatag ctaccctctc | 6960 |
| cggcattaat ttatcagcta gaacggttga atatcatatt gatggtgatt tgactgtctc | 7020 |
| cggcctttct caccctttg aatctttacc tacacattac tcaggcattg catttaaaat | 7080 |
| atatgagggt tctaaaaatt tttatccttg cgttgaaata aaggcttctc ccgcaaaagt | 7140 |
| attacagggt cataatgttt ttggtacaac cgatttagct ttatgctctg aggctttatt | 7200 |
| gcttaatttt gctaattctt tgccttgcct gtatgattta ttggatgtt | 7249 |

<210> SEQ ID NO 2
<211> LENGTH: 35
<212> TYPE: DNA
<213> ORGANISM: Artificial Sequence
<220> FEATURE:
<223> OTHER INFORMATION: Synthetic

<400> SEQUENCE: 2
aaaaaccaaa ccctcgttgt gaatatggtt tggtc                       35

```
<210> SEQ ID NO 3
<211> LENGTH: 42
<212> TYPE: DNA
<213> ORGANISM: artificial sequence
<220> FEATURE:
<223> OTHER INFORMATION: Synthetic

<400> SEQUENCE: 3
ggaagaagtg tagcggtcac gttataatca gcagactgat ag          42

<210> SEQ ID NO 4
<211> LENGTH: 24
<212> TYPE: DNA
<213> ORGANISM: artificial sequence
<220> FEATURE:
<223> OTHER INFORMATION: Synthetic

<400> SEQUENCE: 4
tacgatatag ataatcgaac aaca                              24

<210> SEQ ID NO 5
<211> LENGTH: 28
<212> TYPE: DNA
<213> ORGANISM: artificial sequence
<220> FEATURE:
<223> OTHER INFORMATION: Synthetic

<400> SEQUENCE: 5
cttttgctta agcaataaag cgagtaga                          28

<210> SEQ ID NO 6
<211> LENGTH: 32
<212> TYPE: DNA
<213> ORGANISM: artificial sequence
<220> FEATURE:
<223> OTHER INFORMATION: Synthetic

<400> SEQUENCE: 6
gtctgaaata acatcggtac ggccgcgcac gg                     32

<210> SEQ ID NO 7
<211> LENGTH: 31
<212> TYPE: DNA
<213> ORGANISM: artificial sequence
<220> FEATURE:
<223> OTHER INFORMATION: Synthetic

<400> SEQUENCE: 7
ggaagagcca aacagcttgc agggaaccta a                      31

<210> SEQ ID NO 8
<211> LENGTH: 28
<212> TYPE: DNA
<213> ORGANISM: artificial sequence
<220> FEATURE:
<223> OTHER INFORMATION: Synthetic

<400> SEQUENCE: 8
aaaatcaccg gaagcaaact ctgtagct                          28

<210> SEQ ID NO 9
<211> LENGTH: 39
<212> TYPE: DNA
<213> ORGANISM: artificial sequence
<220> FEATURE:
<223> OTHER INFORMATION: Synthetic
```

<400> SEQUENCE: 9
cctacatgaa gaactaaagg gcagggcgga gccccgggc					39

<210> SEQ ID NO 10
<211> LENGTH: 28
<212> TYPE: DNA
<213> ORGANISM: artificial sequence
<220> FEATURE:
<223> OTHER INFORMATION: Synthetic

<400> SEQUENCE: 10
catgtaaaaa ggtaaagtaa taagaacg					28

<210> SEQ ID NO 11
<211> LENGTH: 42
<212> TYPE: DNA
<213> ORGANISM: artificial sequence
<220> FEATURE:
<223> OTHER INFORMATION: Synthetic

<400> SEQUENCE: 11
attaaatcag gtcattgcct gtctagctga taaattgtaa ta					42

<210> SEQ ID NO 12
<211> LENGTH: 24
<212> TYPE: DNA
<213> ORGANISM: artificial sequence
<220> FEATURE:
<223> OTHER INFORMATION: Synthetic

<400> SEQUENCE: 12
atagtcgtct tttgcggtaa tgcc					24

<210> SEQ ID NO 13
<211> LENGTH: 31
<212> TYPE: DNA
<213> ORGANISM: artificial sequence
<220> FEATURE:
<223> OTHER INFORMATION: Synthetic

<400> SEQUENCE: 13
agtcatggtc atagctgaac tcactgccag t					31

<210> SEQ ID NO 14
<211> LENGTH: 31
<212> TYPE: DNA
<213> ORGANISM: artificial sequence
<220> FEATURE:
<223> OTHER INFORMATION: Synthetic

<400> SEQUENCE: 14
aactattgac ggaaatttga gggaatataa a					31

<210> SEQ ID NO 15
<211> LENGTH: 39
<212> TYPE: DNA
<213> ORGANISM: artificial sequence
<220> FEATURE:
<223> OTHER INFORMATION: Synthetic

<400> SEQUENCE: 15
atcgcgtctg gaagtttcat tccatataga aagaccatc					39

```
<210> SEQ ID NO 16
<211> LENGTH: 42
<212> TYPE: DNA
<213> ORGANISM: artificial sequence
<220> FEATURE:
<223> OTHER INFORMATION: Synthetic

<400> SEQUENCE: 16
aaatattgaa cggtaatcgt agccggagac agtcataaaa at          42

<210> SEQ ID NO 17
<211> LENGTH: 38
<212> TYPE: DNA
<213> ORGANISM: artificial sequence
<220> FEATURE:
<223> OTHER INFORMATION: Synthetic

<400> SEQUENCE: 17
gtctttacag gattagtatt ctaacgagca tagaacgc              38

<210> SEQ ID NO 18
<211> LENGTH: 28
<212> TYPE: DNA
<213> ORGANISM: artificial sequence
<220> FEATURE:
<223> OTHER INFORMATION: Synthetic

<400> SEQUENCE: 18
gcaccgcgac gacgctaatg aacagctg                         28

<210> SEQ ID NO 19
<211> LENGTH: 24
<212> TYPE: DNA
<213> ORGANISM: artificial sequence
<220> FEATURE:
<223> OTHER INFORMATION: Synthetic

<400> SEQUENCE: 19
aacttcattt tagaatcgca aatc                             24

<210> SEQ ID NO 20
<211> LENGTH: 38
<212> TYPE: DNA
<213> ORGANISM: artificial sequence
<220> FEATURE:
<223> OTHER INFORMATION: Synthetic

<400> SEQUENCE: 20
cgtagagtct ttgttaaggc cttcgttttc ctaccgag              38

<210> SEQ ID NO 21
<211> LENGTH: 28
<212> TYPE: DNA
<213> ORGANISM: artificial sequence
<220> FEATURE:
<223> OTHER INFORMATION: Synthetic

<400> SEQUENCE: 21
ccaatcaaag gcttatccgg ttgctatt                         28

<210> SEQ ID NO 22
<211> LENGTH: 28
<212> TYPE: DNA
<213> ORGANISM: artificial sequence
<220> FEATURE:
<223> OTHER INFORMATION: Synthetic
```

```
<400> SEQUENCE: 22
agaggcgata taatcctgat tcatcata                                              28

<210> SEQ ID NO 23
<211> LENGTH: 32
<212> TYPE: DNA
<213> ORGANISM: artificial sequence
<220> FEATURE:
<223> OTHER INFORMATION: Synthetic

<400> SEQUENCE: 23
ccgtaatccc tgaataataa cggaatacta cg                                         32

<210> SEQ ID NO 24
<211> LENGTH: 25
<212> TYPE: DNA
<213> ORGANISM: artificial sequence
<220> FEATURE:
<223> OTHER INFORMATION: Synthetic

<400> SEQUENCE: 24
aaatggtata cagggcaagg aaatc                                                 25

<210> SEQ ID NO 25
<211> LENGTH: 24
<212> TYPE: DNA
<213> ORGANISM: artificial sequence
<220> FEATURE:
<223> OTHER INFORMATION: Synthetic

<400> SEQUENCE: 25
tcctcatcgt aaccaagacc gaca                                                  24

<210> SEQ ID NO 26
<211> LENGTH: 35
<212> TYPE: DNA
<213> ORGANISM: artificial sequence
<220> FEATURE:
<223> OTHER INFORMATION: Synthetic

<400> SEQUENCE: 26
cattatctgg ctttagggaa ttatgtttgg attac                                      35

<210> SEQ ID NO 27
<211> LENGTH: 24
<212> TYPE: DNA
<213> ORGANISM: artificial sequence
<220> FEATURE:
<223> OTHER INFORMATION: Synthetic

<400> SEQUENCE: 27
acccgcccaa tcattcctct gtcc                                                  24

<210> SEQ ID NO 28
<211> LENGTH: 39
<212> TYPE: DNA
<213> ORGANISM: artificial sequence
<220> FEATURE:
<223> OTHER INFORMATION: Synthetic

<400> SEQUENCE: 28
cgaccagtca cgcagccacc gctggcaaag cgaaagaac                                  39
```

```
<210> SEQ ID NO 29
<211> LENGTH: 32
<212> TYPE: DNA
<213> ORGANISM: artificial sequence
<220> FEATURE:
<223> OTHER INFORMATION: Synthetic

<400> SEQUENCE: 29
ctaaaggcgt actatggttg caacaggaga ga                                      32

<210> SEQ ID NO 30
<211> LENGTH: 32
<212> TYPE: DNA
<213> ORGANISM: artificial sequence
<220> FEATURE:
<223> OTHER INFORMATION: Synthetic

<400> SEQUENCE: 30
ttggcaggca atacagtgtt tctgcgcggg cg                                      32

<210> SEQ ID NO 31
<211> LENGTH: 42
<212> TYPE: DNA
<213> ORGANISM: artificial sequence
<220> FEATURE:
<223> OTHER INFORMATION: Synthetic

<400> SEQUENCE: 31
tatacaggaa ataaagaaat tttgcccgaa cgttaagact tt                           42

<210> SEQ ID NO 32
<211> LENGTH: 42
<212> TYPE: DNA
<213> ORGANISM: artificial sequence
<220> FEATURE:
<223> OTHER INFORMATION: Synthetic

<400> SEQUENCE: 32
aagtatagta taaacagtta actgaattta ccgttgagcc ac                           42

<210> SEQ ID NO 33
<211> LENGTH: 28
<212> TYPE: DNA
<213> ORGANISM: artificial sequence
<220> FEATURE:
<223> OTHER INFORMATION: Synthetic

<400> SEQUENCE: 33
acattcagat agcgtccaat attcagaa                                           28

<210> SEQ ID NO 34
<211> LENGTH: 35
<212> TYPE: DNA
<213> ORGANISM: artificial sequence
<220> FEATURE:
<223> OTHER INFORMATION: Synthetic

<400> SEQUENCE: 34
aaacatcttt accctcacca gtaaagtgcc cgccc                                   35

<210> SEQ ID NO 35
<211> LENGTH: 28
<212> TYPE: DNA
<213> ORGANISM: artificial sequence
<220> FEATURE:
<223> OTHER INFORMATION: Synthetic
```

<400> SEQUENCE: 35
gagatgaccc taatgccagg ctattttt                                      28

<210> SEQ ID NO 36
<211> LENGTH: 32
<212> TYPE: DNA
<213> ORGANISM: artificial sequence
<220> FEATURE:
<223> OTHER INFORMATION: Synthetic

<400> SEQUENCE: 36
tcctgaattt tttgtttaac gatcagagcg ga                                 32

<210> SEQ ID NO 37
<211> LENGTH: 31
<212> TYPE: DNA
<213> ORGANISM: artificial sequence
<220> FEATURE:
<223> OTHER INFORMATION: Synthetic

<400> SEQUENCE: 37
gccgaaaaat ctaaagccaa tcaaggaaat a                                  31

<210> SEQ ID NO 38
<211> LENGTH: 49
<212> TYPE: DNA
<213> ORGANISM: artificial sequence
<220> FEATURE:
<223> OTHER INFORMATION: Synthetic

<400> SEQUENCE: 38
agcgtagcgc gttttcacaa aatctatgtt agcaaacgaa cgcaacaaa               49

<210> SEQ ID NO 39
<211> LENGTH: 28
<212> TYPE: DNA
<213> ORGANISM: artificial sequence
<220> FEATURE:
<223> OTHER INFORMATION: Synthetic

<400> SEQUENCE: 39
accaatcgat taaattgcgc cattatta                                      28

<210> SEQ ID NO 40
<211> LENGTH: 32
<212> TYPE: DNA
<213> ORGANISM: artificial sequence
<220> FEATURE:
<223> OTHER INFORMATION: Synthetic

<400> SEQUENCE: 40
atcttactta ttttcagcgc cgacaggatt ca                                 32

<210> SEQ ID NO 41
<211> LENGTH: 21
<212> TYPE: DNA
<213> ORGANISM: artificial sequence
<220> FEATURE:
<223> OTHER INFORMATION: Synthetic

<400> SEQUENCE: 41
ccctaaaaga acccagtcac a                                             21

<210> SEQ ID NO 42
<211> LENGTH: 35

<212> TYPE: DNA
<213> ORGANISM: artificial sequence
<220> FEATURE:
<223> OTHER INFORMATION: Synthetic

<400> SEQUENCE: 42
ggaagggcga aaatcgggtt tttcgcgttg ctcgt                              35

<210> SEQ ID NO 43
<211> LENGTH: 35
<212> TYPE: DNA
<213> ORGANISM: artificial sequence
<220> FEATURE:
<223> OTHER INFORMATION: Synthetic

<400> SEQUENCE: 43
cagaccggaa gccgccattt tgatggggtc agtac                              35

<210> SEQ ID NO 44
<211> LENGTH: 42
<212> TYPE: DNA
<213> ORGANISM: artificial sequence
<220> FEATURE:
<223> OTHER INFORMATION: Synthetic

<400> SEQUENCE: 44
taatattgga gcaaacaaga gatcaatatg atattgcctt ta                      42

<210> SEQ ID NO 45
<211> LENGTH: 28
<212> TYPE: DNA
<213> ORGANISM: artificial sequence
<220> FEATURE:
<223> OTHER INFORMATION: Synthetic

<400> SEQUENCE: 45
ttccttatag caagcaaatc aaatttta                                      28

<210> SEQ ID NO 46
<211> LENGTH: 36
<212> TYPE: DNA
<213> ORGANISM: artificial sequence
<220> FEATURE:
<223> OTHER INFORMATION: Synthetic

<400> SEQUENCE: 46
actacgagga gattttttca cgttgaaact tgcttt                             36

<210> SEQ ID NO 47
<211> LENGTH: 42
<212> TYPE: DNA
<213> ORGANISM: artificial sequence
<220> FEATURE:
<223> OTHER INFORMATION: Synthetic

<400> SEQUENCE: 47
aaacaggcat gtcaatcata tagattcaaa agggttatat tt                      42

<210> SEQ ID NO 48
<211> LENGTH: 38
<212> TYPE: DNA
<213> ORGANISM: artificial sequence
<220> FEATURE:
<223> OTHER INFORMATION: Synthetic

<400> SEQUENCE: 48
aacaggcacc agttaaaggc cgctttgtga atttctta        38

<210> SEQ ID NO 49
<211> LENGTH: 40
<212> TYPE: DNA
<213> ORGANISM: artificial sequence
<220> FEATURE:
<223> OTHER INFORMATION: Synthetic

<400> SEQUENCE: 49
ttcctgagtt atctaaaata ttcagttgtt caaatagcag        40

<210> SEQ ID NO 50
<211> LENGTH: 24
<212> TYPE: DNA
<213> ORGANISM: artificial sequence
<220> FEATURE:
<223> OTHER INFORMATION: Synthetic

<400> SEQUENCE: 50
aaagaaacaa gagaagatcc ggct        24

<210> SEQ ID NO 51
<211> LENGTH: 28
<212> TYPE: DNA
<213> ORGANISM: artificial sequence
<220> FEATURE:
<223> OTHER INFORMATION: Synthetic

<400> SEQUENCE: 51
ttgagggttc tggtcaggct gtataagc        28

<210> SEQ ID NO 52
<211> LENGTH: 42
<212> TYPE: DNA
<213> ORGANISM: artificial sequence
<220> FEATURE:
<223> OTHER INFORMATION: Synthetic

<400> SEQUENCE: 52
tttaaccgtc aatagtgaat tcaaaagaag atgatatcgc gc        42

<210> SEQ ID NO 53
<211> LENGTH: 32
<212> TYPE: DNA
<213> ORGANISM: artificial sequence
<220> FEATURE:
<223> OTHER INFORMATION: Synthetic

<400> SEQUENCE: 53
acgagcgccc aatccaaata aaattgagca cc        32

<210> SEQ ID NO 54
<211> LENGTH: 32
<212> TYPE: DNA
<213> ORGANISM: artificial sequence
<220> FEATURE:
<223> OTHER INFORMATION: Synthetic

<400> SEQUENCE: 54
aataagtcga agcccaataa ttatttattc tt        32

<210> SEQ ID NO 55
<211> LENGTH: 35

```
<212> TYPE: DNA
<213> ORGANISM: artificial sequence
<220> FEATURE:
<223> OTHER INFORMATION: Synthetic

<400> SEQUENCE: 55
acgaaatatc atagattaag aaacaatgga actga                                35

<210> SEQ ID NO 56
<211> LENGTH: 31
<212> TYPE: DNA
<213> ORGANISM: artificial sequence
<220> FEATURE:
<223> OTHER INFORMATION: Synthetic

<400> SEQUENCE: 56
tttcatagtt gtaccgtaac actggggttt t                                    31

<210> SEQ ID NO 57
<211> LENGTH: 42
<212> TYPE: DNA
<213> ORGANISM: artificial sequence
<220> FEATURE:
<223> OTHER INFORMATION: Synthetic

<400> SEQUENCE: 57
aggagcgagc actaacaact aaaaccctat cacctaacag tg                        42

<210> SEQ ID NO 58
<211> LENGTH: 35
<212> TYPE: DNA
<213> ORGANISM: artificial sequence
<220> FEATURE:
<223> OTHER INFORMATION: Synthetic

<400> SEQUENCE: 58
caaagtatta attagcgagt ttcgccacag aacga                                35

<210> SEQ ID NO 59
<211> LENGTH: 35
<212> TYPE: DNA
<213> ORGANISM: artificial sequence
<220> FEATURE:
<223> OTHER INFORMATION: Synthetic

<400> SEQUENCE: 59
tggggagcta tttgacgact aaataccatc agttt                                35

<210> SEQ ID NO 60
<211> LENGTH: 28
<212> TYPE: DNA
<213> ORGANISM: artificial sequence
<220> FEATURE:
<223> OTHER INFORMATION: Synthetic

<400> SEQUENCE: 60
ataacgcaat agtaaaatgt ttaaatca                                        28

<210> SEQ ID NO 61
<211> LENGTH: 28
<212> TYPE: DNA
<213> ORGANISM: artificial sequence
<220> FEATURE:
<223> OTHER INFORMATION: Synthetic

<400> SEQUENCE: 61
```
acgaatcaac cttcatctta taccgagg                                              28

<210> SEQ ID NO 62
<211> LENGTH: 21
<212> TYPE: DNA
<213> ORGANISM: artificial sequence
<220> FEATURE:
<223> OTHER INFORMATION: Synthetic

<400> SEQUENCE: 62
taatggtttg aaatacgcca a                                                      21

<210> SEQ ID NO 63
<211> LENGTH: 42
<212> TYPE: DNA
<213> ORGANISM: artificial sequence
<220> FEATURE:
<223> OTHER INFORMATION: Synthetic

<400> SEQUENCE: 63
cggaacaaga gccgtcaata ggcacagaca atatcctcaa tc                              42

<210> SEQ ID NO 64
<211> LENGTH: 31
<212> TYPE: DNA
<213> ORGANISM: artificial sequence
<220> FEATURE:
<223> OTHER INFORMATION: Synthetic

<400> SEQUENCE: 64
attaaaggtg aattatcaaa gggcaccacg g                                          31

<210> SEQ ID NO 65
<211> LENGTH: 31
<212> TYPE: DNA
<213> ORGANISM: artificial sequence
<220> FEATURE:
<223> OTHER INFORMATION: Synthetic

<400> SEQUENCE: 65
ggcaacccat agcgtaagca gcgaccatta a                                          31

<210> SEQ ID NO 66
<211> LENGTH: 32
<212> TYPE: DNA
<213> ORGANISM: artificial sequence
<220> FEATURE:
<223> OTHER INFORMATION: Synthetic

<400> SEQUENCE: 66
agaaacgtaa gcagccacaa ggaaacgatc tt                                         32

<210> SEQ ID NO 67
<211> LENGTH: 28
<212> TYPE: DNA
<213> ORGANISM: artificial sequence
<220> FEATURE:
<223> OTHER INFORMATION: Synthetic

<400> SEQUENCE: 67
agaggtcttt aggggtcaa aaggcagt                                               28

<210> SEQ ID NO 68
<211> LENGTH: 42
<212> TYPE: DNA
<213> ORGANISM: artificial sequence

```
<220> FEATURE:
<223> OTHER INFORMATION: Synthetic

<400> SEQUENCE: 68
ggggactttt tcatgaggac ctgcgagaat agaaaggagg at                42

<210> SEQ ID NO 69
<211> LENGTH: 28
<212> TYPE: DNA
<213> ORGANISM: artificial sequence
<220> FEATURE:
<223> OTHER INFORMATION: Synthetic

<400> SEQUENCE: 69
ttttagaaca tccaataaat ccaataac                                28

<210> SEQ ID NO 70
<211> LENGTH: 28
<212> TYPE: DNA
<213> ORGANISM: artificial sequence
<220> FEATURE:
<223> OTHER INFORMATION: Synthetic

<400> SEQUENCE: 70
aaatgtggta gatggcccgc ttgggcgc                                28

<210> SEQ ID NO 71
<211> LENGTH: 31
<212> TYPE: DNA
<213> ORGANISM: artificial sequence
<220> FEATURE:
<223> OTHER INFORMATION: Synthetic

<400> SEQUENCE: 71
acggatcgtc accctcacga tctagaattt t                            31

<210> SEQ ID NO 72
<211> LENGTH: 28
<212> TYPE: DNA
<213> ORGANISM: artificial sequence
<220> FEATURE:
<223> OTHER INFORMATION: Synthetic

<400> SEQUENCE: 72
cgccataaga cgacgacaat agctgtct                                28

<210> SEQ ID NO 73
<211> LENGTH: 31
<212> TYPE: DNA
<213> ORGANISM: artificial sequence
<220> FEATURE:
<223> OTHER INFORMATION: Synthetic

<400> SEQUENCE: 73
gcgtattagt ctttaatcgt aagaatttac a                            31

<210> SEQ ID NO 74
<211> LENGTH: 35
<212> TYPE: DNA
<213> ORGANISM: artificial sequence
<220> FEATURE:
<223> OTHER INFORMATION: Synthetic

<400> SEQUENCE: 74
agagaacgtg aatcaaatgc gtatttccag tcccc                        35
```

<210> SEQ ID NO 75
<211> LENGTH: 33
<212> TYPE: DNA
<213> ORGANISM: artificial sequence
<220> FEATURE:
<223> OTHER INFORMATION: Synthetic

<400> SEQUENCE: 75
aacgaaaaag cgcgaaaaaa aggctccaaa agg                                   33

<210> SEQ ID NO 76
<211> LENGTH: 28
<212> TYPE: DNA
<213> ORGANISM: artificial sequence
<220> FEATURE:
<223> OTHER INFORMATION: Synthetic

<400> SEQUENCE: 76
taatttagaa cgcgaggcgt taagcctt                                        28

<210> SEQ ID NO 77
<211> LENGTH: 28
<212> TYPE: DNA
<213> ORGANISM: artificial sequence
<220> FEATURE:
<223> OTHER INFORMATION: Synthetic

<400> SEQUENCE: 77
accaggcgtg catcattaat tttttcac                                        28

<210> SEQ ID NO 78
<211> LENGTH: 28
<212> TYPE: DNA
<213> ORGANISM: artificial sequence
<220> FEATURE:
<223> OTHER INFORMATION: Synthetic

<400> SEQUENCE: 78
cagcctgacg acagatgtcg cctgaaat                                        28

<210> SEQ ID NO 79
<211> LENGTH: 35
<212> TYPE: DNA
<213> ORGANISM: artificial sequence
<220> FEATURE:
<223> OTHER INFORMATION: Synthetic

<400> SEQUENCE: 79
attagtcaga ttgcaaagta agagttaaga agagt                                35

<210> SEQ ID NO 80
<211> LENGTH: 21
<212> TYPE: DNA
<213> ORGANISM: artificial sequence
<220> FEATURE:
<223> OTHER INFORMATION: Synthetic

<400> SEQUENCE: 80
ctcgaatgct cactggcgca t                                               21

<210> SEQ ID NO 81
<211> LENGTH: 31
<212> TYPE: DNA
<213> ORGANISM: artificial sequence
<220> FEATURE:
<223> OTHER INFORMATION: Synthetic

<400> SEQUENCE: 81
gggcagtcac gacgttgaat aattaacaac c                          31

<210> SEQ ID NO 82
<211> LENGTH: 38
<212> TYPE: DNA
<213> ORGANISM: artificial sequence
<220> FEATURE:
<223> OTHER INFORMATION: Synthetic

<400> SEQUENCE: 82
taaaaacagg ggttttgtta gcgaataata taatagat                    38

<210> SEQ ID NO 83
<211> LENGTH: 31
<212> TYPE: DNA
<213> ORGANISM: artificial sequence
<220> FEATURE:
<223> OTHER INFORMATION: Synthetic

<400> SEQUENCE: 83
tcaaccctca gcgccgaata tattaagaat a                           31

<210> SEQ ID NO 84
<211> LENGTH: 35
<212> TYPE: DNA
<213> ORGANISM: artificial sequence
<220> FEATURE:
<223> OTHER INFORMATION: Synthetic

<400> SEQUENCE: 84
attatacgtg ataatacaca ttatcatatc agaga                       35

<210> SEQ ID NO 85
<211> LENGTH: 25
<212> TYPE: DNA
<213> ORGANISM: artificial sequence
<220> FEATURE:
<223> OTHER INFORMATION: Synthetic

<400> SEQUENCE: 85
gcaaatctgc aacaggaaaa attgc                                  25

<210> SEQ ID NO 86
<211> LENGTH: 21
<212> TYPE: DNA
<213> ORGANISM: artificial sequence
<220> FEATURE:
<223> OTHER INFORMATION: Synthetic

<400> SEQUENCE: 86
ataattacta gaaattctta c                                      21

<210> SEQ ID NO 87
<211> LENGTH: 42
<212> TYPE: DNA
<213> ORGANISM: artificial sequence
<220> FEATURE:
<223> OTHER INFORMATION: Synthetic

<400> SEQUENCE: 87
tatcaccgtg ccttgagtaa cgcgtcatac atggcccctc ag               42

<210> SEQ ID NO 88

<211> LENGTH: 28
<212> TYPE: DNA
<213> ORGANISM: artificial sequence
<220> FEATURE:
<223> OTHER INFORMATION: Synthetic

<400> SEQUENCE: 88
aagtagggtt aacgcgctgc cagctgca                                    28

<210> SEQ ID NO 89
<211> LENGTH: 32
<212> TYPE: DNA
<213> ORGANISM: artificial sequence
<220> FEATURE:
<223> OTHER INFORMATION: Synthetic

<400> SEQUENCE: 89
ccagtagtta agcccttttt aagaaaagca aa                               32

<210> SEQ ID NO 90
<211> LENGTH: 21
<212> TYPE: DNA
<213> ORGANISM: artificial sequence
<220> FEATURE:
<223> OTHER INFORMATION: Synthetic

<400> SEQUENCE: 90
tggcgaagtt gggactttcc g                                           21

<210> SEQ ID NO 91
<211> LENGTH: 42
<212> TYPE: DNA
<213> ORGANISM: artificial sequence
<220> FEATURE:
<223> OTHER INFORMATION: Synthetic

<400> SEQUENCE: 91
cagtgagtga tggtggttcc gaaaaccgtc tatcacgatt ta                    42

<210> SEQ ID NO 92
<211> LENGTH: 32
<212> TYPE: DNA
<213> ORGANISM: artificial sequence
<220> FEATURE:
<223> OTHER INFORMATION: Synthetic

<400> SEQUENCE: 92
aaatcaaaga gaataacata actgaacaca gt                               32

<210> SEQ ID NO 93
<211> LENGTH: 21
<212> TYPE: DNA
<213> ORGANISM: artificial sequence
<220> FEATURE:
<223> OTHER INFORMATION: Synthetic

<400> SEQUENCE: 93
ctgtatgaca actagtgtcg a                                           21

<210> SEQ ID NO 94
<211> LENGTH: 42
<212> TYPE: DNA
<213> ORGANISM: artificial sequence
<220> FEATURE:
<223> OTHER INFORMATION: Synthetic

<400> SEQUENCE: 94

```
atcataaata gcgagaggct tagcaaagcg gattgttcaa at          42

<210> SEQ ID NO 95
<211> LENGTH: 42
<212> TYPE: DNA
<213> ORGANISM: artificial sequence
<220> FEATURE:
<223> OTHER INFORMATION: Synthetic

<400> SEQUENCE: 95
ttgagtaatt tgaggattta gctgaaaggc gcgaaagata aa          42

<210> SEQ ID NO 96
<211> LENGTH: 21
<212> TYPE: DNA
<213> ORGANISM: artificial sequence
<220> FEATURE:
<223> OTHER INFORMATION: Synthetic

<400> SEQUENCE: 96
ataagaataa acaccgctca a                                 21

<210> SEQ ID NO 97
<211> LENGTH: 32
<212> TYPE: DNA
<213> ORGANISM: artificial sequence
<220> FEATURE:
<223> OTHER INFORMATION: Synthetic

<400> SEQUENCE: 97
cgttgtaatt caccttctga caagtatttt aa                     32

<210> SEQ ID NO 98
<211> LENGTH: 28
<212> TYPE: DNA
<213> ORGANISM: artificial sequence
<220> FEATURE:
<223> OTHER INFORMATION: Synthetic

<400> SEQUENCE: 98
aaccgcctca taattcggca tagcagca                          28

<210> SEQ ID NO 99
<211> LENGTH: 38
<212> TYPE: DNA
<213> ORGANISM: artificial sequence
<220> FEATURE:
<223> OTHER INFORMATION: Synthetic

<400> SEQUENCE: 99
aaataggtca cgttggtagc gagtcgcgtc taattcgc                38

<210> SEQ ID NO 100
<211> LENGTH: 28
<212> TYPE: DNA
<213> ORGANISM: artificial sequence
<220> FEATURE:
<223> OTHER INFORMATION: Synthetic

<400> SEQUENCE: 100
cagtatagcc tgtttatcaa ccccatcc                          28

<210> SEQ ID NO 101
<211> LENGTH: 42
<212> TYPE: DNA
```

<213> ORGANISM: artificial sequence
<220> FEATURE:
<223> OTHER INFORMATION: Synthetic

<400> SEQUENCE: 101
ttgcacctga aaatagcagc cagagggtca tcgattttcg gt    42

<210> SEQ ID NO 102
<211> LENGTH: 28
<212> TYPE: DNA
<213> ORGANISM: artificial sequence
<220> FEATURE:
<223> OTHER INFORMATION: Synthetic

<400> SEQUENCE: 102
cgtcggaaat gggacctgtc gggggaga    28

<210> SEQ ID NO 103
<211> LENGTH: 28
<212> TYPE: DNA
<213> ORGANISM: artificial sequence
<220> FEATURE:
<223> OTHER INFORMATION: Synthetic

<400> SEQUENCE: 103
aagaaactag aagattgcgc aactaggg    28

<210> SEQ ID NO 104
<211> LENGTH: 28
<212> TYPE: DNA
<213> ORGANISM: artificial sequence
<220> FEATURE:
<223> OTHER INFORMATION: Synthetic

<400> SEQUENCE: 104
ccagaacctg gctcattata caattacg    28

<210> SEQ ID NO 105
<211> LENGTH: 32
<212> TYPE: DNA
<213> ORGANISM: artificial sequence
<220> FEATURE:
<223> OTHER INFORMATION: Synthetic

<400> SEQUENCE: 105
acgggtaata aattaaggaa ttgcgaatag ta    32

<210> SEQ ID NO 106
<211> LENGTH: 32
<212> TYPE: DNA
<213> ORGANISM: artificial sequence
<220> FEATURE:
<223> OTHER INFORMATION: Synthetic

<400> SEQUENCE: 106
ccacgctggc cgattcaaac tatcggcccg ct    32

<210> SEQ ID NO 107
<211> LENGTH: 31
<212> TYPE: DNA
<213> ORGANISM: artificial sequence
<220> FEATURE:
<223> OTHER INFORMATION: Synthetic

<400> SEQUENCE: 107
gccttcaccg aaagcctccg ctcacgccag c    31

<210> SEQ ID NO 108
<211> LENGTH: 28
<212> TYPE: DNA
<213> ORGANISM: artificial sequence
<220> FEATURE:
<223> OTHER INFORMATION: Synthetic

<400> SEQUENCE: 108
cagcattaaa gacaaccgtc aaaaatca                                      28

<210> SEQ ID NO 109
<211> LENGTH: 28
<212> TYPE: DNA
<213> ORGANISM: artificial sequence
<220> FEATURE:
<223> OTHER INFORMATION: Synthetic

<400> SEQUENCE: 109
acatcggaaa ttatttgcac gtaaaagt                                      28

<210> SEQ ID NO 110
<211> LENGTH: 42
<212> TYPE: DNA
<213> ORGANISM: artificial sequence
<220> FEATURE:
<223> OTHER INFORMATION: Synthetic

<400> SEQUENCE: 110
caacggtcgc tgaggcttga tacctatcgg tttatcagat ct                      42

<210> SEQ ID NO 111
<211> LENGTH: 28
<212> TYPE: DNA
<213> ORGANISM: artificial sequence
<220> FEATURE:
<223> OTHER INFORMATION: Synthetic

<400> SEQUENCE: 111
aaatcgtaca gtacataaat cagatgaa                                      28

<210> SEQ ID NO 112
<211> LENGTH: 32
<212> TYPE: DNA
<213> ORGANISM: artificial sequence
<220> FEATURE:
<223> OTHER INFORMATION: Synthetic

<400> SEQUENCE: 112
ttaacacaca ggaacacttg cctgagtatt tg                                 32

<210> SEQ ID NO 113
<211> LENGTH: 28
<212> TYPE: DNA
<213> ORGANISM: artificial sequence
<220> FEATURE:
<223> OTHER INFORMATION: Synthetic

<400> SEQUENCE: 113
aggcataaga agttttgcca gaccctga                                      28

<210> SEQ ID NO 114
<211> LENGTH: 35
<212> TYPE: DNA
<213> ORGANISM: artificial sequence
<220> FEATURE:

<223> OTHER INFORMATION: Synthetic

<400> SEQUENCE: 114
gacgacattc accagagatt aaagcctatt aacca                35

<210> SEQ ID NO 115
<211> LENGTH: 28
<212> TYPE: DNA
<213> ORGANISM: artificial sequence
<220> FEATURE:
<223> OTHER INFORMATION: Synthetic

<400> SEQUENCE: 115
agctgctcgt taataaaacg agaatacc                        28

<210> SEQ ID NO 116
<211> LENGTH: 39
<212> TYPE: DNA
<213> ORGANISM: artificial sequence
<220> FEATURE:
<223> OTHER INFORMATION: Synthetic

<400> SEQUENCE: 116
cttagagtac cttttaaaca gctgcggaga tttagacta             39

<210> SEQ ID NO 117
<211> LENGTH: 28
<212> TYPE: DNA
<213> ORGANISM: artificial sequence
<220> FEATURE:
<223> OTHER INFORMATION: Synthetic

<400> SEQUENCE: 117
caccctctaa ttagcgtttg ctacatac                        28

<210> SEQ ID NO 118
<211> LENGTH: 42
<212> TYPE: DNA
<213> ORGANISM: artificial sequence
<220> FEATURE:
<223> OTHER INFORMATION: Synthetic

<400> SEQUENCE: 118
gaaccgaaaa ttgggcttga gtaccttatg cgattcaaca ct         42

<210> SEQ ID NO 119
<211> LENGTH: 39
<212> TYPE: DNA
<213> ORGANISM: artificial sequence
<220> FEATURE:
<223> OTHER INFORMATION: Synthetic

<400> SEQUENCE: 119
gcaaggcaga taacatagcc gaacaaagtg gcaacggga             39

<210> SEQ ID NO 120
<211> LENGTH: 32
<212> TYPE: DNA
<213> ORGANISM: artificial sequence
<220> FEATURE:
<223> OTHER INFORMATION: Synthetic

<400> SEQUENCE: 120
atgaaacaat tgagaaggaa accgaggata ga                    32

<210> SEQ ID NO 121
<211> LENGTH: 31
<212> TYPE: DNA
<213> ORGANISM: artificial sequence
<220> FEATURE:
<223> OTHER INFORMATION: Synthetic

<400> SEQUENCE: 121
ggatgtgaaa ttgttatggg gtgcacagta t                            31

<210> SEQ ID NO 122
<211> LENGTH: 28
<212> TYPE: DNA
<213> ORGANISM: artificial sequence
<220> FEATURE:
<223> OTHER INFORMATION: Synthetic

<400> SEQUENCE: 122
ggcttgcgac gttgggaaga acagatac                                28

<210> SEQ ID NO 123
<211> LENGTH: 28
<212> TYPE: DNA
<213> ORGANISM: artificial sequence
<220> FEATURE:
<223> OTHER INFORMATION: Synthetic

<400> SEQUENCE: 123
taaatgccta ctaatagtag ttttcatt                                28

<210> SEQ ID NO 124
<211> LENGTH: 45
<212> TYPE: DNA
<213> ORGANISM: artificial sequence
<220> FEATURE:
<223> OTHER INFORMATION: Synthetic

<400> SEQUENCE: 124
tgccgtctgc ctatttcgga accagaatgg aaagcccacc agaac             45

<210> SEQ ID NO 125
<211> LENGTH: 25
<212> TYPE: DNA
<213> ORGANISM: artificial sequence
<220> FEATURE:
<223> OTHER INFORMATION: Synthetic

<400> SEQUENCE: 125
tgaccatagc aaaagggaga acaac                                   25

<210> SEQ ID NO 126
<211> LENGTH: 27
<212> TYPE: DNA
<213> ORGANISM: artificial sequence
<220> FEATURE:
<223> OTHER INFORMATION: Synthetic

<400> SEQUENCE: 126
cgagccagac gttaataatt tgtatca                                 27

<210> SEQ ID NO 127
<211> LENGTH: 42
<212> TYPE: DNA
<213> ORGANISM: artificial sequence
<220> FEATURE:
<223> OTHER INFORMATION: Synthetic

<400> SEQUENCE: 127
gctcagtttc tgaaacatga aacaaataaa tcctcccgcc gc            42

<210> SEQ ID NO 128
<211> LENGTH: 28
<212> TYPE: DNA
<213> ORGANISM: artificial sequence
<220> FEATURE:
<223> OTHER INFORMATION: Synthetic

<400> SEQUENCE: 128
agacgctaca tcaagaaaac actttgaa            28

<210> SEQ ID NO 129
<211> LENGTH: 31
<212> TYPE: DNA
<213> ORGANISM: artificial sequence
<220> FEATURE:
<223> OTHER INFORMATION: Synthetic

<400> SEQUENCE: 129
agtactgacc aatccgcgaa gtttaagaca g            31

<210> SEQ ID NO 130
<211> LENGTH: 38
<212> TYPE: DNA
<213> ORGANISM: artificial sequence
<220> FEATURE:
<223> OTHER INFORMATION: Synthetic

<400> SEQUENCE: 130
gattcctgtt acgggcagtg agcttttcct gtgtgctg            38

<210> SEQ ID NO 131
<211> LENGTH: 28
<212> TYPE: DNA
<213> ORGANISM: artificial sequence
<220> FEATURE:
<223> OTHER INFORMATION: Synthetic

<400> SEQUENCE: 131
ggtattaagg aatcattacc gaacgcta            28

<210> SEQ ID NO 132
<211> LENGTH: 35
<212> TYPE: DNA
<213> ORGANISM: artificial sequence
<220> FEATURE:
<223> OTHER INFORMATION: Synthetic

<400> SEQUENCE: 132
gttcatcaaa taaaacgcga ctctagagga tcggg            35

<210> SEQ ID NO 133
<211> LENGTH: 40
<212> TYPE: DNA
<213> ORGANISM: artificial sequence
<220> FEATURE:
<223> OTHER INFORMATION: Synthetic

<400> SEQUENCE: 133
agcctttaat tggatagttg aaccgccacc ctcataggtg            40

<210> SEQ ID NO 134
<211> LENGTH: 32

<212> TYPE: DNA
<213> ORGANISM: artificial sequence
<220> FEATURE:
<223> OTHER INFORMATION: Synthetic

<400> SEQUENCE: 134
acagaggcct gagattcttt gattagtaat gg          32

<210> SEQ ID NO 135
<211> LENGTH: 28
<212> TYPE: DNA
<213> ORGANISM: artificial sequence
<220> FEATURE:
<223> OTHER INFORMATION: Synthetic

<400> SEQUENCE: 135
aacgagatca ggattagaga gcttaatt              28

<210> SEQ ID NO 136
<211> LENGTH: 28
<212> TYPE: DNA
<213> ORGANISM: artificial sequence
<220> FEATURE:
<223> OTHER INFORMATION: Synthetic

<400> SEQUENCE: 136
taccaagtta tacttctgaa tcaccaga              28

<210> SEQ ID NO 137
<211> LENGTH: 28
<212> TYPE: DNA
<213> ORGANISM: artificial sequence
<220> FEATURE:
<223> OTHER INFORMATION: Synthetic

<400> SEQUENCE: 137
cagtaggtgt tcagctaatg cgtagaaa              28

<210> SEQ ID NO 138
<211> LENGTH: 49
<212> TYPE: DNA
<213> ORGANISM: artificial sequence
<220> FEATURE:
<223> OTHER INFORMATION: Synthetic

<400> SEQUENCE: 138
aggatgacca tagactgact aatgaaatct acattcagca ggcgcgtac          49

<210> SEQ ID NO 139
<211> LENGTH: 28
<212> TYPE: DNA
<213> ORGANISM: artificial sequence
<220> FEATURE:
<223> OTHER INFORMATION: Synthetic

<400> SEQUENCE: 139
tttcaaccaa ggcaaagaat ttagatac              28

<210> SEQ ID NO 140
<211> LENGTH: 24
<212> TYPE: DNA
<213> ORGANISM: artificial sequence
<220> FEATURE:
<223> OTHER INFORMATION: Synthetic

<400> SEQUENCE: 140
ttgaaattaa gatagcttaa ctat                                                   24

<210> SEQ ID NO 141
<211> LENGTH: 28
<212> TYPE: DNA
<213> ORGANISM: artificial sequence
<220> FEATURE:
<223> OTHER INFORMATION: Synthetic

<400> SEQUENCE: 141
ctattatcga gcttcaaagc gtatgcaa                                               28

<210> SEQ ID NO 142
<211> LENGTH: 42
<212> TYPE: DNA
<213> ORGANISM: artificial sequence
<220> FEATURE:
<223> OTHER INFORMATION: Synthetic

<400> SEQUENCE: 142
cagggtgcaa aatcccttat agactccaac gtcaaaagcc gg                               42

<210> SEQ ID NO 143
<211> LENGTH: 42
<212> TYPE: DNA
<213> ORGANISM: artificial sequence
<220> FEATURE:
<223> OTHER INFORMATION: Synthetic

<400> SEQUENCE: 143
gagcttgtta atgcgccgct aattttagcg cctgctgctg aa                               42

<210> SEQ ID NO 144
<211> LENGTH: 32
<212> TYPE: DNA
<213> ORGANISM: artificial sequence
<220> FEATURE:
<223> OTHER INFORMATION: Synthetic

<400> SEQUENCE: 144
cgaacgttaa ccaccacacc cccagaattg ag                                          32

<210> SEQ ID NO 145
<211> LENGTH: 21
<212> TYPE: DNA
<213> ORGANISM: artificial sequence
<220> FEATURE:
<223> OTHER INFORMATION: Synthetic

<400> SEQUENCE: 145
gtgtgataaa taagtgagaa t                                                      21

<210> SEQ ID NO 146
<211> LENGTH: 25
<212> TYPE: DNA
<213> ORGANISM: artificial sequence
<220> FEATURE:
<223> OTHER INFORMATION: Synthetic

<400> SEQUENCE: 146
gctatatagc attaaccctc agaga                                                  25

<210> SEQ ID NO 147
<211> LENGTH: 35
<212> TYPE: DNA
<213> ORGANISM: artificial sequence -continued

```
<220> FEATURE:
<223> OTHER INFORMATION: Synthetic

<400> SEQUENCE: 147
aggagagccg gcagtcttgc ccccgagagg gaggg                                35

<210> SEQ ID NO 148
<211> LENGTH: 28
<212> TYPE: DNA
<213> ORGANISM: artificial sequence
<220> FEATURE:
<223> OTHER INFORMATION: Synthetic

<400> SEQUENCE: 148
cggcctccag ccagagggcg agccccaa                                       28

<210> SEQ ID NO 149
<211> LENGTH: 31
<212> TYPE: DNA
<213> ORGANISM: artificial sequence
<220> FEATURE:
<223> OTHER INFORMATION: Synthetic

<400> SEQUENCE: 149
ccaaaacaaa ataggctggc tgacgtaaca a                                   31

<210> SEQ ID NO 150
<211> LENGTH: 42
<212> TYPE: DNA
<213> ORGANISM: artificial sequence
<220> FEATURE:
<223> OTHER INFORMATION: Synthetic

<400> SEQUENCE: 150
ggcggttaga atagcccgag aagtccacta ttaaaaagga ag                       42

<210> SEQ ID NO 151
<211> LENGTH: 32
<212> TYPE: DNA
<213> ORGANISM: artificial sequence
<220> FEATURE:
<223> OTHER INFORMATION: Synthetic

<400> SEQUENCE: 151
ataaaggtta ccagcgctaa ttcaaaaaca gc                                  32

<210> SEQ ID NO 152
<211> LENGTH: 42
<212> TYPE: DNA
<213> ORGANISM: artificial sequence
<220> FEATURE:
<223> OTHER INFORMATION: Synthetic

<400> SEQUENCE: 152
attgccccca gcaggcgaaa aggcccacta cgtgacggaa cc                       42

<210> SEQ ID NO 153
<211> LENGTH: 38
<212> TYPE: DNA
<213> ORGANISM: artificial sequence
<220> FEATURE:
<223> OTHER INFORMATION: Synthetic

<400> SEQUENCE: 153
ttttaaaaca taacagtaat ggaacgctat tagaacgc                            38
```

<210> SEQ ID NO 154
<211> LENGTH: 38
<212> TYPE: DNA
<213> ORGANISM: artificial sequence
<220> FEATURE:
<223> OTHER INFORMATION: Synthetic

<400> SEQUENCE: 154
aattgggtaa cgccaggctg tagccagcta gtaaacgt                      38

<210> SEQ ID NO 155
<211> LENGTH: 41
<212> TYPE: DNA
<213> ORGANISM: artificial sequence
<220> FEATURE:
<223> OTHER INFORMATION: Synthetic

<400> SEQUENCE: 155
ttacccagaa caacattatt acaggttttt ttttttttt t                   41

<210> SEQ ID NO 156
<211> LENGTH: 28
<212> TYPE: DNA
<213> ORGANISM: artificial sequence
<220> FEATURE:
<223> OTHER INFORMATION: Synthetic

<400> SEQUENCE: 156
tttttttttt tttttaata agagaata                                  28

<210> SEQ ID NO 157
<211> LENGTH: 48
<212> TYPE: DNA
<213> ORGANISM: artificial sequence
<220> FEATURE:
<223> OTHER INFORMATION: Synthetic

<400> SEQUENCE: 157
tttttttttt tttttccag tttgggagcg ggcttttttt tttttttt            48

<210> SEQ ID NO 158
<211> LENGTH: 31
<212> TYPE: DNA
<213> ORGANISM: artificial sequence
<220> FEATURE:
<223> OTHER INFORMATION: Synthetic

<400> SEQUENCE: 158
ggttgaggca ggtcagtttt tttttttttt t                             31

<210> SEQ ID NO 159
<211> LENGTH: 42
<212> TYPE: DNA
<213> ORGANISM: artificial sequence
<220> FEATURE:
<223> OTHER INFORMATION: Synthetic

<400> SEQUENCE: 159
tttttttttt tttttgatta agactcctta tccaaaagga at                 42

<210> SEQ ID NO 160
<211> LENGTH: 32
<212> TYPE: DNA
<213> ORGANISM: artificial sequence
<220> FEATURE:
<223> OTHER INFORMATION: Synthetic

<400> SEQUENCE: 160
tttttttttt tttttcttc gctattacaa tt                                   32

<210> SEQ ID NO 161
<211> LENGTH: 48
<212> TYPE: DNA
<213> ORGANISM: artificial sequence
<220> FEATURE:
<223> OTHER INFORMATION: Synthetic

<400> SEQUENCE: 161
tttttttttt tttttcttgc gggagaagcg catttttttt tttttttt                 48

<210> SEQ ID NO 162
<211> LENGTH: 50
<212> TYPE: DNA
<213> ORGANISM: artificial sequence
<220> FEATURE:
<223> OTHER INFORMATION: Synthetic

<400> SEQUENCE: 162
tttttttttt ttttgggaat tagagaaaca atgaattttt tttttttttt              50

<210> SEQ ID NO 163
<211> LENGTH: 38
<212> TYPE: DNA
<213> ORGANISM: artificial sequence
<220> FEATURE:
<223> OTHER INFORMATION: Synthetic

<400> SEQUENCE: 163
tcagactgac agaatcaagt tgttttttt tttttttt                             38

<210> SEQ ID NO 164
<211> LENGTH: 41
<212> TYPE: DNA
<213> ORGANISM: artificial sequence
<220> FEATURE:
<223> OTHER INFORMATION: Synthetic

<400> SEQUENCE: 164
tttttttttt tttttggtcg aggtgccgta aagcagcacg t                        41

<210> SEQ ID NO 165
<211> LENGTH: 48
<212> TYPE: DNA
<213> ORGANISM: artificial sequence
<220> FEATURE:
<223> OTHER INFORMATION: Synthetic

<400> SEQUENCE: 165
tttttttttt tttttttaa tcatttacca gactttttt tttttttt                   48

<210> SEQ ID NO 166
<211> LENGTH: 50
<212> TYPE: DNA
<213> ORGANISM: artificial sequence
<220> FEATURE:
<223> OTHER INFORMATION: Synthetic

<400> SEQUENCE: 166
tttttttttt tttcattctg gccaaattcg acaactcttt tttttttttt              50

<210> SEQ ID NO 167

<211> LENGTH: 27
<212> TYPE: DNA
<213> ORGANISM: artificial sequence
<220> FEATURE:
<223> OTHER INFORMATION: Synthetic

<400> SEQUENCE: 167 ttttttttttt tttttaccgg atattca                                           27

<210> SEQ ID NO 168
<211> LENGTH: 48
<212> TYPE: DNA
<213> ORGANISM: artificial sequence
<220> FEATURE:
<223> OTHER INFORMATION: Synthetic

<400> SEQUENCE: 168
tttttttttt tttttagac gggaaactgg catttttttt tttttttt                      48

<210> SEQ ID NO 169
<211> LENGTH: 41
<212> TYPE: DNA
<213> ORGANISM: artificial sequence
<220> FEATURE:
<223> OTHER INFORMATION: Synthetic

<400> SEQUENCE: 169
tttttttttt tttttcagca agcggtccac gctgcccaaa t                            41

<210> SEQ ID NO 170
<211> LENGTH: 27
<212> TYPE: DNA
<213> ORGANISM: artificial sequence
<220> FEATURE:
<223> OTHER INFORMATION: Synthetic

<400> SEQUENCE: 170
ctgagagagt tgtttttttt tttttttt                                           27

<210> SEQ ID NO 171
<211> LENGTH: 31
<212> TYPE: DNA
<213> ORGANISM: artificial sequence
<220> FEATURE:
<223> OTHER INFORMATION: Synthetic

<400> SEQUENCE: 171
caatgacaac aaccattttt ttttttttt t                                        31

<210> SEQ ID NO 172
<211> LENGTH: 36
<212> TYPE: DNA
<213> ORGANISM: artificial sequence
<220> FEATURE:
<223> OTHER INFORMATION: Synthetic

<400> SEQUENCE: 172
tttttttttt tttttgaga gatctacaag gagagg                                   36

<210> SEQ ID NO 173
<211> LENGTH: 31
<212> TYPE: DNA
<213> ORGANISM: artificial sequence
<220> FEATURE:
<223> OTHER INFORMATION: Synthetic

<400> SEQUENCE: 173
tcaccagtac aaactatttt tttttttttt t					31

<210> SEQ ID NO 174
<211> LENGTH: 50
<212> TYPE: DNA
<213> ORGANISM: artificial sequence
<220> FEATURE:
<223> OTHER INFORMATION: Synthetic

<400> SEQUENCE: 174
tttttttttt tttggcaatt catcaaatta ttcatttttt tttttttttt					50

<210> SEQ ID NO 175
<211> LENGTH: 40
<212> TYPE: DNA
<213> ORGANISM: artificial sequence
<220> FEATURE:
<223> OTHER INFORMATION: Synthetic

<400> SEQUENCE: 175
taaagttacc gcactcatcg agaactttt tttttttttt					40

<210> SEQ ID NO 176
<211> LENGTH: 31
<212> TYPE: DNA
<213> ORGANISM: artificial sequence
<220> FEATURE:
<223> OTHER INFORMATION: Synthetic

<400> SEQUENCE: 176
tttttttttt tttttcaccc tcagaaccgc c					31

<210> SEQ ID NO 177
<211> LENGTH: 50
<212> TYPE: DNA
<213> ORGANISM: artificial sequence
<220> FEATURE:
<223> OTHER INFORMATION: Synthetic

<400> SEQUENCE: 177
tttttttttt tttaggttta acgtcaatat atgtgagttt tttttttttt					50

<210> SEQ ID NO 178
<211> LENGTH: 27
<212> TYPE: DNA
<213> ORGANISM: artificial sequence
<220> FEATURE:
<223> OTHER INFORMATION: Synthetic

<400> SEQUENCE: 178
ccacacaaca tacgttttt ttttttt					27

<210> SEQ ID NO 179
<211> LENGTH: 48
<212> TYPE: DNA
<213> ORGANISM: artificial sequence
<220> FEATURE:
<223> OTHER INFORMATION: Synthetic

<400> SEQUENCE: 179
tttttttttt tttttgctag ggcgagtaaa agatttttt tttttttt					48

<210> SEQ ID NO 180
<211> LENGTH: 42
<212> TYPE: DNA

```
<213> ORGANISM: artificial sequence
<220> FEATURE:
<223> OTHER INFORMATION: Synthetic

<400> SEQUENCE: 180 ttttttttttt tttttagttg attcccaatt ctgcgaacct ca                42

<210> SEQ ID NO 181
<211> LENGTH: 40
<212> TYPE: DNA
<213> ORGANISM: artificial sequence
<220> FEATURE:
<223> OTHER INFORMATION: Synthetic

<400> SEQUENCE: 181
ttatttagag cctaatttgc cagttttttt tttttttttt                    40

<210> SEQ ID NO 182
<211> LENGTH: 24
<212> TYPE: DNA
<213> ORGANISM: artificial sequence
<220> FEATURE:
<223> OTHER INFORMATION: Synthetic

<400> SEQUENCE: 182 ttttttttttt tttttacggc ggat                                    24

<210> SEQ ID NO 183
<211> LENGTH: 48
<212> TYPE: DNA
<213> ORGANISM: artificial sequence
<220> FEATURE:
<223> OTHER INFORMATION: Synthetic

<400> SEQUENCE: 183 ttttttttttt tttttatatg cgttaagtcc tgattttttt tttttttt          48

<210> SEQ ID NO 184
<211> LENGTH: 31
<212> TYPE: DNA
<213> ORGANISM: artificial sequence
<220> FEATURE:
<223> OTHER INFORMATION: Synthetic

<400> SEQUENCE: 184 ttttttttttt tttttacgat tggccttgat a                            31

<210> SEQ ID NO 185
<211> LENGTH: 31
<212> TYPE: DNA
<213> ORGANISM: artificial sequence
<220> FEATURE:
<223> OTHER INFORMATION: Synthetic

<400> SEQUENCE: 185 ttttttttttt tttttcaacg cctgtagcat t                            31

<210> SEQ ID NO 186
<211> LENGTH: 48
<212> TYPE: DNA
<213> ORGANISM: artificial sequence
<220> FEATURE:
<223> OTHER INFORMATION: Synthetic

<400> SEQUENCE: 186 ttttttttttt tttttggctt tgagccggaa cgattttttt tttttttt          48
```

<210> SEQ ID NO 187
<211> LENGTH: 28
<212> TYPE: DNA
<213> ORGANISM: artificial sequence
<220> FEATURE:
<223> OTHER INFORMATION: Synthetic

<400> SEQUENCE: 187
tttttttttt tttttaagca agccgttt                                    28

<210> SEQ ID NO 188
<211> LENGTH: 50
<212> TYPE: DNA
<213> ORGANISM: artificial sequence
<220> FEATURE:
<223> OTHER INFORMATION: Synthetic

<400> SEQUENCE: 188
tttttttttt tttatgtgta ggtaagtacc ccggttgttt tttttttttt            50

<210> SEQ ID NO 189
<211> LENGTH: 34
<212> TYPE: DNA
<213> ORGANISM: artificial sequence
<220> FEATURE:
<223> OTHER INFORMATION: Synthetic

<400> SEQUENCE: 189
atcgtcataa atattcattt tttttttttt tttt                             34

<210> SEQ ID NO 190
<211> LENGTH: 28
<212> TYPE: DNA
<213> ORGANISM: artificial sequence
<220> FEATURE:
<223> OTHER INFORMATION: Synthetic

<400> SEQUENCE: 190
tttttttttt tttttgttaa tttcatct                                    28

<210> SEQ ID NO 191
<211> LENGTH: 50
<212> TYPE: DNA
<213> ORGANISM: artificial sequence
<220> FEATURE:
<223> OTHER INFORMATION: Synthetic

<400> SEQUENCE: 191
tttttttttt tttgtattaa atcctgcgta gattttcttt tttttttttt            50

<210> SEQ ID NO 192
<211> LENGTH: 39
<212> TYPE: DNA
<213> ORGANISM: artificial sequence
<220> FEATURE:
<223> OTHER INFORMATION: Synthetic

<400> SEQUENCE: 192
gccatataag agcaagccag cccgacttga gccatggtt                        39

<210> SEQ ID NO 193
<211> LENGTH: 50
<212> TYPE: DNA
<213> ORGANISM: artificial sequence
<220> FEATURE:

<223> OTHER INFORMATION: Synthetic

<400> SEQUENCE: 193
gtagctagta ccaaaaacat tcataaagct aaatcggttt tttttttttt                50

<210> SEQ ID NO 194
<211> LENGTH: 27
<212> TYPE: DNA
<213> ORGANISM: artificial sequence
<220> FEATURE:
<223> OTHER INFORMATION: Synthetic

<400> SEQUENCE: 194
ataacgtgct tttttttttt ttttttt                                         27

<210> SEQ ID NO 195
<211> LENGTH: 48
<212> TYPE: DNA
<213> ORGANISM: artificial sequence
<220> FEATURE:
<223> OTHER INFORMATION: Synthetic

<400> SEQUENCE: 195
tttttttttt tttttaaaat accgaacgaa ccaccagtga gaattaac                  48

<210> SEQ ID NO 196
<211> LENGTH: 27
<212> TYPE: DNA
<213> ORGANISM: artificial sequence
<220> FEATURE:
<223> OTHER INFORMATION: Synthetic

<400> SEQUENCE: 196
tttttttttt tttttacaaa ataaaca                                         27

<210> SEQ ID NO 197
<211> LENGTH: 48
<212> TYPE: DNA
<213> ORGANISM: artificial sequence
<220> FEATURE:
<223> OTHER INFORMATION: Synthetic

<400> SEQUENCE: 197
tttttttttt tttttacaag aaaaacctcc cgatttttttt tttttttt                 48

<210> SEQ ID NO 198
<211> LENGTH: 48
<212> TYPE: DNA
<213> ORGANISM: artificial sequence
<220> FEATURE:
<223> OTHER INFORMATION: Synthetic

<400> SEQUENCE: 198
tttttttttt tttttgacga taaaaagatt aagtttttt tttttttt                   48

<210> SEQ ID NO 199
<211> LENGTH: 50
<212> TYPE: DNA
<213> ORGANISM: artificial sequence
<220> FEATURE:
<223> OTHER INFORMATION: Synthetic

<400> SEQUENCE: 199
tttttttttt tttcaattac ctgagtatca aaatcatttt tttttttttt                50

```
<210> SEQ ID NO 200
<211> LENGTH: 34
<212> TYPE: DNA
<213> ORGANISM: artificial sequence
<220> FEATURE:
<223> OTHER INFORMATION: Synthetic

<400> SEQUENCE: 200
ggtacggcca gtgccaagct ttttttttt tttt                              34

<210> SEQ ID NO 201
<211> LENGTH: 50
<212> TYPE: DNA
<213> ORGANISM: artificial sequence
<220> FEATURE:
<223> OTHER INFORMATION: Synthetic

<400> SEQUENCE: 201
tttttttttt ttttgaataa ccttgaaata tattttattt tttttttttt            50

<210> SEQ ID NO 202
<211> LENGTH: 27
<212> TYPE: DNA
<213> ORGANISM: artificial sequence
<220> FEATURE:
<223> OTHER INFORMATION: Synthetic

<400> SEQUENCE: 202
cactaaaaca ctttttttt ttttttt                                      27

<210> SEQ ID NO 203
<211> LENGTH: 48
<212> TYPE: DNA
<213> ORGANISM: artificial sequence
<220> FEATURE:
<223> OTHER INFORMATION: Synthetic

<400> SEQUENCE: 203
tttttttttt ttttttaacc aatatgggaa caatttttt tttttttt               48

<210> SEQ ID NO 204
<211> LENGTH: 34
<212> TYPE: DNA
<213> ORGANISM: artificial sequence
<220> FEATURE:
<223> OTHER INFORMATION: Synthetic

<400> SEQUENCE: 204
tacgtcacaa tcaatagaat tttttttttt tttt                             34

<210> SEQ ID NO 205
<211> LENGTH: 34
<212> TYPE: DNA
<213> ORGANISM: artificial sequence
<220> FEATURE:
<223> OTHER INFORMATION: Synthetic

<400> SEQUENCE: 205
tttttttttt tttttagaaa gattcatcag ttga                             34

<210> SEQ ID NO 206
<211> LENGTH: 50
<212> TYPE: DNA
<213> ORGANISM: artificial sequence
<220> FEATURE:
<223> OTHER INFORMATION: Synthetic
```

<400> SEQUENCE: 206
tttttttttt tttgtggcat caattaatgc ctgagtattt ttttttttt     50

<210> SEQ ID NO 207
<211> LENGTH: 48
<212> TYPE: DNA
<213> ORGANISM: artificial sequence
<220> FEATURE:
<223> OTHER INFORMATION: Synthetic

<400> SEQUENCE: 207
tttttttttt tttttttgca tgcctgcatt aatttttttt tttttttt     48

<210> SEQ ID NO 208
<211> LENGTH: 41
<212> TYPE: DNA
<213> ORGANISM: artificial sequence
<220> FEATURE:
<223> OTHER INFORMATION: Synthetic

<400> SEQUENCE: 208
ccagcgaaag agtaatcttg acaagatttt ttttttttt t            41

<210> SEQ ID NO 209
<211> LENGTH: 34
<212> TYPE: DNA
<213> ORGANISM: artificial sequence
<220> FEATURE:
<223> OTHER INFORMATION: Synthetic

<400> SEQUENCE: 209
tttttttttt tttttgaatc cccctcaaat gctt                    34

<210> SEQ ID NO 210
<211> LENGTH: 31
<212> TYPE: DNA
<213> ORGANISM: artificial sequence
<220> FEATURE:
<223> OTHER INFORMATION: Synthetic

<400> SEQUENCE: 210
agaggctgag actccttttt tttttttttt t                       31

<210> SEQ ID NO 211
<211> LENGTH: 41
<212> TYPE: DNA
<213> ORGANISM: artificial sequence
<220> FEATURE:
<223> OTHER INFORMATION: Synthetic

<400> SEQUENCE: 211
acaaacacag agatacatcg ccattatttt ttttttttt t            41

<210> SEQ ID NO 212
<211> LENGTH: 31
<212> TYPE: DNA
<213> ORGANISM: artificial sequence
<220> FEATURE:
<223> OTHER INFORMATION: Synthetic

<400> SEQUENCE: 212
tttttttttt tttttcaaga gaaggattag g                       31

<210> SEQ ID NO 213
<211> LENGTH: 50

```
<212> TYPE: DNA
<213> ORGANISM: artificial sequence
<220> FEATURE:
<223> OTHER INFORMATION: Synthetic

<400> SEQUENCE: 213
tttttttttt tttgaattga ggaagttatc agatgatttt tttttttttt              50

<210> SEQ ID NO 214
<211> LENGTH: 27
<212> TYPE: DNA
<213> ORGANISM: artificial sequence
<220> FEATURE:
<223> OTHER INFORMATION: Synthetic

<400> SEQUENCE: 214
cagaacaata tttttttttt ttttttt                                       27

<210> SEQ ID NO 215
<211> LENGTH: 39
<212> TYPE: DNA
<213> ORGANISM: artificial sequence
<220> FEATURE:
<223> OTHER INFORMATION: Synthetic

<400> SEQUENCE: 215
tttttttttt tttagccgga agcataaagt gtcctggcc                          39

<210> SEQ ID NO 216
<211> LENGTH: 50
<212> TYPE: DNA
<213> ORGANISM: artificial sequence
<220> FEATURE:
<223> OTHER INFORMATION: Synthetic

<400> SEQUENCE: 216
tgaccgtttc tccgggaacg caaatcagct cattttttttt tttttttttt             50

<210> SEQ ID NO 217
<211> LENGTH: 31
<212> TYPE: DNA
<213> ORGANISM: artificial sequence
<220> FEATURE:
<223> OTHER INFORMATION: Synthetic

<400> SEQUENCE: 217
tttttttttt ttttggtaa taagttttaa c                                   31

<210> SEQ ID NO 218
<211> LENGTH: 50
<212> TYPE: DNA
<213> ORGANISM: artificial sequence
<220> FEATURE:
<223> OTHER INFORMATION: Synthetic

<400> SEQUENCE: 218
tttttttttt ttttgtctgt ccataataaa agggatttttt tttttttttt             50

<210> SEQ ID NO 219
<211> LENGTH: 41
<212> TYPE: DNA
<213> ORGANISM: artificial sequence
<220> FEATURE:
<223> OTHER INFORMATION: Synthetic

<400> SEQUENCE: 219
```

-continued ttttttttttt tttttcctcg ttagaatcag agcgtaatat c    41

<210> SEQ ID NO 220
<211> LENGTH: 34
<212> TYPE: DNA
<213> ORGANISM: artificial sequence
<220> FEATURE:
<223> OTHER INFORMATION: Synthetic

<400> SEQUENCE: 220
aattgctcct tttgataagt tttttttttt tttt    34

<210> SEQ ID NO 221
<211> LENGTH: 48
<212> TYPE: DNA
<213> ORGANISM: artificial sequence
<220> FEATURE:
<223> OTHER INFORMATION: Synthetic

<400> SEQUENCE: 221
catcggacag ccctgctaaa caactttcaa cagtttttttt tttttttt    48

<210> SEQ ID NO 222
<211> LENGTH: 38
<212> TYPE: DNA
<213> ORGANISM: artificial sequence
<220> FEATURE:
<223> OTHER INFORMATION: Synthetic

<400> SEQUENCE: 222 ttttttttttt tttttaaccg cctccctcag accagagc    38

<210> SEQ ID NO 223
<211> LENGTH: 40
<212> TYPE: DNA
<213> ORGANISM: artificial sequence
<220> FEATURE:
<223> OTHER INFORMATION: Synthetic

<400> SEQUENCE: 223
tctgacagag gcattttcga gccagttttt tttttttttt    40

<210> SEQ ID NO 224
<211> LENGTH: 41
<212> TYPE: DNA
<213> ORGANISM: artificial sequence
<220> FEATURE:
<223> OTHER INFORMATION: Synthetic

<400> SEQUENCE: 224 ttttttttttt tttttttttca gcggagttcc atgtcataag g    41

<210> SEQ ID NO 225
<211> LENGTH: 31
<212> TYPE: DNA
<213> ORGANISM: artificial sequence
<220> FEATURE:
<223> OTHER INFORMATION: Synthetic

<400> SEQUENCE: 225 ttttttttttt tttttcgccc acgcataacc g    31

<210> SEQ ID NO 226
<211> LENGTH: 48
<212> TYPE: DNA
<213> ORGANISM: artificial sequence

```
<220> FEATURE:
<223> OTHER INFORMATION: Synthetic

<400> SEQUENCE: 226
aattacttag gactaaatag caacggctac agatttttt tttttttt          48

<210> SEQ ID NO 227
<211> LENGTH: 27
<212> TYPE: DNA
<213> ORGANISM: artificial sequence
<220> FEATURE:
<223> OTHER INFORMATION: Synthetic

<400> SEQUENCE: 227 caagttttt ggttttttt tttttt                                    27

<210> SEQ ID NO 228
<211> LENGTH: 48
<212> TYPE: DNA
<213> ORGANISM: artificial sequence
<220> FEATURE:
<223> OTHER INFORMATION: Synthetic

<400> SEQUENCE: 228 tttttttt ttttccttt agcgcaccac cggttttt tttttttt              48

<210> SEQ ID NO 229
<211> LENGTH: 48
<212> TYPE: DNA
<213> ORGANISM: artificial sequence
<220> FEATURE:
<223> OTHER INFORMATION: Synthetic

<400> SEQUENCE: 229 tttttttt ttttgaatc ggccgagtgt tgtttttt tttttttt              48

<210> SEQ ID NO 230
<211> LENGTH: 25
<212> TYPE: DNA
<213> ORGANISM: artificial sequence
<220> FEATURE:
<223> OTHER INFORMATION: Synthetic

<400> SEQUENCE: 230 tttttttt tttcatcttt gaccc                                     25

<210> SEQ ID NO 231
<211> LENGTH: 50
<212> TYPE: DNA
<213> ORGANISM: artificial sequence
<220> FEATURE:
<223> OTHER INFORMATION: Synthetic

<400> SEQUENCE: 231 tttttttt tttataatca gaaaatcggt gcgggccttt tttttttt            50

<210> SEQ ID NO 232
<211> LENGTH: 31
<212> TYPE: DNA
<213> ORGANISM: artificial sequence
<220> FEATURE:
<223> OTHER INFORMATION: Synthetic

<400> SEQUENCE: 232
gatacaggag tgtactttt tttttttt t                               31
```

<210> SEQ ID NO 233
<211> LENGTH: 48
<212> TYPE: DNA
<213> ORGANISM: artificial sequence
<220> FEATURE:
<223> OTHER INFORMATION: Synthetic

<400> SEQUENCE: 233
tttttttttt tttttggcgc agacaatttc aactttttt tttttttt          48

<210> SEQ ID NO 234
<211> LENGTH: 31
<212> TYPE: DNA
<213> ORGANISM: artificial sequence
<220> FEATURE:
<223> OTHER INFORMATION: Synthetic

<400> SEQUENCE: 234
ggaggtttag taccgctttt tttttttttt t                            31

<210> SEQ ID NO 235
<211> LENGTH: 50
<212> TYPE: DNA
<213> ORGANISM: artificial sequence
<220> FEATURE:
<223> OTHER INFORMATION: Synthetic

<400> SEQUENCE: 235
tttttttttt tttaccgcca gccataacag ttgaaagttt tttttttttt        50

<210> SEQ ID NO 236
<211> LENGTH: 27
<212> TYPE: DNA
<213> ORGANISM: artificial sequence
<220> FEATURE:
<223> OTHER INFORMATION: Synthetic

<400> SEQUENCE: 236
tttttttttt tttttatagc aatagct                                 27

<210> SEQ ID NO 237
<211> LENGTH: 48
<212> TYPE: DNA
<213> ORGANISM: artificial sequence
<220> FEATURE:
<223> OTHER INFORMATION: Synthetic

<400> SEQUENCE: 237
aataagtttt gcaagcccaa taggggataa gtatcggatg actatact          48

<210> SEQ ID NO 238
<211> LENGTH: 45
<212> TYPE: DNA
<213> ORGANISM: artificial sequence
<220> FEATURE:
<223> OTHER INFORMATION: Synthetic

<400> SEQUENCE: 238
acatagctta catttaacaa taataacgtt gtgctactcc agttc             45

<210> SEQ ID NO 239
<211> LENGTH: 38
<212> TYPE: DNA
<213> ORGANISM: artificial sequence
<220> FEATURE:
<223> OTHER INFORMATION: Synthetic -continued

<400> SEQUENCE: 239 ccttttttgaa tggcgtcagt attgtgctac tccagttc                                38

<210> SEQ ID NO 240
<211> LENGTH: 38
<212> TYPE: DNA
<213> ORGANISM: artificial sequence
<220> FEATURE:
<223> OTHER INFORMATION: Synthetic

<400> SEQUENCE: 240
cgtaaccaat tcatcaacat tttgtgctac tccagttc                                38

<210> SEQ ID NO 241
<211> LENGTH: 42
<212> TYPE: DNA
<213> ORGANISM: artificial sequence
<220> FEATURE:
<223> OTHER INFORMATION: Synthetic

<400> SEQUENCE: 241
caccaaccga tattcattac cattattgtg ctactccagt tc                           42

<210> SEQ ID NO 242
<211> LENGTH: 38
<212> TYPE: DNA
<213> ORGANISM: artificial sequence
<220> FEATURE:
<223> OTHER INFORMATION: Synthetic

<400> SEQUENCE: 242
ccaccctcat tttcttgata tttgtgctac tccagttc                                38

<210> SEQ ID NO 243
<211> LENGTH: 38
<212> TYPE: DNA
<213> ORGANISM: artificial sequence
<220> FEATURE:
<223> OTHER INFORMATION: Synthetic

<400> SEQUENCE: 243
aactttgaaa gaggagaaac attgtgctac tccagttc                                38

<210> SEQ ID NO 244
<211> LENGTH: 38
<212> TYPE: DNA
<213> ORGANISM: artificial sequence
<220> FEATURE:
<223> OTHER INFORMATION: Synthetic

<400> SEQUENCE: 244
caaggcgcgc cattgccgga attgtgctac tccagttc                                38

<210> SEQ ID NO 245
<211> LENGTH: 38
<212> TYPE: DNA
<213> ORGANISM: artificial sequence
<220> FEATURE:
<223> OTHER INFORMATION: Synthetic

<400> SEQUENCE: 245
catagccccc ttaagtcacc attgtgctac tccagttc                                38

<210> SEQ ID NO 246

```
<211> LENGTH: 45
<212> TYPE: DNA
<213> ORGANISM: artificial sequence
<220> FEATURE:
<223> OTHER INFORMATION: Synthetic

<400> SEQUENCE: 246
tttccctgaa ttaccttttt tacctttttt gtgctactcc agttc            45

<210> SEQ ID NO 247
<211> LENGTH: 38
<212> TYPE: DNA
<213> ORGANISM: artificial sequence
<220> FEATURE:
<223> OTHER INFORMATION: Synthetic

<400> SEQUENCE: 247
aacggtgtac agactgaata attgtgctac tccagttc                    38

<210> SEQ ID NO 248
<211> LENGTH: 45
<212> TYPE: DNA
<213> ORGANISM: artificial sequence
<220> FEATURE:
<223> OTHER INFORMATION: Synthetic

<400> SEQUENCE: 248
gattcgcggg ttagaaccta ccatttttgtt gtgctactcc agttc           45

<210> SEQ ID NO 249
<211> LENGTH: 33
<212> TYPE: DNA
<213> ORGANISM: artificial sequence
<220> FEATURE:
<223> OTHER INFORMATION: Synthetic

<400> SEQUENCE: 249
agagtaggat ttcgccaaca tgttttaaaa acc                         33

<210> SEQ ID NO 250
<211> LENGTH: 33
<212> TYPE: DNA
<213> ORGANISM: artificial sequence
<220> FEATURE:
<223> OTHER INFORMATION: Synthetic

<400> SEQUENCE: 250
acggtgacct gtttagctga atataatgcc aac                         33

<210> SEQ ID NO 251
<211> LENGTH: 33
<212> TYPE: DNA
<213> ORGANISM: artificial sequence
<220> FEATURE:
<223> OTHER INFORMATION: Synthetic

<400> SEQUENCE: 251
cgtagcaatt tagttctaaa gtacggtgtt tta                         33

<210> SEQ ID NO 252
<211> LENGTH: 43
<212> TYPE: DNA
<213> ORGANISM: artificial sequence
<220> FEATURE:
<223> OTHER INFORMATION: Synthetic

<400> SEQUENCE: 252
```
gcttaatgcg ttaaatgtaa atgctgatct tgaaatgagc gtt        43

<210> SEQ ID NO 253
<211> LENGTH: 43
<212> TYPE: DNA
<213> ORGANISM: artificial sequence
<220> FEATURE:
<223> OTHER INFORMATION: Synthetic

<400> SEQUENCE: 253
aagccaacgg aatctaggtt gggttatata gattaagcaa ctg        43

<210> SEQ ID NO 254
<211> LENGTH: 43
<212> TYPE: DNA
<213> ORGANISM: artificial sequence
<220> FEATURE:
<223> OTHER INFORMATION: Synthetic

<400> SEQUENCE: 254
tttaacaacc gacccaatcg caagacaaaa ttaatctcac tgc        43

<210> SEQ ID NO 255
<211> LENGTH: 43
<212> TYPE: DNA
<213> ORGANISM: artificial sequence
<220> FEATURE:
<223> OTHER INFORMATION: Synthetic

<400> SEQUENCE: 255
tttaggccta aattgagaaa acttttttcct tctgttccta gat       43

<210> SEQ ID NO 256
<211> LENGTH: 33
<212> TYPE: DNA
<213> ORGANISM: artificial sequence
<220> FEATURE:
<223> OTHER INFORMATION: Synthetic

<400> SEQUENCE: 256
ggtttttaaa acatgttggc gaaatcctac tct        33

<210> SEQ ID NO 257
<211> LENGTH: 33
<212> TYPE: DNA
<213> ORGANISM: artificial sequence
<220> FEATURE:
<223> OTHER INFORMATION: Synthetic

<400> SEQUENCE: 257
gttggcatta tattcagcta aacaggtcac cgt        33

<210> SEQ ID NO 258
<211> LENGTH: 33
<212> TYPE: DNA
<213> ORGANISM: artificial sequence
<220> FEATURE:
<223> OTHER INFORMATION: Synthetic

<400> SEQUENCE: 258
taaaacaccg tactttagaa ctaaattgct acg        33

<210> SEQ ID NO 259
<211> LENGTH: 43
<212> TYPE: DNA

```
<213> ORGANISM: artificial sequence
<220> FEATURE:
<223> OTHER INFORMATION: Synthetic

<400> SEQUENCE: 259
aacgctcatt tcaagatcag catttacatt taacgcatta agc                           43

<210> SEQ ID NO 260
<211> LENGTH: 43
<212> TYPE: DNA
<213> ORGANISM: artificial sequence
<220> FEATURE:
<223> OTHER INFORMATION: Synthetic

<400> SEQUENCE: 260
cagttgctta atctatataa cccaacctag attccgttgg ctt                           43

<210> SEQ ID NO 261
<211> LENGTH: 43
<212> TYPE: DNA
<213> ORGANISM: artificial sequence
<220> FEATURE:
<223> OTHER INFORMATION: Synthetic

<400> SEQUENCE: 261
gcagtgagat taattttgtc ttgcgattgg gtcggttgtt aaa                           43

<210> SEQ ID NO 262
<211> LENGTH: 43
<212> TYPE: DNA
<213> ORGANISM: artificial sequence
<220> FEATURE:
<223> OTHER INFORMATION: Synthetic

<400> SEQUENCE: 262
atctaggaac agaaggaaaa agttttctca atttaggcct aaa                           43

<210> SEQ ID NO 263
<211> LENGTH: 63
<212> TYPE: DNA
<213> ORGANISM: artificial sequence
<220> FEATURE:
<223> OTHER INFORMATION: Synthetic

<400> SEQUENCE: 263
tggggcgcga gctgaaaagt actcagggca ctgcaagcaa ttgtggtccc aatgggctga         60
gta                                                                      63

<210> SEQ ID NO 264
<211> LENGTH: 79
<212> TYPE: DNA
<213> ORGANISM: artificial sequence
<220> FEATURE:
<223> OTHER INFORMATION: Synthetic

<400> SEQUENCE: 264
tgatgagcgt ggatgatact cagcccattg ggttttttttt tttttttttt tttttttttt        60
aggtcatttt tgcggatgg                                                     79

<210> SEQ ID NO 265
<211> LENGTH: 67
<212> TYPE: DNA
<213> ORGANISM: artificial sequence
<220> FEATURE:
<223> OTHER INFORMATION: Synthetic
```

<400> SEQUENCE: 265
atacaaaaag cctgtttagt atctactcag ggcactgcaa gcaattgtgg tcccaatggg     60
ctgagta                                                              67

<210> SEQ ID NO 266
<211> LENGTH: 63
<212> TYPE: DNA
<213> ORGANISM: artificial sequence
<220> FEATURE:
<223> OTHER INFORMATION: Synthetic

<400> SEQUENCE: 266
tactcagccc attgggtttt ttttttttt ttttttttt ttttaggtct gagagactac      60
ctt                                                                  63

<210> SEQ ID NO 267
<211> LENGTH: 63
<212> TYPE: DNA
<213> ORGANISM: artificial sequence
<220> FEATURE:
<223> OTHER INFORMATION: Synthetic

<400> SEQUENCE: 267
tggggcgcga gctgaaaaga taccagtcta ttcaattggg cccgtccgta tggtgggtgt     60
gct                                                                  63

<210> SEQ ID NO 268
<211> LENGTH: 63
<212> TYPE: DNA
<213> ORGANISM: artificial sequence
<220> FEATURE:
<223> OTHER INFORMATION: Synthetic

<400> SEQUENCE: 268
agcacaccca ccatactttt ttttttttt ttttttttt ttttaggtca ttttgcgga       60 tgg                                                                  63

<210> SEQ ID NO 269
<211> LENGTH: 67
<212> TYPE: DNA
<213> ORGANISM: artificial sequence
<220> FEATURE:
<223> OTHER INFORMATION: Synthetic

<400> SEQUENCE: 269
atacaaaaag cctgtttagt atcataccag tctattcaat tgggcccgtc cgtatggtgg     60
gtgtgct                                                              67

<210> SEQ ID NO 270
<211> LENGTH: 79
<212> TYPE: DNA
<213> ORGANISM: artificial sequence
<220> FEATURE:
<223> OTHER INFORMATION: Synthetic

<400> SEQUENCE: 270
tgatgagcat ggcatcagca cacccaccat actttttttt ttttttttt ttttttttt      60 aggtctgaga gactacctt                                                 79

<210> SEQ ID NO 271

```
<211> LENGTH: 63
<212> TYPE: DNA
<213> ORGANISM: artificial sequence
<220> FEATURE:
<223> OTHER INFORMATION: Synthetic

<400> SEQUENCE: 271
tggggcgcga gctgaaaagt actcagggca ctgcaagcaa ttgtggtccc aatgggctga     60
gta                                                                  63

<210> SEQ ID NO 272
<211> LENGTH: 71
<212> TYPE: DNA
<213> ORGANISM: artificial sequence
<220> FEATURE:
<223> OTHER INFORMATION: Synthetic

<400> SEQUENCE: 272
acctagtgta ctcagcccat tgggttttt tttttttttt tttttttttt ttaggtcatt     60
tttgcggatg g                                                         71

<210> SEQ ID NO 273
<211> LENGTH: 67
<212> TYPE: DNA
<213> ORGANISM: artificial sequence
<220> FEATURE:
<223> OTHER INFORMATION: Synthetic

<400> SEQUENCE: 273
atacaaaaag cctgtttagt atcataccag tctattcaat tgggcccgtc cgtatggtgg    60
gtgtgct                                                              67

<210> SEQ ID NO 274
<211> LENGTH: 71
<212> TYPE: DNA
<213> ORGANISM: artificial sequence
<220> FEATURE:
<223> OTHER INFORMATION: Synthetic

<400> SEQUENCE: 274
tacggagtag cacacccacc atactttttt tttttttttt tttttttttt ttaggtctga    60
gagactacct t                                                         71

<210> SEQ ID NO 275
<211> LENGTH: 48
<212> TYPE: DNA
<213> ORGANISM: artificial sequence
<220> FEATURE:
<223> OTHER INFORMATION: Synthetic

<400> SEQUENCE: 275
aagtatggtg ggtgtgctga tgccattttt tagtatagtc atccgata                 48

<210> SEQ ID NO 276
<211> LENGTH: 48
<212> TYPE: DNA
<213> ORGANISM: artificial sequence
<220> FEATURE:
<223> OTHER INFORMATION: Synthetic

<400> SEQUENCE: 276
aacccaatgg gctgagtatc atccactttt tagtatagtc atccgata                 48
```

```
<210> SEQ ID NO 277
<211> LENGTH: 48
<212> TYPE: DNA
<213> ORGANISM: artificial sequence
<220> FEATURE:
<223> OTHER INFORMATION: Synthetic

<400> SEQUENCE: 277
aagtatggtg ggtgtgctac tccgtatttt tagtatagtc atccgata                    48

<210> SEQ ID NO 278
<211> LENGTH: 52
<212> TYPE: DNA
<213> ORGANISM: artificial sequence
<220> FEATURE:
<223> OTHER INFORMATION: Synthetic

<400> SEQUENCE: 278
cccaatgggc tgagtatcat ccacgctcat cattttgaa ctggagtagc ac                52

<210> SEQ ID NO 279
<211> LENGTH: 52
<212> TYPE: DNA
<213> ORGANISM: artificial sequence
<220> FEATURE:
<223> OTHER INFORMATION: Synthetic

<400> SEQUENCE: 279
gtatggtggg tgtgctgatg ccatgctcat cattttgaa ctggagtagc ac                52

<210> SEQ ID NO 280
<211> LENGTH: 15
<212> TYPE: DNA
<213> ORGANISM: artificial sequence
<220> FEATURE:
<223> OTHER INFORMATION: Synthetic

<400> SEQUENCE: 280
gaactggagt agcac                                                        15

<210> SEQ ID NO 281
<211> LENGTH: 61
<212> TYPE: DNA
<213> ORGANISM: artificial sequence
<220> FEATURE:
<223> OTHER INFORMATION: Synthetic

<400> SEQUENCE: 281
cgtaaatttt ggcgtttttt tttttttttt tttttttttt ttaggtcatt tttgcggatg       60
g                                                                       61

<210> SEQ ID NO 282
<211> LENGTH: 58
<212> TYPE: DNA
<213> ORGANISM: artificial sequence
<220> FEATURE:
<223> OTHER INFORMATION: Synthetic

<400> SEQUENCE: 282 aaatttggc gttttttttt tttttttttt ttttttttta ggtcatttt gcggatgg          58

<210> SEQ ID NO 283
<211> LENGTH: 69
<212> TYPE: DNA
<213> ORGANISM: artificial sequence
```

```
<220> FEATURE:
<223> OTHER INFORMATION: Synthetic

<400> SEQUENCE: 283
tggggcgcga gctgaaaagt ttttttttt ttttttttt tttttttcgc caatatttac    60
gtgctgcta                                                          69

<210> SEQ ID NO 284
<211> LENGTH: 22
<212> TYPE: RNA
<213> ORGANISM: Artificial Sequence
<220> FEATURE:
<223> OTHER INFORMATION: Synthetic

<400> SEQUENCE: 284
uagcagcacg uaaauauugg cg                                           22
```

//NON-IMMUNOGENIC AND NUCLEASE RESISTANT NUCLEIC ACID ORIGAMI DEVICES AND COMPOSITIONS THEREOF

FIELD OF THE INVENTION

The present invention relates in general to non-immunogenic and nuclease resistant molecular origami devices and uses thereof.

BACKGROUND OF THE INVENTION

Since its introduction several years ago (Rothemund, 2006), scaffolded DNA origami has emerged as a powerful and elegant approach for bottom-up fabrication of complex shapes at the nanoscale. Shih, Douglas and others have extended DNA origami from 2D to 3D, and enhanced it with an open-source computer-aided design (CAD) tool, caDNAno (Dietz et al., 2009; Douglas et al., 2009a; Douglas et al., 2009b), enabling a remarkably diverse array of shapes that have been used for various applications, including imaging (Jungmann et al., 2012; Jungmann et al., 2010; Steinhauer et al., 2009), potential therapeutics (Douglas et al., 2012; Schuller et al., 2011), and metamaterials (Kuzyk et al., 2012; Bell et al., 2012; Schreibe et al., 2011).

WO 2012/061719 and Douglas et al. (2012), herein incorporated by reference as if fully described herein, disclose a DNA origami device useful in the targeted delivery of biologically active entities to specific cell populations.

SUMMARY OF INVENTION

In this invention, we describe an improved nucleic acid origami platform providing functional, stable, safe, non-immunogenic, and remote controllable therapeutic nanodevices. The platform also provide the means to provide a cargo in a ligand concentration dependent manner, control the activity of the devices by closing them at predetermined conditions, separately control multiple types of cargo, extend the shelf life of molecules such as drugs, vaccines, proteins, growth factors, cytokines, RNA molecules etc., and a tunable system to prevent drug tachyphylaxis by suppressing the endocytosis of drug-bound receptors from the cell surface. The platform is based on methods for modifying DNA origami devices by the addition of small molecule chemicals, peptides or large proteins, additional nucleic acid molecules, inorganic quantum dots, nanocrystals or nanoparticles, liposomes, polysaccharides, polymers, carbon nanotubes, and additional materials. The methods can also include enzymatic or non-enzymatic modification of the composition and structure of the DNA from which the device is made, such as methylation, acetylation, hydroxylation, fixation by chemical means, coating, etc. Finally, the platform can be achieved by designing the DNA origami device to be made of DNA that does not include certain motifs such as CpG, AT-rich regions etc.

In one aspect, the present invention provides a nucleic acid origami device comprising a scaffold strand and a plurality of staple strands, having the structure A, B, C or D, wherein:

in the structure A: (i) one of the staple strands comprises either (a) an aptamer domain capable of binding to a binding partner; (b) an oligonucleotide capable of binding a DNA binding protein; or (c) an oligoneucleotide attached to a nano-antenna capable of receiving an electromagnetic field, or one of the staple strands comprises an aptamer domain of (a) and another of the staple strands comprises an oligonucleotide of (b) or (c); (ii) another of the staple strands comprises a latch domain hybridized or bound to said aptamer domain of (a) or oligonucleotide of (b) or (c), the latch domain sequence being selected such that the aptamer domain of (a) is capable of binding to the binding partner such that the binding partner displaces the latch domain, or the latch domain is capable of hybridizing with an external oligonucleotide selected such that it displaces the aptamer domain; said latch domain is linked to a binding partner that is selected such that it has a first configuration under a first condition and a different second configuration under a different second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration; or the nano-antenna of (c), upon receipt of said electromagnetic field, undergoes inductive coupling and subsequent heating thereby displacing the latch domain from the oligonucleotide of (c); and (iii) the aptamer domain of (a) or the oligonucleotide of (b) or (c), and the latch domain, when hybridized or bound to one another, hold the device in a closed configuration; and the device transitions to an open configuration when said aptamer domain or oligonucleotide, and the latch domain, are not hybridized or bound to one another, in the structure B: (i) one of the staple strands comprises a first aptamer domain capable of binding to a first binding partner; (ii) another of the staple strands comprises a second aptamer domain capable of binding to a second binding partner; (iii) still another of the staple strands comprises a first latch domain hybridized to the first aptamer domain, the first latch domain sequence being selected such that the first aptamer domain is capable of binding to the first binding partner such that the first binding partner displaces the first latch domain, or the first latch domain is capable of hybridizing with an external oligonucleotide selected such that it displaces the aptamer domain; (iv) yet another of the staple strands comprises a second latch domain hybridized to the second aptamer domain, the second latch domain sequence being selected such that the second aptamer domain is capable of binding to the second binding partner such that the second binding partner displaces the second latch domain, or the second latch domain is capable of hybridizing with an external oligonucleotide selected such that it displaces the aptamer domain; and (v) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain, in the structure C: (i) two of the staple strands each comprises a latch domain linked to an oligonucleotide capable of hybridizing with an external oligonucleotide; and (ii) said nucleic acid origami device is in an open configuration when each one of the oligonucleotides capable of hybridizing with an external oligonucleotide is not hybridized to said external oligonucleotide; and the device transitions to a closed configuration when both of said oligonucleotides capable of hybridizing with an external oligonucleotide are hybridized to said external oligonucleotides, in the structure D; (i) another of the staple strands comprises an intrinsic oligonucleotide capable of hybridizing with an external soluble oligonucleotide and an oligonucleotide linked to a latch domain; (ii) two of the staple strands each comprises a latch domain linked to an oligonucleotide capable of hybridizing to each other and to the intrinsic oligonucleotide; (iii) each one of the oligonucleotides capable of hybridizing to each other and to the intrinsic oligonucleotide is hybridized to one intrinsic oligonucleotide and is selected such that the intrinsic oligonucleotide is capable of hybridizing to the external soluble oligonucleotide such that the external soluble oligonucleotide displaces the intrinsic oligonucleotide and the oligonucleotides capable of hybridizing to each other and to the intrinsic oligonucleotide hybridize to each other; and (iv) said nucleic acid origami device is in an open configuration when each one of the oligonucleotides capable of hybridizing to each other and to the intrinsic oligonucleotide is hybridized to said intrinsic oligonucleotide; and the device transitions to a closed configuration when each one of the oligonucleotides capable of hybridizing to each other and to the intrinsic oligonucleotide is not hybridized to said intrinsic oligonucleotide and is instead hybridized to each other, wherein said nucleic acid origami device is either alkylated, acylated or hydroxylated, or interacts with a compound capable of non-covalently binding to the major- or minor-groove of a double stranded nucleic acid, and therefore is resistant to nucleases, and/or said nucleic acid origami device lacks TLR9 recognition elements or the TLR9 recognition elements of said nucleic acid origami device are masked or modified and therefore said nucleic acid origami device is non-immunogenic.

In another aspect, the present invention is directed to a multimodal nucleic acid origami device comprising at least two inter-connected nucleic acid origami devices each independently as defined above.

In still another aspect, the present invention provides a nucleic acid origami device comprising a scaffold strand and a plurality of staple strands, wherein one of the staple strands comprises either an aptamer domain capable of binding a cell-membrane receptor or a ligand to said receptor, and (i) said nucleic acid origami device is either alkylated, acylated or hydroxylated, or interacts with a compound capable of non-covalently binding to the major- or minor-groove of a double stranded nucleic acid, and therefore is resistant to nucleases; and/or (ii) said nucleic acid origami device lacks TLR9 recognition elements or the TLR9 recognition elements of said nucleic acid origami device are masked or modified and therefore said nucleic acid origami device is non-immunogenic, wherein said nucleic acid origami device, when bound to said receptor at a surface of a cell, attenuates or prevents internalization of the receptor into said cell.

The present invention further provides use of a nucleic acid origami device as defined hereinabove, i.e., a nucleic acid origami device in which one of the staple strands comprises either an aptamer domain capable of binding a cell-membrane receptor or a ligand to said receptor, or a pharmaceutical composition thereof, for attenuating or preventing internalization of a cell membrane receptor into a cell.

In yet still another aspect, the present invention is directed to a hollow nucleic acid origami device having two open ends, said hollow nucleic acid origami device comprising a scaffold strand and a plurality of staple strands, wherein said hollow nucleic acid origami device has one sole configuration and said staple strands are selected such that the hollow nucleic acid origami device allows a biologically active agent having a maximum cross-section smaller than the inner cross-section of the hollow nucleic acid origami device to enter and exit the inner space of the hollow nucleic acid origami device, wherein said staple strands are further selected such that a predetermined equilibrium is established between the period of time said biologically active agent is present in said inner space of the hollow nucleic acid origami device and the period of time said biologically active agent is present outside said inner space of the hollow nucleic acid origami device.

In still other aspects, the present invention provides a pharmaceutical composition comprising nucleic acid origami devices having any one of the configurations defined above, and a pharmaceutically acceptable carrier.

The present invention further provides, in some aspects, methods for treating type I diabetes, type II diabetes, or hyperglycemia, comprising administering to an individual in need thereof a pharmaceutically effective amount of a nucleic acid origami device responsive to glucose levels as defined herein below.

Furthermore, the present invention provides methods for preparing a nucleic acid origami device as defined herein below that is either non-immunogenic, resistant to nucleases or both non-immunogenic and resistant to nucleases.

Thus, in one particular such aspect, the present invention provides a method for preparing a nucleic acid origami device as defined herein below that is non-immunogenic, said method comprising: (i) designing nucleic acid sequences composing the scaffold strand(s) and staple strands of said nucleic acid origami device or multimodal nucleic acid origami device such that said nucleic acid sequences either (a) do not form CpG islands on said nucleic acid origami device or multimodal nucleic acid origami device and therefore is non-immunogenic; or (b) do form CpG islands on nucleic acid origami device or multimodal nucleic acid origami device; (ii) synthesizing or otherwise obtaining said scaffold strand(s) and staple strands; (iii) contacting said scaffold and staple strands thereby forming a nucleic acid origami device or multimodal nucleic acid origami device; and (iv) masking said CpG islands, if present, by methylation, thereby rendering said nucleic acid origami device or multimodal nucleic acid origami device non-immunogenic.

In another particular such aspect, the present invention provides a method for preparing a nucleic acid origami device as defined herein below that is resistant to nucleases, said method comprising: (i) designing nucleic acid sequences composing the scaffold strand(s) and staple strands of said nucleic acid origami device or multimodal nucleic acid origami device such that said nucleic acid sequences optionally do not form CpG islands on said nucleic acid origami device or multimodal nucleic acid origami device; (ii) synthesizing or otherwise obtaining said scaffold strand(s) and staple strands; (iii) contacting said scaffold and staple strands thereby forming a nucleic acid origami device or multimodal nucleic acid origami device; (iv) masking said CpG islands, if present, and optionally adenine residues on said nucleic acid origami device or multimodal nucleic acid origami device, by methylation; and (v) optionally interacting said nucleic acid origami device or multimodal nucleic acid origami device with a compound capable of non-covalently binding to the major- or minor-groove of a double stranded nucleic acid, thereby obtaining said nucleic acid origami device or multimodal nucleic acid origami device that is resistant to nucleases.

In yet another particular such aspect, the present invention provides a method for preparing a nucleic acid origami device as defined herein below that is both non-immunogenic and resistant to nucleases, said method comprising: (i) designing nucleic acid sequences composing the scaffold strand(s) and staple strands of said nucleic acid origami device or multimodal nucleic acid origami device such that said nucleic acid sequences either (a) do not form CpG islands on said nucleic acid origami device or multimodal nucleic acid origami device and therefore is non-immunogenic; or (b) do form CpG islands on said nucleic acid origami device or multimodal nucleic acid origami device; (ii) synthesizing or otherwise obtaining said scaffold strand(s) and staple strands; (iii) contacting said scaffold and staple strands thereby forming a nucleic acid origami device or multimodal nucleic acid origami device; (iv) masking said CpG islands, if present, and optionally adenine residues on said nucleic acid origami device or multimodal nucleic acid origami device, by methylation; and (v) optionally interacting said nucleic acid origami device or multimodal nucleic acid origami device with a compound capable of non-covalently binding to the major- or minor-groove of a double stranded nucleic acid, thereby obtaining said nucleic acid origami device or multimodal nucleic acid origami device that is both non-immunogenic and resistant to nucleases.

BRIEF DESCRIPTION OF DRAWINGS

FIGS. 20A-D show the concept (A, B) and activity (C, D) of nanobots capable of closing in response to an external cue. A-B. An external oligonucleotide (a microRNA, miR16) displaces oligonucleotides linked to latch domains and frees them to hybridize to each other thereby closing the nanobot. C. FACS analysis shows decreased fluorescence with time as nanobots having an 8nt toehold close in response to the cue. A, 5 µM miR16; B, 10 µm miR16; D. FACS analysis shows decreased fluorescence with time as nanobots having an 1nt toehold close in response to the cue. A, 1 µm miR16; B, 5 µM miR16; C, 10 µM miR16. X-axis shows time in $10^{-1}$ second units. "r" represents ribonucleotides and "*" means phosphorothioate bonds.

DETAILED DESCRIPTION OF THE INVENTION

Figure 1A:
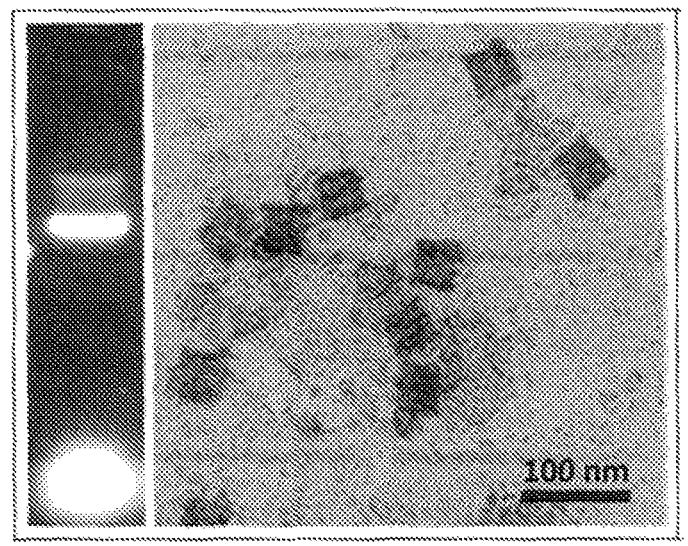
FIGS. 1A-B visualizes nanorobots by agarose-gel (left panels) and transmission electron microscopy (TEM) micrographs (right panels) of nanorobots obtained at different folding durations. Both samples of A and B were folded at 20 nM scaffold concentration, 200 nM staples concentration, 1×Tris/Acetic acid/EDTA (TAE) buffer, 10 mM $MgCl_2$. After folding, excess staples were removed using micon Ultra-0.5 mL 100K centrifugal filters (Millipore). (A) Folding duration is 80-60° C. at 2 min/° C. and 60-10° C. at 150 min/° C. (B) Folding duration is 80-60° C. at 5 min/° C., 60-10° C. at 75 min/° C.

Methylation is a central mechanism for epigenetic regulation of DNA activity and gene expression in a diverse range of organisms (Jones, 2012). In bacteria, DNA methylation protects the host DNA from its own restriction endonucleases, which recognize and destroy bacteriophage DNA. In an interesting analogy, methylation of vertebrate DNA protects it from recognition by its own immune system via Toll-like receptor 9 (TLR9) and autoantibody generation (Christensen et al., 2005; Hemmi et al., 2000). Hence, methylation seems to modify how DNA is interpreted by immune mechanisms.

The inventors of the present invention have unexpectedly found that a DNA origami device such that disclosed in WO 2012/061719, in spite of the very large size and unusual DNA structure present in this device, can be efficiently methylated and thereby made non-immunogenic and/or resistant to nucleases. It has further been found in accordance with the present invention that the device may be rendered resistant to nucleases by binding it to netropsin which binds to the minor groove of the DNA.

It has also been found in accordance with the present invention that the device as defined herein may be controlled from afar by attaching a metal nano-antenna capable of, upon receipt of said electromagnetic field, undergoing inductive coupling and subsequent heating thereby causing the device to undergo a conformational change from a closed to an open configuration. An additional finding according to the present invention is that the device may be equipped with a ligand-concentration sensitive protein, such as a glucokinase, that controls the opening or closure of the device according to, for example, ambient glucose concentration, and that such devices exhibiting insulin can activate insulin sensitive cells in a glucose concentration dependent manner. Still a further finding according to the present invention is that devices loaded with cytotoxic drugs can be designed so that they are inhibited in response to a damage cue leaking out from unintentionally damaged normal cells.

In one aspect, the present invention thus provides a nucleic acid origami device comprising a scaffold strand and a plurality of staple strands, having the structure A, B, C or D, wherein:

in the structure A (this structure has one key: either an aptamer, a nano-antenna or a "ligand-sensing molecule"-type key): (i) one of the staple strands comprises either (a) an aptamer domain capable of binding to a binding partner; (b) an oligonucleotide capable of binding a DNA binding protein; or (c) an oligoneucleotide attached to a nano-antenna capable of receiving an electromagnetic field, or one of the staple strands comprises an aptamer domain of (a) and another of the staple strands comprises an oligonucleotide of (b) or (c); (ii) another of the staple strands comprises a latch domain hybridized or bound to said aptamer domain of (a) or oligonucleotide of (b) or (c), the latch domain sequence being selected such that the aptamer domain of (a) is capable of binding to the binding partner such that the binding partner displaces the latch domain, or the latch domain is capable of hybridizing with an external oligonucleotide selected such that it displaces the aptamer domain; said latch domain is linked to a binding partner that is selected such that it has a first configuration under a first condition and a different second configuration under a different second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration; or the nano-antenna of (c), upon receipt of said electromagnetic field, undergoes inductive coupling and subsequent heating thereby displacing the latch domain from the oligonucleotide of (c); and (iii) the aptamer domain of (a) or the oligonucleotide of (b) or (c), and the latch domain, when hybridized or bound to one another, hold the device in a closed configuration; and the device transitions to an open configuration when said aptamer domain or oligonucleotide, and the latch domain, are not hybridized or bound to one another, in the structure B (this structure has two different aptamer keys): (i) one of the staple strands comprises a first aptamer domain capable of binding to a first binding partner; (ii) another of the staple strands comprises a second aptamer domain capable of binding to a second binding partner; (iii)

still another of the staple strands comprises a first latch domain hybridized to the first aptamer domain, the first latch domain sequence being selected such that the first aptamer domain is capable of binding to the first binding partner such that the first binding partner displaces the first latch domain, or the first latch domain is capable of hybridizing with an external oligonucleotide selected such that it displaces the aptamer domain; (iv) yet another of the staple strands comprises a second latch domain hybridized to the second aptamer domain, the second latch domain sequence being selected such that the second aptamer domain is capable of binding to the second binding partner such that the second binding partner displaces the second latch domain, or the second latch domain is capable of hybridizing with an external oligonucleotide selected such that it displaces the aptamer domain; and (v) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain, in the structure C (this structure is initially open and is closed by external oligonucleotides e.g. on another nanobot): (i) two of the staple strands each comprises a latch domain linked to an oligonucleotide capable of hybridizing with an external oligonucleotide; and (ii) said nucleic acid origami device is in an open configuration when each one of the oligonucleotides capable of hybridizing with an external oligonucleotide is not hybridized to said external oligonucleotide; and the device transitions to a closed configuration when both of said oligonucleotides capable of hybridizing with an external oligonucleotide are hybridized to said external oligonucleotides, in the structure D (this structure represents a nanorobot, which is initially open, and which can close in response to an external signal, such as a damage indicator). The difference from the structure C is the presence of the intrinsic oligonucleotide and the capability of hybridizing with the external soluble one); (i) another of the staple strands comprises a handle domain linked to or comprising an intrinsic oligonucleotide capable of hybridizing with an external soluble oligonucleotide and an oligonucleotide linked to a latch domain; (ii) two of the staple strands each comprises a latch domain linked to an oligonucleotide capable of hybridizing to each other and to the intrinsic oligonucleotide; (iii) each one of the oligonucleotides capable of hybridizing to each other and to the intrinsic oligonucleotide is hybridized to one intrinsic oligonucleotide and is selected such that the intrinsic oligonucleotide is capable of hybridizing to the external soluble oligonucleotide such that the external soluble oligonucleotide displaces the intrinsic oligonucleotide and the oligonucleotides capable of hybridizing to each other and to the intrinsic oligonucleotide hybridize to each other; and (iv) said nucleic acid origami device is in an open configuration when each one of the oligonucleotides capable of hybridizing to each other and to the intrinsic oligonucleotide is hybridized to said intrinsic oligonucleotide; and the device transitions to a closed configuration when each one of the oligonucleotides capable of hybridizing to each other and to the intrinsic oligonucleotide is not hybridized to said intrinsic oligonucleotide and is instead hybridized to each other, wherein said nucleic acid origami device is either alkylated, acylated or hydroxylated, or interacts with a compound capable of non-covalently binding to the major- or minor-groove of a double stranded nucleic acid, and therefore is resistant to nucleases, and/or said nucleic acid origami device lacks TLR9 recognition elements or the TLR9 recognition elements of said nucleic acid origami device are masked or modified and therefore said nucleic acid origami device is non-immunogenic.

The terms "nucleic acid origami device", "nanorobot", "nanobot", and simply "device", used herein interchangeably, refer to a nucleic acid, e.g., a DNA, origami device as defined above, in any one of the configurations described below.

The term "scaffold strand" as used herein refers to a long nucleic acid, e.g., DNA, strand, for example about 7250 bases long, that may be folded into a particular shape using a plurality of rationally designed "staple" DNA strands. However, there is no principal limit to the length of scaffold strand; it all depends on the size of device you want to build, so the scaffold strand could have any length between 15 and $10^{13}$ bases. The sequences of the staple strands are designed such that they hybridize to particular portions of the scaffold strands and, in doing so, force the scaffold strands into a particular shape. Methods useful in the making of DNA origami structures can be found, e.g., in Rothemund, P. W., Nature 440:297-302 (2006); Douglas et al., Nature 459:414-418 (2009); Dietz et al., Science 325:725-730 (2009); and US Patent Publication Nos. 2007/0117109, 2008/0287668, 20100069621 and 2010/0216978, each of which is incorporated by reference in its entirety. Staple design can be facilitated using, e.g., CADnano software, available at http://www.cadnano.org.

The term "latch domain" as used herein refers to a nucleic acid domain capable of hybridizing to an opposing aptamer domain or other nucleic acid (e.g., attached to a nano-antenna) and thereby holds the nucleic acid origami device in a closed configuration.

The term "aptamer domain" as used herein refers to a nucleic acid molecule selected such that it is capable of specifically binding a target molecule, much like an antibody is capable of specifically binding an antigen. Aptamers can be designed to target essentially any antigen of interest using methods known in the art. For example, methods of designing aptamers specific for a target of interest can be found in U.S. Pat. Nos. 5,582,981, 5,756,291, 5,840,867 and 7,745,607, and in Tang et al., Anal. Chem. 79:4900-4907 (2007), each of which are incorporated by reference in its entirety.

The terms "hybridized" or "hybridizing" as used herein refer to the binding of two strands of nucleic acid molecules to each other, and are meant to include that the two strands are capable of hybridizing to each other, or that the two strands are complementary to each other, wherein the complementarity of the two strands may vary in order to calibrate the affinity between the two strands. For example, each one of the two strands may have a sequence of base pairs that is 100, 99, 98, 96, 94, 92, 90, 85, 80, 75, 70, 65 or 60% complementary to the sequence of the other strand.

The aptamer domain is capable of binding to a binding partner such that the binding partner displaces the latch domain. In the case the binding partner is a ligand such as a target antigen that binds to the aptamer by inducing a structural change in the aptamer domain enabling it to bind to the ligand, the ligand binds to the aptamer domain at a higher affinity than the latch domain causing the aptamer to lose its linear configuration that enables it to hybridize with the latch domain, and therefore releases the latch domain. In case the binding partner is a nucleic acid molecule, the nucleic acid molecule may have a higher degree of complementarity with the aptamer domain than has the latch domain and therefore displaces the latch domain. Conceptually, the nucleic acid molecule could be complementary to the latch domain and bind to it, thus displacing the aptamer domain. In both cases, the displacement would lead to the transitions of the device from a closed to an open configuration. In all embodiments wherein it is defined that the binding partner binds to the aptamer domain such that the binding partner displaces the latch domain, it should be understood that, in the case of the binding partner being an oligonucleotide, the binding partner may alternatively bind to the latch domain such that oligonucleotide displaces the latch domain.

The term "external oligonucleotide" as used herein refers to an oligonucleotide that is not comprised within a particular device being defined, but is found e.g. on a neighboring identical or different device.

The term "intrinsic oligonucleotide" as used herein refers to an oligonucleotide that is comprised within a particular device being defined.

The term "damage cue" or "damage indicator" as used herein may be an obligatory intracellular molecule such as ATP, ribosome fragments, rRNA, nuclear pore components, histones, etc. for discerning cell damage in a non-discriminatory way; or microRNA, or certain isoforms or analogs of the above mentioned cues, such as glycosylation or phosphorylation variants, differentially present in a specific type of cell, a normal cell or a tumor cell.

In this regard, in certain embodiments, the external soluble oligonucleotide may be a microRNA or an oligonucleotide comprised within the microRNA.

A non-limiting example of a "oligonucleotide capable of binding a DNA binding protein" is an isolated response element originally found within a gene promoter. A specific example is the glucose responsive regulatory element.

The term "nuclease" as used herein refers to an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

The term "resistant to nucleases" as used herein refers to nucleic acid molecules that have been modified so that they are more stable in the presence of nucleases than unmodified molecules.

The term "TLR9 recognition element" as used herein refers to elements on a nucleic acid molecule, e.g., a DNA molecule, that are recognized by Toll Like Receptor (TLR) 9 present in the cytoplasm of antigen presenting cells. TLR9 is expressed by numerous cells of the immune system such as dendritic cells, B lymphocytes, monocytes and natural killer (NK) cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

The terms "CpG motif" and "CpG island" are used interchangeably herein and refer to short single-stranded synthetic nucleic acid molecules that contain a cytidine triphosphate deoxynucleotide ("C") followed by a guanidine triphosphate deoxynucleotide ("G"). The "p" refers to the phosphodiester link between consecutive nucleotides, although some DNA nucleic acids have a modified phosphorothioate (PS) backbone instead.

The term "masked nucleic acid origami device" refers to a device that is linked to a molecule capable of covering domains otherwise accessible to the environment, such as CpG islands and thereby making these domains inaccessible to the environment.

The term "non-immunogenic" as used herein refers to a molecule that does not induce a response against it by the immune system in a mammal, or induces a weaker response than would have been induced by the same molecule that differs only in that it has TLR9 recognition elements that have not been masked or modified.

Examples of non-covalent binding are binding involving ionic bonds, electrostatic interactions, hydrophobic interactions, hydrogen bonds or van der Waals forces.

In certain embodiments, in the nucleic acid origami device having the structure A: (i) one of the staple strands comprises a first aptamer domain and another of the staple strands comprises a second aptamer domain wherein both aptamer domains are capable of binding to identical binding partners; (ii) still another of the staple strands comprises a first latch domain hybridized to the first aptamer domain and selected such that the first aptamer domain is capable of binding to the binding partner such that the binding partner displaces the first latch domain; (iii) yet another of the staple strands comprises a second latch domain hybridized to the second aptamer domain and selected such that the second aptamer domain is capable of binding to the binding partner such that the binding partner displaces the second latch domain; and (iv) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain.

In certain embodiments, the nucleic acid origami is non-immunogenic, resistant to nucleases, or both non-immunogenic and resistant to nucleases.

In certain embodiments, the nucleic acid of the nucleic acid origami device as defined herein above is DNA.

In certain embodiments, the TLR9 recognition elements are CpG islands, and the nucleic acid origami device may be methylated, preferably at CpG dinucleotides.

The term "methylated" refers to a nucleic acid molecule to which a methyl group has been added, specifically to the cytosine or adenine nucleotide.

In certain embodiments, the nucleic acid origami device is methylated at the carbon atom in position 5 of cytosine residues; at the amino group linked to the carbon atom in position 4 of cytosine residues; or at the amino group linked to the carbon atom in position 6 of adenine residues, for example, the nucleic acid origami device may be methylated at the carbon atom in position 5 of cytosine residues in CpG dinucleotides.

In certain embodiments, the nucleic acid origami device is modified at either cytosine or guanine residues in CpG dinucleotides. For example, the cytosine or guanine residue may be modified by covalently linking it via a linker to a macromolecule having a functional group, wherein said macromolecule is selected from a polymer such as poly(ethylene)glycol, polystyrene, poly(vinyl)chloride, pectin, polygalacturonic acid, polygalacturonic acid and poly(lactic-co-glycolic acid) (PLGA), a peptide, a lipid or a polysaccharide. The functional group may be, but is not limited to, an amino, mercapto, and carboxyl group.

In certain embodiments, the compound capable of non-covalently binding to the major- or minor-groove of a double stranded nucleic acid is selected from netropsin, distamycin, an oligoamide, a sugar-oligoamide conjugate or a bis-amidine. In a particular embodiment, the compound is netropsin, and the netropsin is further covalently linked through two of its terminal amino groups, optionally via a linker, to the double stranded nucleic acid, as shown, e.g., in FIGS. 7 and 8.

In certain embodiments, one or more further staple strands of the nucleic acid origami device defined herein each comprises a handle domain bound to a payload, more specifically, to a payload moiety, optionally via a linker.

In one embodiment, the linker comprises an oligonucleotide having a sequence complementary to the sequence of the handle domain and optionally comprising a further domain comprising a recognition site for enzymatic cleavage, and the payload is bound to the handle domain through the hybridization of the oligonucleotide to the handle domain. This further domain may comprise a peptide linker comprising a protease recognition site for cleavage by a protease, such as a matrix metalloproteinase. Alternatively, the linker may comprise a protein capable of binding a small molecule such as, but not limited to, a cyclooxygenase protein capable of binding paracetamol, a sodium channel subunit capable of binding tetrodotoxin and an anti-digoixin antibody capable of binding digoxin.

The term "protease recognition site" refers to an amino acid sequence recognized by an endo peptidase, such as but not limited to: Trypsin—cuts after Arg or Lys, unless followed by Pro; Chymotrypsin—cuts after Phe, Trp, or Tyr, unless followed by Pro; Elastase—cuts after Ala, Gly, Ser, or Val, unless followed by Pro; Thermolysin—cuts before Ile, Met, Phe, Trp, Tyr, or Val, unless preceded by Pro; Pepsin—cuts before Leu, Phe, Trp or Tyr, unless preceded by Pro; and Endopeptidase V8 (also known as Glu-C)—cuts after Glu.

In certain embodiments, the payload each independently is a drug, such as insulin, an antibody or a fragment thereof, a cell surface receptor ligand or a biologically active fragment thereof, a small molecule, a nucleic acid such as an oligonucleotide, a nuclease, an aptamer, a lipid, a glycan, a protein, a glycoprotein, a glycolipid, a nanoparticle, a fluorophore, a radioactive compound, a nano-antenna or a liposome. The payload being an oligonucleotide may function as an "external oligonucleotide" for another device.

The terms "payload" and "payload moiety" are used herein interchangeably and refer both to the free payload and to said payload when covalently linked directly to the handle domain or to the linker while maintaining its biological activity.

In certain embodiments, the nano-antenna of the nucleic acid origami device as defined above, e.g., when having the structure A, or being used as a payload when linked to the handle domain, optionally via a linker, each independently comprises a metal quantum dot, a metal nanoparticle, or a metal nanocrystal, wherein said metal is preferably Au.

In other embodiments, the plurality of staple strands are selected such that at least one of the payloads is positioned on an inner surface of the nucleic acid origami device when the device is in the closed configuration; and the transition to the open configuration causes said payload to be positioned on an outer surface of the nucleic acid origami device.

The term "inner surface" with respect to the nucleic acid origami device of the present invention in any one of the configurations defined herein, refers to any surface area of the device that is sterically precluded from interacting with members in the immediate environment surrounding the nucleic acid origami device, such as the surface of a cell, while an "outer surface" is any surface area of the device that is not sterically precluded from interacting with members in the immediate environment surrounding the nucleic acid origami device the surface of a cell.

In still other embodiments, the staple strands comprises a handle domain positioned on an outer surface of the device when the device is in the closed configuration, and in this case, the handle domain is bound to a payload preferably selected from an oligonucleotide or a liposome.

In certain embodiments, the handle domain positioned on the outer surface of the device when the device is in the closed configuration becomes positioned on an inner surface of the device when the device is in the open configuration.

The shape of the device may be chosen according to the purpose of the device, and is easily obtained by defining the shape in a specialized computer program well known in the art of DNA origami such as CADnano software, available at http://www.cadnano.org.

In certain embodiments, the plurality of staple strands are selected such that the origami device is substantially barrel-shaped and in other embodiments the plurality of staple strands are selected such that the nucleic acid origami device has a substantially hexagonal tube shape. The plurality of staple strands may be selected such that the nucleic acid origami device comprises an open end and they may be selected such that the nucleic acid origami device comprises two open ends.

In certain embodiments: (i) in the nucleic acid origami device having the structure A or B, the plurality of staple strands are selected such that the nucleic acid origami device comprises a first domain and a second domain, wherein the first domain comprises said aptamer domain(s) of (a) each capable of binding to a binding partner; said oligoneucleotide(s) of (b) each capable of binding a DNA binding protein; or said oligonucleotide(s) of (c) each attached to a nano-antenna; and the second domain comprises said latch domain(s), wherein a first end of the first domain is attached to a first end of the second domain by at least one single-stranded nucleic acid hinge and the second end of the first domain is attached to the second end of the second domain by the hybridization or binding of each one of said aptamer domains or said oligonucleotides to said latch domains, respectively; or (ii) in the nucleic acid origami device having the structure C or D, the plurality of staple strands are selected such that the nucleic acid origami device comprises a first domain and a second domain, wherein each one of said first and second domains comprises one of said latch domains linked to an oligonucleotide capable of hybridizing to each other and the intrinsic oligonucleotide or an external oligonucleotide, wherein a first end of the first domain is attached to a first end of the second domain by at least one single-stranded nucleic acid hinge and the second end of the first domain is not attached to the second end of the second domain.

In certain embodiments: (i) the plurality of staple strands in the nucleic acid origami device having the structure A or B are selected such that the second end of the first domain becomes unattached to the second end of the second domain if each one of said aptamer domains is contacted by and binds to its respective binding partner and/or if each one of said nano-antennas receives an electromagnetic field and undergoes inductive coupling and subsequent heating; (ii) the plurality of staple strands in the nucleic acid origami device having the structure C are selected such that the second end of the first domain becomes attached to the second end of the second domain if each one of said latch domains is hybridized to a different one of said external oligonucleotides; or the plurality of staple strands in the nucleic acid origami device having the structure D are selected such that the second end of the first domain becomes attached to the second end of the second domain if the latch domains are hybridized to each other.

In certain embodiments, the binding partner is an antigen selected from a tumor associated antigen; a cell-membrane receptor; a secreted or membrane bound growth factor; a hormone; a cytokine; a ligand; a chemokine; a bacterial, a viral or parasitic antigen; a lipid; an oligonucleotide; a sugar, an enzyme, a DNA binding protein or a damage cue as defined herein above.

The nano-device may be a glucose-sensing device that exhibits insulin on its surface at high glucose concentration. For this purpose, as explained above, the nano-devise may comprise a binding partner that is selected such that it has a first configuration under a first condition and a different second configuration under a different second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration thereby opening the device and exposing the insulin. In particular, this binding partner may be an enzyme, for example a glucokinase (see Example 6).

Thus, in certain embodiments, the enzyme is a glucokinase and the aptamer domain of (a) is capable of binding to the glucokinase having the first configuration but is incapable of binding to the glucokinase having the second configuration; or the DNA binding protein is a glucose response factor and said oligonucleotide of (b) is a glucose responsive regulatory element capable of binding to the glucose response factor having the first configuration but incapable of binding to the glucose response factor having the second configuration. The glucokinase may be a mammalian glucokinase, such as but not limited to human, mouse or rat beta cell glucokinase.

In certain embodiments, the first condition is a glucose concentration in the range of 0-4.5 mM and the second condition is a glucose concentration above 4.5 mM, for example in the range of 5-10 mM.

In certain embodiments, the nucleic acid origami device comprises a scaffold strand and a plurality of staple strands, having the structure A, wherein: (i) one of the staple strands comprises either (a) an aptamer domain capable of binding to a glucokinase having a first configuration but incapable of binding to the glucokinase having a second configuration; or (b) an oligonucleotide comprising a nucleotide sequence of a glucose responsive regulatory element capable of binding a glucose response factor having a first configuration but incapable of binding to the glucose response factor having a second configuration; (ii) another of the staple strands comprises a latch domain linked to the glucokinase, and the aptamer of (a) is capable of binding to the glucokinase having the first configuration but incapable of binding to the glucokinase having the second configuration such that the latch domain is displaced from the aptamer of (a) when the binding partner transitions from the first to the second configuration; or another of the staple strands comprises a latch domain linked to the glucose response factor and the oligonucleotide of (b) is capable of binding to the glucose response factor, having the first configuration but incapable of binding to the glucose response factor having the second configuration such that the latch domain is displaced from the oligonucleotide of (b) when the glucose response factor transitions from the first to the second configuration; (iii) the aptamer domain of (a) or the oligonucleotide of (b), and the latch domain, when bound to one another, hold the device in a closed configuration; and the device transitions to an open configuration when said aptamer domain of (a) or oligonucleotide of (b), and the latch domain, are not hybridized or bound to one another; and (iv) a further staple strand comprises a handle domain bound to insulin, optionally via a linker, and the insulin is positioned on an inner surface of the nucleic acid origami device when the device is in the closed configuration; and the transition to the open configuration causes the insulin to be positioned on an outer surface of the nucleic acid origami device, wherein said nucleic acid origami device is either alkylated, acylated or hydroxylated, or interacts with a compound capable of non-covalently binding to the major- or minor-groove of a double stranded nucleic acid, and therefore is resistant to nucleases, and/or said nucleic acid origami device lacks TLR9 recognition elements or the TLR9 recognition elements of said nucleic acid origami device are masked or modified and therefore said nucleic acid origami device is non-immunogenic.

In one aspect, the present invention is directed to a method for treating type I diabetes, type II diabetes, or hyperglycemia, comprising administering to an individual in need thereof a pharmaceutically effective amount of a nucleic acid origami device comprising a glucokinase or a glucose response factor as described herein above.

In another aspect, the present invention provides a nucleic acid origami device comprising a glucokinase or a glucose response factor as described herein above for use in treatment of type I diabetes, type II diabetes, or hyperglycemia. In particular the nucleic acid origami device used in the treatment of type I diabetes, type II diabetes, or hyperglycemia comprises a glucokinase.

In certain embodiments, the treatment of type I or II diabetes or hyperglycemia comprises improving glucose tolerance test results.

The nano-device may be used to specifically kill target cells while sparing non-target cells, e.g. normal healthy cells. This is achieved by administering, by means of the nano-device, a toxin that preferentially kills the target cells, and by stopping the action of the nano-device when it senses a distress or damage cue released from the normal healthy cells that are also damaged in the process. For this purpose, certain configurations of the nucleic acid origami device comprises a scaffold strand and a plurality of staple strands, having the structure D, wherein: (i) one of the staple strands comprises a handle domain linked to or comprising an intrinsic oligonucleotide capable of hybridizing with an external soluble oligonucleotide and an oligonucleotide linked to a latch domain; (ii) two of the staple strands each comprises a latch domain linked to an oligonucleotide capable of hybridizing to each other and to the intrinsic oligonucleotide; (iii) each one of the oligonucleotides capable of hybridizing to each other and to the intrinsic oligonucleotide is hybridized to one intrinsic oligonucleotide and is selected such that the intrinsic oligonucleotide is capable of hybridizing to the external soluble oligonucleotide such that the external soluble oligonucleotide displaces the intrinsic oligonucleotide and the oligonucleotides capable of hybridizing to each other and to the intrinsic oligonucleotide hybridize to each other; (iv) said nucleic acid origami device is in an open configuration when each one of the oligonucleotides capable of hybridizing to each other and to the intrinsic oligonucleotide is hybridized to said intrinsic oligonucleotide; and the device transitions to a closed configuration when each one of the oligonucleotides capable of hybridizing to each other and to the intrinsic oligonucleotide is not hybridized to said intrinsic oligonucleotide and is instead hybridized to each other; and (v) a further staple strand comprises a handle domain bound to a drug, such as a cytotoxic drug, optionally via a linker, wherein said nucleic acid origami device is either alkylated, acylated or hydroxylated, or interacts with a compound capable of non-covalently binding to the major- or minor-groove of a double stranded nucleic acid, and therefore is resistant to nucleases, and/or said nucleic acid origami device lacks TLR9 recognition elements or the TLR9 recognition elements of said nucleic acid origami device are masked or modified and therefore said nucleic acid origami device is non-immunogenic.

In a further aspect, the present invention provides a method for killing target cells in the vicinity of non-target cells, said killing being discontinued if said non-target cells are damaged, comprising administering to an individual in need a pharmaceutically effective amount of a nucleic acid origami device having the structure D, wherein the killing is discontinued when the external soluble oligonucleotide leaking from the non-target cells hybridizes to the intrinsic oligonucleotide and cause the nucleic acid origami device to close.

In another aspect, the present invention provides a multimodal nucleic acid origami device comprising at least two inter-connected nucleic acid origami devices each independently according to any one of the embodiments defined herein above.

In certain embodiments, in the multimodal nucleic acid origami device, each one of said aptamer domains capable of binding to a binding partner is identical to or different from at least one of the other aptamer domains.

In certain embodiments, one or more further staple strands in at least one of said at least two inter-connected nucleic acid origami devices each comprises a handle domain bound to a payload, optionally via a linker. The payload may each independently be a drug, such as insulin, an antibody or a fragment thereof, a cell surface receptor ligand or a biologically active fragment thereof, a small molecule, a nucleic acid such as an oligonucleotide, a nuclease, an aptamer, a lipid, a glycan, a protein, a glycoprotein, a glycolipid, a nanoparticle, a fluorophore, a radioactive compound, a nano-antenna or a liposome.

In some embodiments, the further staple strands in more than one of said at least two inter-connected nucleic acid origami devices each comprises a handle domain bound to a payload, and said payloads are either identical or different.

In yet another aspect, the present invention is directed to a pharmaceutical composition comprising a nucleic acid origami device or a multimodal nucleic acid origami device according to any one of the embodiments defined herein above, and a pharmaceutically acceptable carrier.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for intra-brain administration.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For administration by inhalation, for example for nasal administration, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In certain embodiments the pharmaceutical composition is formulated for administration by any known method as described above.

As found in accordance with the present invention, the nucleic acid origami device, when bound to a receptor at a surface of a cell, is capable of attenuating internalization of the receptor into said cell.

In still another aspect, the present invention is thus directed to a nucleic acid origami device comprising a scaffold strand and a plurality of staple strands, wherein (i) one of the staple strands comprises either an aptamer domain capable of binding a cell-membrane receptor or a ligand to said receptor; (ii) said nucleic acid origami device is either alkylated, acylated or hydroxylated, or interacts with a compound capable of non-covalently binding to the major- or minor-groove of a double stranded nucleic acid, and therefore is resistant to nucleases; and/or (iii) said nucleic acid origami device lacks TLR9 recognition elements or the TLR9 recognition elements of said nucleic acid origami device are masked or modified and therefore said nucleic acid origami device is non-immunogenic, wherein said nucleic acid origami device, when bound to said receptor at a surface of a cell, attenuates or prevents internalization of the receptor into said cell.

The term "internalization" as used herein refers to a process also termed endocytosis, i.e. a process by which cells absorb molecules (such as proteins) by engulfing them. Endocytosis pathways can be subdivided into four categories: i.e., clathrin-mediated endocytosis, caveolae, macropinocytosis, and phagocytosis. The size of the nucleic acid origami device used to prevent internalization can be adjusted depending on the specific pathway to be inhibited.

In certain embodiments, the nucleic acid origami device capable of attenuating or preventing internalization of a receptor into a cell has one sole configuration.

In additional aspects, the present invention provides a pharmaceutical composition comprising the nucleic acid origami device capable of attenuating or preventing internalization of a receptor into a cell and a pharmaceutically acceptable carrier, and use of this nucleic acid origami device or the pharmaceutical composition comprising it for attenuating or preventing internalization of a cell-membrane receptor into a cell.

DNA origami is a robust method for fabrication of 3D shapes with complex geometries at the nanoscale. This method has been used to construct diverse objects for use as spatial templates for patterning matter with sub-nanometer resolution. However, packing large amounts of DNA, which is essentially a 1D molecule, into a 3D space $10^3$ to $10^4$-fold smaller, likely exerts profound changes on the chemical nano-environment inside or near the folded shape, which never occur naturally and were never encountered in evolution. The inventors of the present invention have further found that chemical reactions normally occurring in an aqueous solution fail to occur inside the device, most probably due to the high density of negative charges in the inner space of the device, which attenuates chemical reactions such as hydrolysis and oxidation. The device of the present invention may thus be used for improving the stability of active agents prone to deactivation by various chemical reactions, thereby extending the shelf-life of these active agents.

In view of the above, in yet still another aspect, the present invention provides a hollow nucleic acid origami device having two open ends, said hollow nucleic acid origami device comprising a scaffold strand and a plurality of staple strands, wherein said hollow nucleic acid origami device has one sole configuration and said staple strands are selected such that the hollow nucleic acid origami device allows a biologically active agent having a maximum cross-section smaller than the inner cross-section of the hollow nucleic acid origami device to enter and exit the inner space of the hollow nucleic acid origami device, wherein said staple strands are further selected such that a predetermined equilibrium is established between the period of time said biologically active agent is present in said inner space of the hollow nucleic acid origami device and the period of time said biologically active agent is present outside said inner space of the hollow nucleic acid origami device.

In certain embodiments, the predetermined equilibrium is established such that the period of time said biologically active agent is present in said inner space of the hollow nucleic acid origami device is longer than the period of time said biologically active agent is present outside said inner space of the hollow nucleic acid origami device.

In certain embodiments, the hollow nucleic acid origami device has a barrel shape or a hexagonal shape.

In a further aspect, the present application is directed to a shelf life extending formulation comprising a biologically active agent and the hollow nucleic acid origami device of any one of its preceding embodiments, wherein said inner space of the hollow nucleic acid origami device comprises a high density of negative charges that attenuates inactivation of said active agent, which may result from, e.g., hydrolysis or oxidation of said active agent. The high density of charges may be in order of 10, 100, 1000, $10^4$, $10^5$, $10^6$ or higher than unfolded DNA.

In still further aspects, the present invention provides a method for preparing a nucleic acid origami device as defined herein above, including the basic nucleic acid origami device having the structure A, B or C, the multimodal nucleic acid device, and the device capable of attenuating or preventing internalization of a cell-membrane receptor into a cell, that is non-immunogenic, resistant to nucleases or both.

In one of these aspects, the present invention provides such a method for preparing a nucleic acid origami device that is non-immunogenic, said method comprising: (i) designing nucleic acid sequences composing the scaffold strand(s) and staple strands of said nucleic acid origami device or multimodal nucleic acid origami device such that said nucleic acid sequences either (a) do not form CpG islands on said nucleic acid origami device or multimodal nucleic acid origami device and therefore is non-immunogenic; or (b) do form CpG islands on said nucleic acid origami device or multimodal nucleic acid origami device; (ii) synthesizing or otherwise obtaining said scaffold strand (s) and staple strands; (ii) contacting said scaffold and staple strands thereby forming a nucleic acid origami device or multimodal nucleic acid origami device; and (iii) masking said CpG islands, if present, by methylation, thereby rendering said nucleic acid origami device or multimodal nucleic acid origami device non-immunogenic.

In another of these aspects, the present invention provides such a method for preparing a nucleic acid origami device that is resistant to nucleases, said method comprising: (i) designing nucleic acid sequences composing the scaffold strand(s) and staple strands of said nucleic acid origami device or multimodal nucleic acid origami device such that said nucleic acid sequences optionally do not form CpG islands on said nucleic acid origami device or multimodal nucleic acid origami device; (ii) synthesizing or otherwise obtaining said scaffold strand(s) and staple strands; (iii) contacting said scaffold and staple strands thereby forming a nucleic acid origami device or multimodal nucleic acid origami device; (iv) masking said CpG islands, if present, and optionally adenine residues on said nucleic acid origami device or multimodal nucleic acid origami device, by methylation; and (v) optionally interacting said nucleic acid origami device or multimodal nucleic acid origami device with a compound capable of non-covalently binding to the major- or minor-groove of a double stranded nucleic acid, thereby obtaining said nucleic acid origami device or multimodal nucleic acid origami device that is resistant to nucleases.

In a further of these aspects, the present invention provides such a method for preparing a nucleic acid origami device that is both non-immunogenic and resistant to nucleases, said method comprising: (i) designing nucleic acid sequences composing the scaffold strand(s) and staple strands of said nucleic acid origami device or multimodal nucleic acid origami device such that said nucleic acid sequences either (a) do not form CpG islands on said nucleic acid origami device or multimodal nucleic acid origami device and therefore is non-immunogenic; or (b) do form CpG islands on said nucleic acid origami device or multimodal nucleic acid origami device; (ii) synthesizing or otherwise obtaining said scaffold strand(s) and staple strands; (iii) contacting said scaffold and staple strands thereby forming a nucleic acid origami device or multimodal nucleic acid origami device; (iv) masking said CpG islands, if present, and optionally adenine residues on said nucleic acid origami device or multimodal nucleic acid origami device, by methylation; and (v) optionally interacting said nucleic acid origami device or multimodal nucleic acid origami device with a compound capable of non-covalently binding to the major- or minor-groove of a double stranded nucleic acid, thereby obtaining said nucleic acid origami device or multimodal nucleic acid origami device that is both non-immunogenic and resistant to nucleases.

In certain embodiments, the methylation is performed by contacting said device with a methyltransferase and a methyl donor, such as S-adenosyl methionine. Non limiting example of methyltransferases include dam Methyltransferase, TaqI Methyltransferase, AluI Methyltransferase, BamHI Methyltransferase, CpG Methyltransferase (M.SssI), EcoRI Methyltransferase, G9a Methyltransferase, CpG Methyltransferase (M.CviPI), HaeIII Methyltransferase, HhaI Methyltransferase, HpaII Methyltransferase, Human DNA (cytosine-5) Methyltransferase (Dnmt1) Amino-terminal Ab, Human DNA (cytosine-5) Methyltransferase (Dnmt1), Human DNA (cytosine-5) Methyltransferase (Dnmt3A) Amino-terminal Ab, Human DNA (cytosine-5) Methyltransferase (Dnmt3B) Carboxy-terminal Ab, Human PRMT1 Methyltransferase, MspI Methyltransferase, SETT Methyltransferase or rat liver methylase as disclosed by Simon D, Grunert F, von Acken U, Döring H P, Kröger H., 1978 DNA-methylase from regenerating rat liver: purification and characterization. Nucleic Acids Res. 1978 June; 5(6):2153-67.

The invention will now be illustrated by the following non-limiting examples.

EXAMPLES

Materials and Methods

DNA Scaffold. A 7249 bp circular single-strand DNA molecule was used in the following examples (M13mp18 DNA; New England Biolabs; NEB #N4040; SEQ ID NO: 1).

Staples. Purchased from Integrated DNA Technologies (SEQ ID NOs: 2-279). All sequences are in the 5' to 3' direction. The oligonucleotides were reconstituted in ultrapure, DNase/RNase-free water to 100 µM concentration and stored at −20° C.

Methods:

Robot Preparation. Robots were initially produced by mixing M13mp18 ssDNA as scaffold strand (final concentration of 20 nM) and staple strands (final concentrations of 200 nM of each strand). Buffer and salts of solution included 5 mM Tris, 1 mM EDTA (pH 8.0 at 20° C.) and 10 mM $MgCl_2$. The mixture was subjected to a thermal-annealing ramp for folding. Initially the following program was used: 80° C. to 60° C. at 2 min/° C., 60° C. to 20° C. at 150 min/° C.

Purification of folded robots: After folding, excess staples were removed by centrifugal filtration using AMICON Ultra-0.5 mL 100K centrifugal filters (Millipore). Folding buffer was added to reach a total volume of 500 µL, after which samples were centrifuged at 12,000 g for 10 min. this was repeated three times. DNA concentration was measured by spectrophotometer (Thermo Sci. NanoDrop 2000c).

Figure 1B:
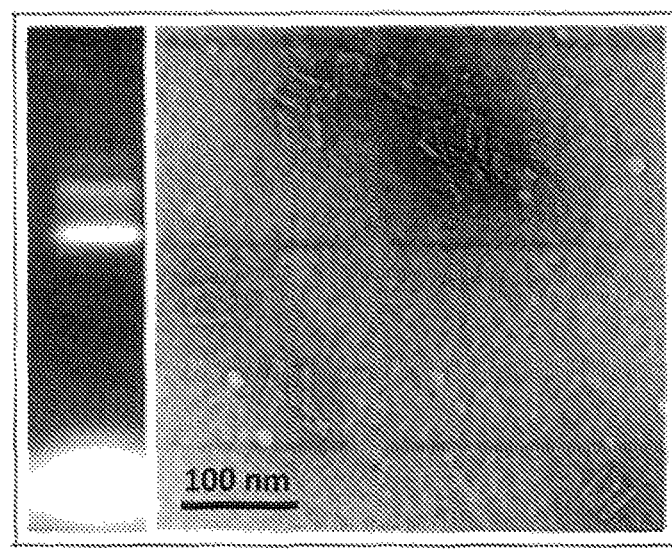

Gel purification of folded samples. Leading monomer bands were visualized on a UV table and excised from a 1.5%-2% agarose gel (running buffer is 0.5×TBE supplemented with 10 mM $MgCl_2$), frozen at −20° C. for 5 min, chopped to small pieces and centrifuged at 13,000 g for 3 min inside a QUANTUM PREP FREEZE N' SQUEEZE DNA Gel Extraction spin column (Bio-Rad). Recovered solution was measured for DNA concentration by spectrophotometer (Thermo Sci. NanoDrop 2000c) and prepared for imaging by transmission electron microscopy (TEM) (FIGS. 1A-B).

Figure 2:
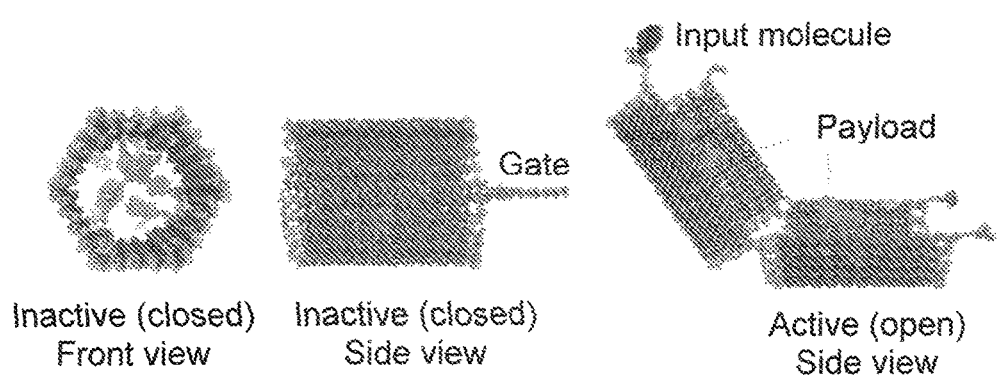
FIG. 2 depicts a 3D representation of a nanorobot in its inactive state (left panel in front view and middle panel in side view) and in its active open state (right panel).

TEM Negative-Stain. Briefly, 5 µL of 0.5 M NaOH are added to a pre-made frozen aliquot of 100 µL 2% uranyl formate solution (Polysciences, 24762) followed by rigorous vortexing for 3 minutes, after which solution is centrifuged at 18,000 g for 5 minutes and precipitate is removed. Robot samples at 1-5 nM concentration are loaded onto a TEM Grid (Science Services, EFCF400-Cu-50) immediately after glow-discharge treatment (Emitech K100X), followed by two consecutive washes with 0.1% uranyl formate solution. During the third wash the grid is incubated with uranyl formate solution for 30 seconds. Samples are visualized using a TEM microscope (JEM-1400, JEOL) an hour to one week after negative staining. FIG. 1A shows robots folded during 80-60° C. at 2 min/° C. and 60-10° C. at 150 min/° C. and FIG. 1B shows robots folded during 80-60° C. at 5 min/° C., 60-10° C. at 75 min/° C.). A graphic depiction of the nanorobots used in the examples is shown in FIG. 2.

Payload preparation. Antibodies were digested using a commercial kit (Thermo) with immobilized ficin in mouse IgG digestion buffer with 25 mM cysteine by shaking at a 37° C. water bath for 4 hours. Antibody Fab' fragments were purified by centrifugal filtration (AMICON, 10K MWCO centrifugal filter, Millipore) and evaluated by spectrophotometer (Thermo Sci. NanoDrop 2000c). Fab' fragments were buffer-exchanged into 0.05 M sodium borate buffer, pH 8.5, and incubated with DyLight Amine-Reactive Dye (Thermo) for 1 hour at room temperature on a rotary shaker. Excess dye was thoroughly removed using AMICON, 10K MWCO centrifugal filter (Millipore). Fab' fragments were incubated for 1 minute with 5'-amine-modified linker oligonucleotide (5AmMC6/GAACTGGAGTAGCAC (SEQ ID NO: 280), Integrated DNA Technologies) at a molar ratio of 1 to 10, in a 0.1 M MES-buffered saline, pH 4.7 (Pierce #28390). EDC (Thermo, #22980) was added at a molar ratio of 5000 to 1 Fab' fragment and incubated at room temperature for 1 hour on a rotary shaker. Afterwards, Tris was added to a final concentration of 10 mM and solution was filtered via AMICON column 30K MWCO (Millipore).

Loading of robot. Oligonucleotide-Fab' concentration was evaluated via absorption at 260 and 280 nm. Loading was performed for 2 hours on a rotary shaker at room temperature in folding buffer (10 mM $MgCl_2$ in 1×TAE) at a 2-fold molar excess of payloads to loading sites. Finally, loaded robots were cleaned by centrifugal filtration with a 100K MWCO AMICON column (Millipore) as described above.

Preparation of Glucose-Concentration Sensitive Robots. Beta-cell G1cK was purchased from commercial sources. To attach the protein to the robot gate, the gate complementary staple strand (opposing the aptamer staple strand) was ordered from Integrated DNA Technologies with a 3'-amine modification. The G1cK was then conjugated to this oligonucleotide using EDC/Sulfo-NHS conjugation (reagents purchased from Pierce-Thermo Scientific) and the DNA-protein hybrid was cleaned using centrifugal gel filtration.

Isomer-selective aptamers were selected from a starting random library of DNA sequences ($10^{15}$) in the presence of 4 mM glucose to enable only the proper conformer to exist in the process.

Example 1

DNA Origami Devices can be Made Non-immunogenic and Resistant to DNase I

The DNA origami device was assembled as follows: Scaffold, which is a 7249 bp circular single-strand DNA molecule (SEQ ID NO: 1; M13mp18 DNA; purchased from New England Biolabs (NEB #N4040)) and staple strands, examples of which are disclosed as SEQ ID NOs: 2-279, were mixed in Tris-Acetate-EDTA buffer supplemented with between 0.5 to 20 mM magnesium, at a ratio ranging from 1:4 to 1:100, respectively. The mixture was subjected to a temperature-annealing ramp of the following sequence: 1) from 85° C. to 61° C., 30 min/° C.; 2) from 60° C. to 25° C., 150 min/° C. Other annealing ramps can also be used. The folded nanorobots were finally cleaned by either agarose gel extraction or centrifugal column filtration. Analysis was done by gel electrophoresis and atomic force microscopy (AFM).

Figure 3A:
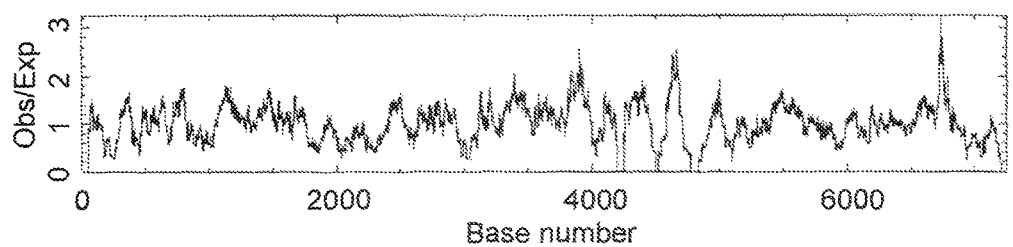
FIGS. 3A-C depict CpG island maps (output of CpG finder: http://cpgislands.usc.edu) as described by Takai and Jones (Comprehensive analysis of CpG islands in human chromosomes 21 and 22; Proc Natl Acad Sci USA. 99(6): 3740-5 (2002)).
Figure 3B:
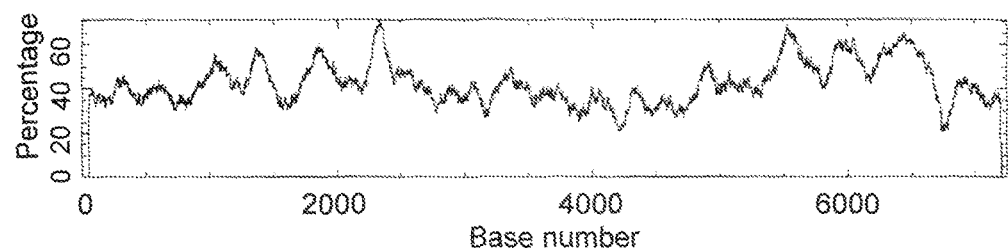
Figure 3C:
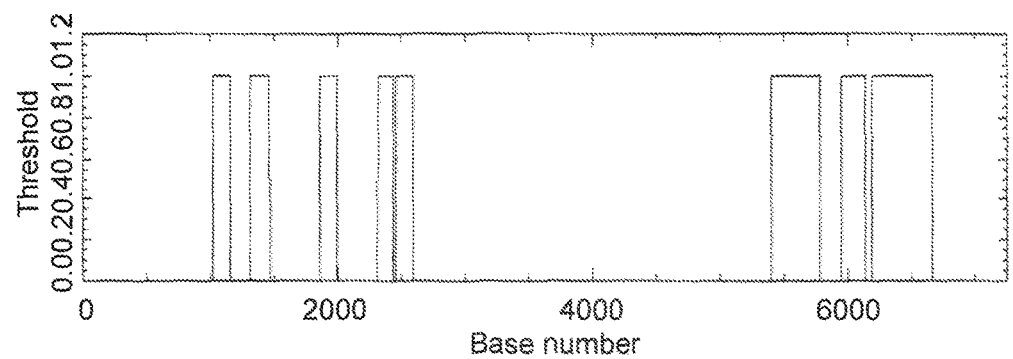

In this study we used a slightly modified version of the DNA origami nanorobot demonstrated elsewhere (Douglas et al., 2012) as a plausible prototype of a therapeutic device. The nanorobot chassis includes 324 CpG motifs (FIG. 3A). Eight regions are identified as >100 bp CpG islands as shown in FIG. 3C.

(i) Resistance to nucleases. The DNA making up the nanorobots may be modified or masked by linking it to a small molecule, peptide, nucleic acid, protein, lipid, polysaccharide or any molecule that binds DNA through the major groove or minor groove. The attachment of such a molecule blocks the access of nucleases to the DNA origami device.

Figure 4:
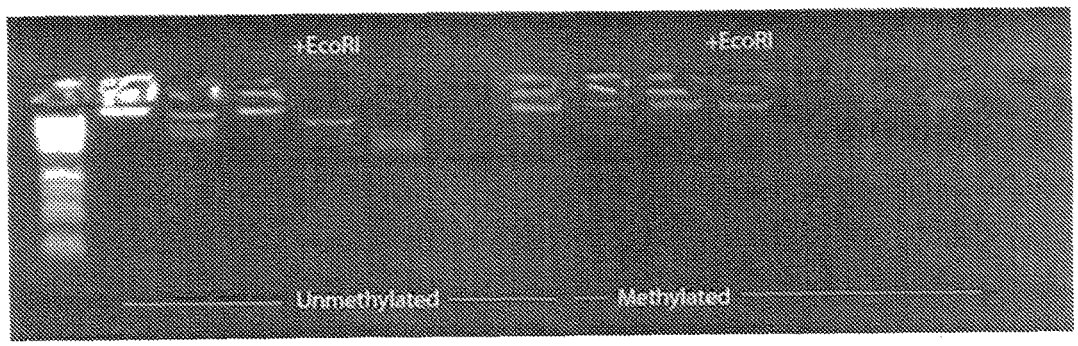
FIG. 4 depicts an agarose gel showing that methylated DNA origami devices are resistant to bacterial restriction endonucleases. This figure shows the response of methylated vs. unmethylated DNA origami devices to EcoRI, whereas in unmethylated you can see restriction pattern, the methylated ones are protected. In the unmarked lanes to the left and right of the lane showing DNA exposed to EcoRI, there are controls and other enzymes which should not be cleaving. The first lane on the left is 1 Kb marker.

In contrast to mammalian genomes, which are ~75% methylated (Jabbari, K., Bernardi, 2004), neither the single stranded M13mp18 genome used as scaffold strand nor the synthetic short staple strands are methylated prior to folding. Therefore, we methylated the folded nanorobots in-vitro with a bacterial CpG methyltransferase (Cherepanova et al., 2011). While non-methylated nanorobots were cleaved as expected by bacterial restriction endonucleases, methylated ones were resistant to this treatment (FIG. 4).

Figure 5:
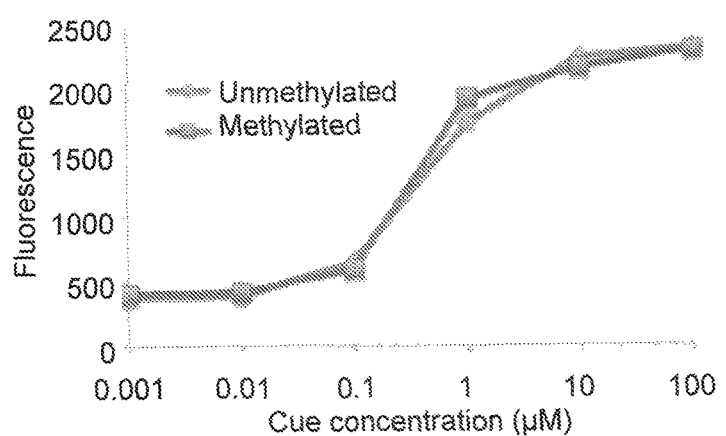
FIG. 5 shows that methylation of robots does not affect their ability to respond to cues. In this experiment, unmethylated and methylated robots were loaded with biotin and labeled fluorescently and incubated with increasing concentrations of cue (human PDGF), in the presence of streptavidin-coated microparticles.

FIG. 5 shows that methylation of robots does not affect their ability to respond to cues. In this experiment, unmethylated and methylated robots were loaded with biotin and labeled fluorescently and incubated with increasing concentrations of cue (human PDGF), in the presence of streptavidin-coated microparticles. After 2 hours, microparticles were analyzed by flow cytometry. Fluorescence intensity represents % open robots of the entire population, with maximum signal equivalent to ~85% of the population at plateau.

Figure 6:
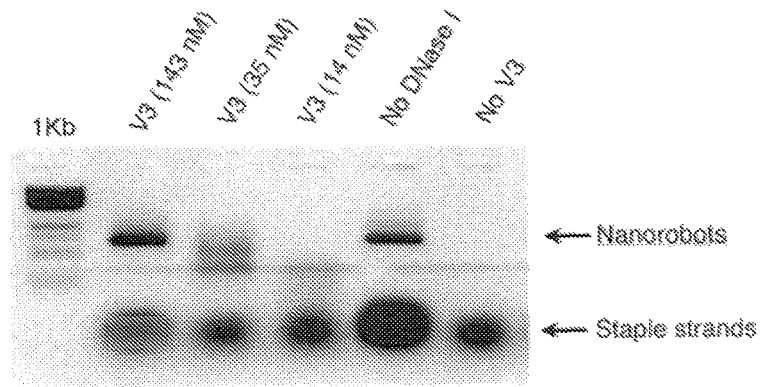
FIG. 6 depicts an agarose gel showing the response of a DNA origami device protected by V3 (netropsin) from DNase I. Increasing concentrations of netropsin protect the origami from DNase I (in 143 nM it is comparable to the sample without DNase I), whereas unprotected robots are completely digested (rightmost lane).
Figure 7:
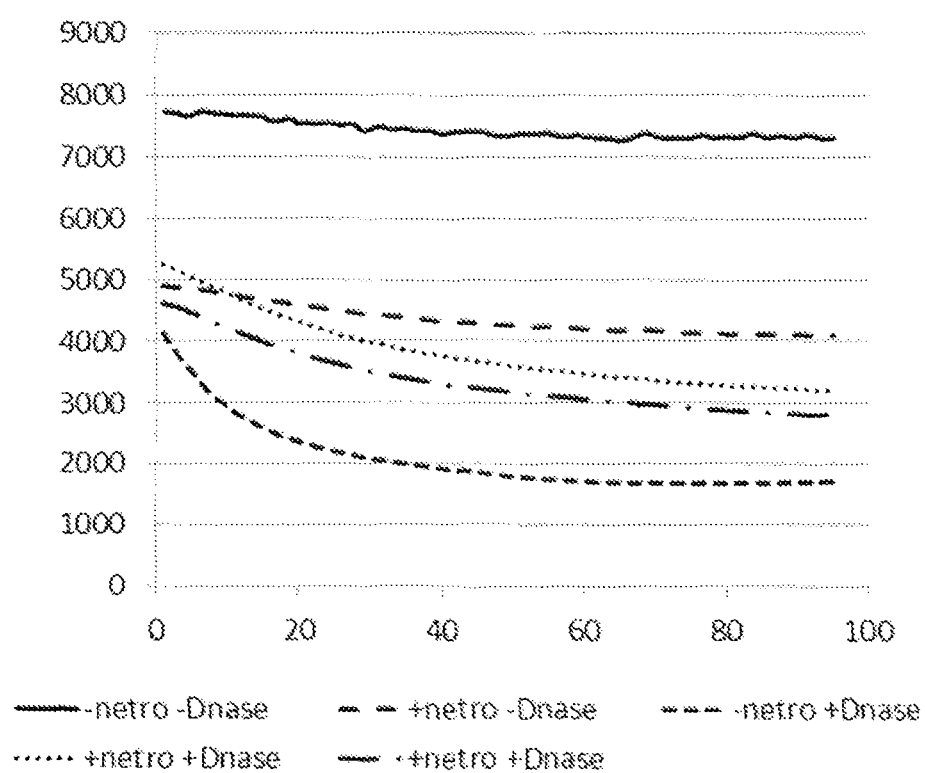
FIG. 7 shows a graph depicting the output of real time PCR. The four upper traces show amount of DNA (y-axis) in the presence of both Dnase and netropsin (netro), while the first trace from the bottom show amount of DNA in the absence of netropsin. The graph shows that netropsin when added to a DNA origami device inhibits DNase I digestion of the device.

In another example, we added netropsin to a DNA origami device and show that it inhibited DNase I digestion of the device (FIGS. 6 and 7).

Figure 8:
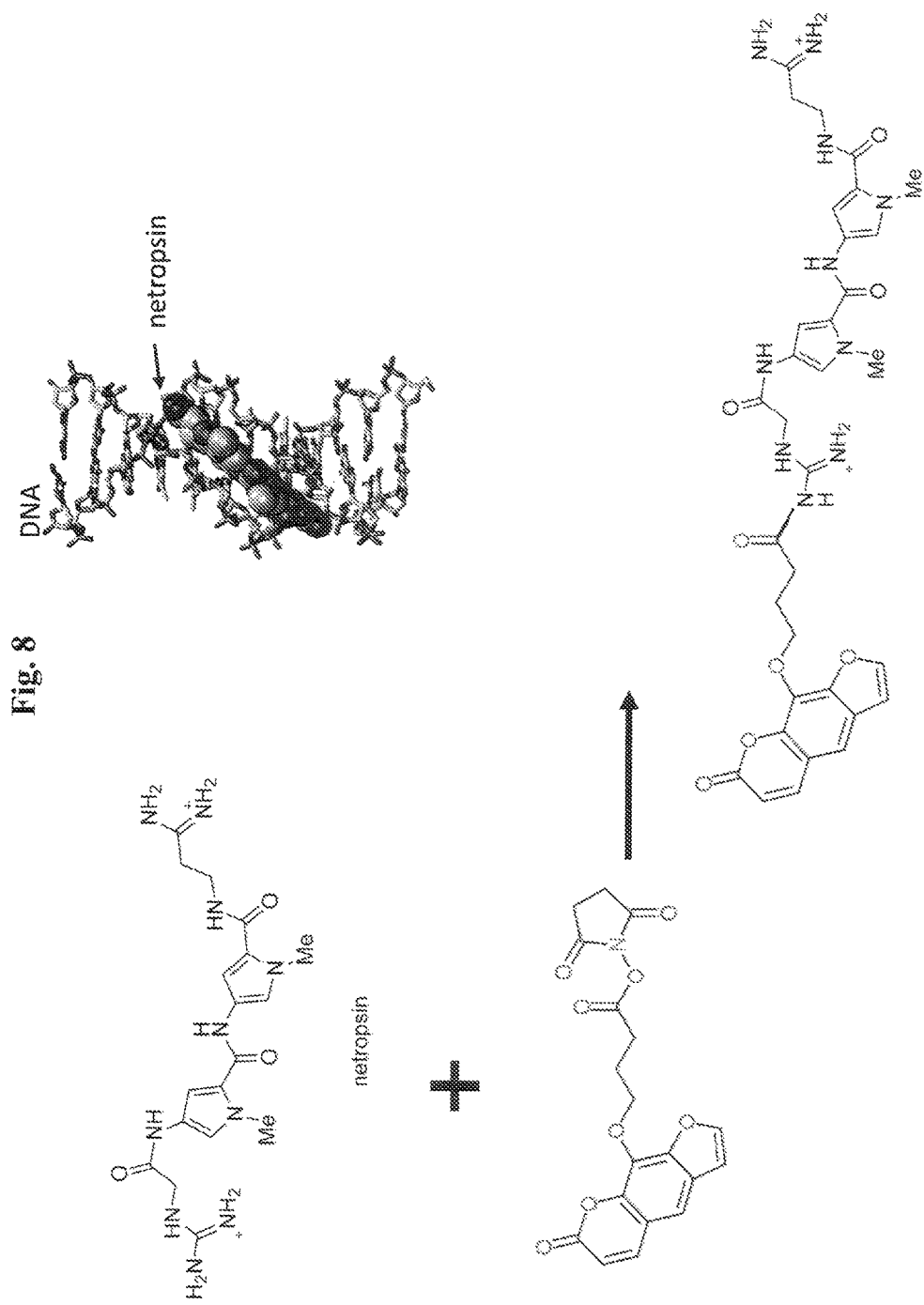
FIG. 8 depicts a scheme for attaching psoralene having a functional amino-reactive group to the termini of netropsin to enable covalent binding of netropsin to DNA.
Figure 9:
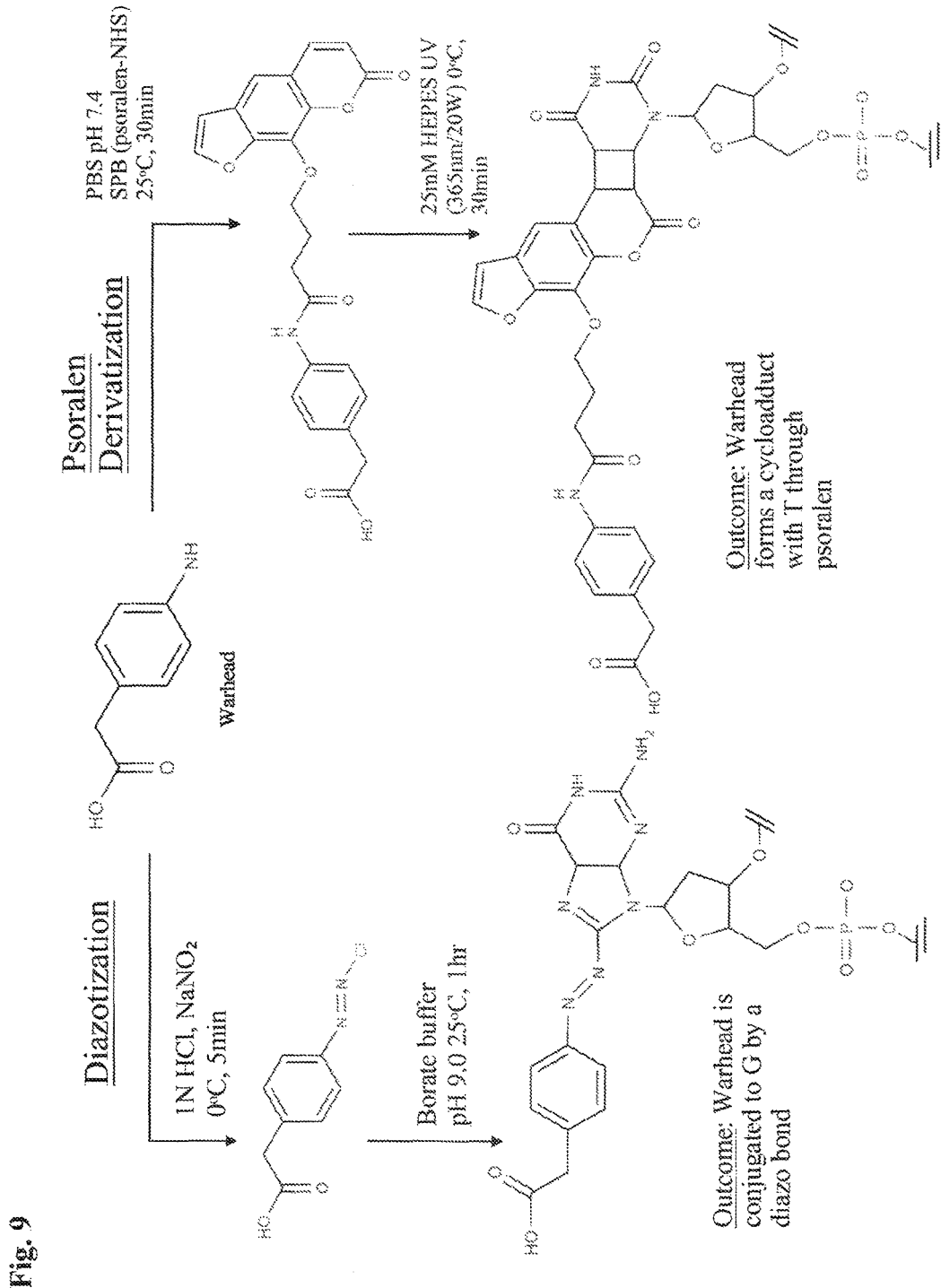
FIG. 9 shows three strategies for covalently linking a compound having amino group(s) to DNA, including the use of psoralene (middle scheme).
Figure 9:
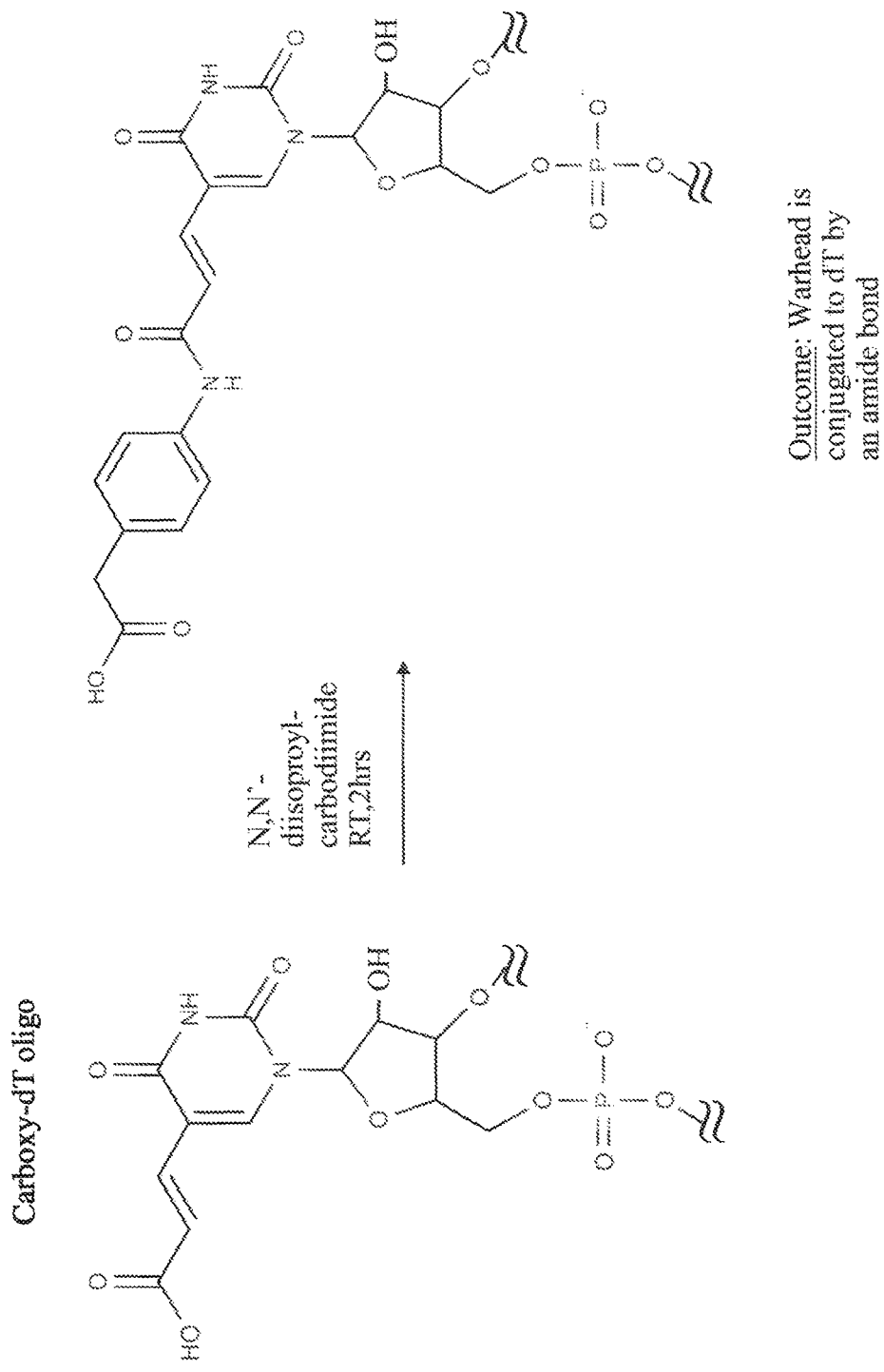

In order to prevent netropsin to leave the minor groove of the DNA, it was modified by adding to its termini a reagent capable of both reacting with amino groups on the netropsin peptide and with nucleoside bases of the DNA. In this specific case, psoralene was used as is shown in FIGS. 8 and 9.

Figure 10:
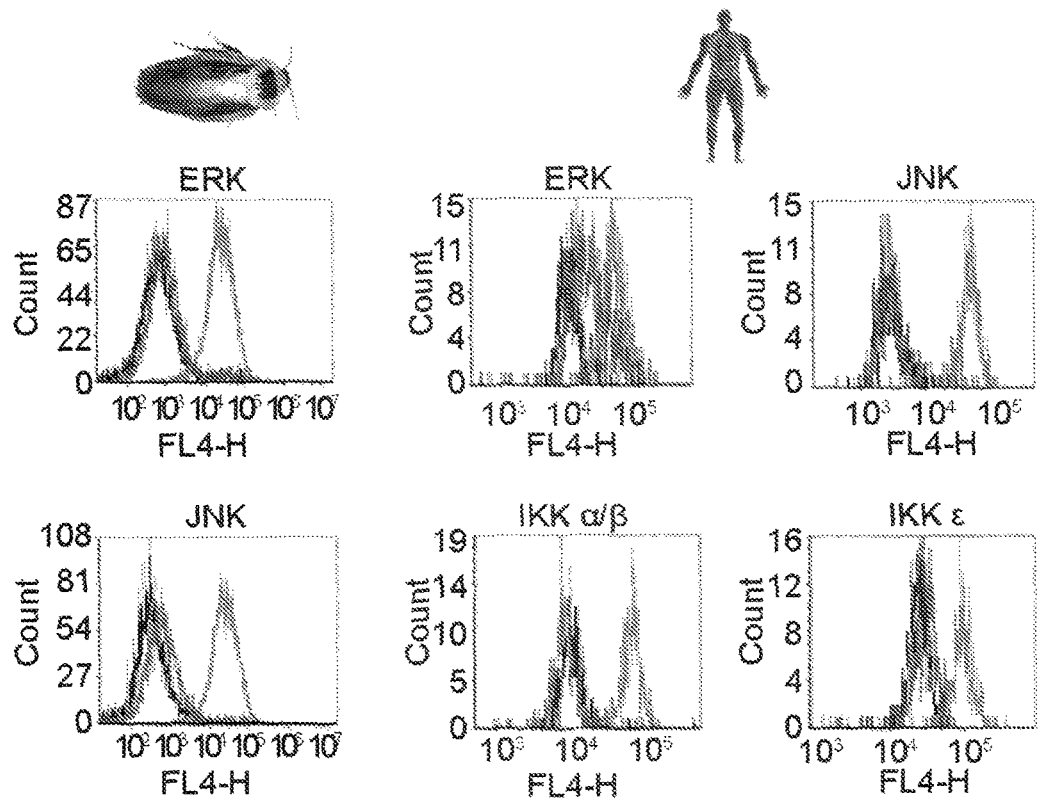
FIG. 10 shows fluorescent activated cell sorting (FACS) analysis of ex vivo phosphorylation of TLR9 downstream effectors in primary insect (*Blaberus discoidalis*) hemocytes and human macrophages exposed to unmethylated nanorobots, methylated nanorobots and saline. The two overlapping peaks to the left represent unmethylated nanorobots and saline, and the peak to the right represents methylated nanorobots.

(ii) Immunogenicity of nanorobots. The response of animal immune systems to nonmethylated CpG DNA has been observed in a diverse range of vertebrates and invertebrates (Hemmi et al., 2000; Sung et al., 2009; Sun et al., 2012; Kim et al., 2004; Silveira et al., 2012; Krieg et al., 1995). To examine the response of immune system cells to DNA origami, we exposed cells from three different origins—human macrophages, murine macrophages and primary insect (*Blaberus discoidalis*) hemocytes—to folded nanorobots. Exposure to non-methylated nanorobots resulted in phosphorylation of p42/44 ERK, IKK-α/β/ε, and SAPK/JNK, all indicative of TLR9-dependent activation (Lee et al., 2008; Lee et al., 2004) (FIG. 10). In contrast, no activation was observed after exposure to methylated nanorobots.

Figure 11A:
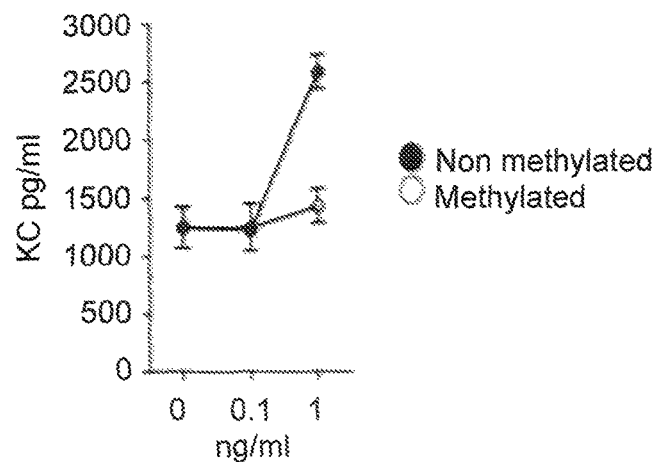
FIGS. 11A-C show that non-methylated—but not methylated—DNA origami devices activate murine immune cells. Methylated or non-methylated DNA origami was added to the cells and the response was examined by measuring cytokine and chemokine release by ELISA. A, KC (CXCL-1); B, CCL2; C, IL-6. X-axis, DNA origami device concentration.
Figure 11B:
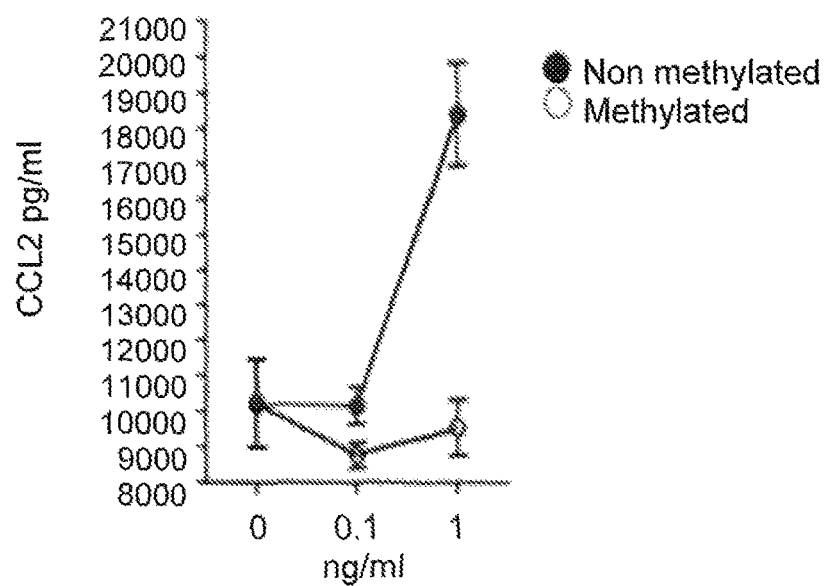
Figure 11C:
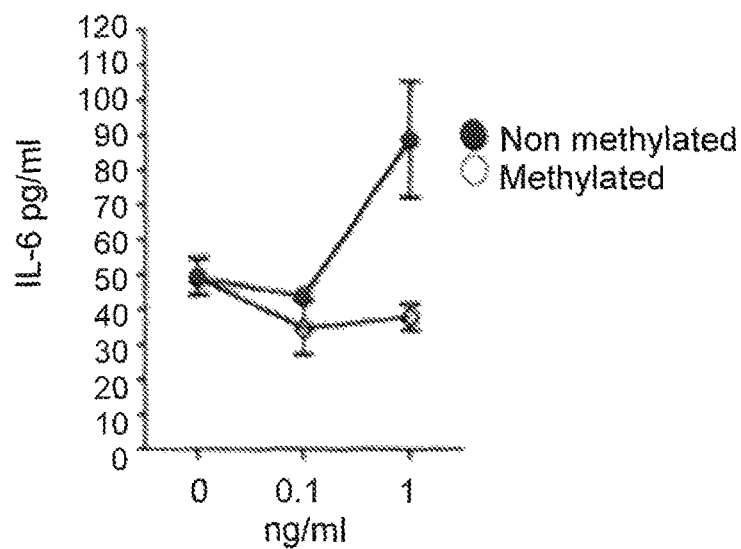
Figure 12A:
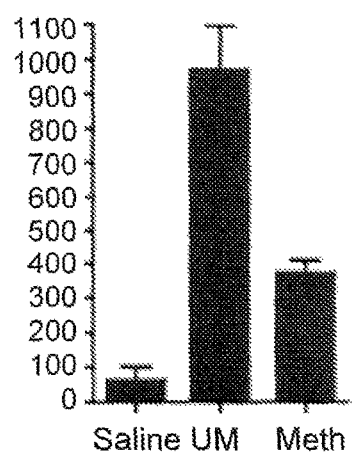
FIGS. 12A-B confirm that non-methylated—but not methylated—DNA origami devices activate murine immune cells. Methylated and non-methylated DNA origami was added to the cells and the response was examined by measuring cytokine CCL2 (A) and KC (CXCL-1; B) release by ELISA.
Figure 12B:
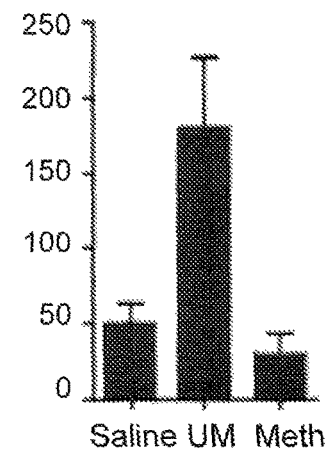

Cells exposed to nonmethylated nanorobots secreted the proinflammatory cytokine IL-6 and the chemokines CXCL-1 (KC) and CCL-2, while methylated nanorobots did not induce these mediators (FIG. 11).

Figure 13A:
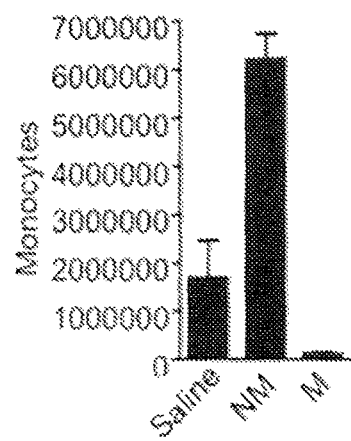
FIGS. 13A-B show cell count of monocytes (A) or macrophages (B) isolated 24 hrs after injection of 100 µg of nanorobots into the peritoneal cavity of 6-8 week old C57/BL6 mice. After methylated and nonmethylated nanorobots (M and NM, respectively) were injected i.p. to mice, total cell counts in the peritoneal fluid were done by flow cytometry.
Figure 13B:
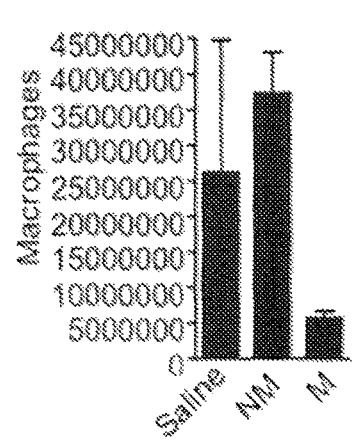

To evaluate the immune reaction triggered by the nanorobots in-vivo, we locally injected 100 μg of nanorobots into the peritoneal cavity of 6-8 week old C57/BL6 mice and tracked the response at 24 h following injection. Mice receiving methylated nanorobots did not show any recruitment of monocytes (FIG. 13A) or macrophages (FIG. 13B) and cytokine release.

The nanorobots may also be rendered non-immunogenic by modification of the DNA for example by attaching a macromolecule such as a polymer, a peptide, a lipid or a polysaccharide. The chemical reactions utilized for this purpose are well known in the art and are exemplified in FIG. 9.

Example 2

Remote-controlled DNA Origami Devices

Figure 14:
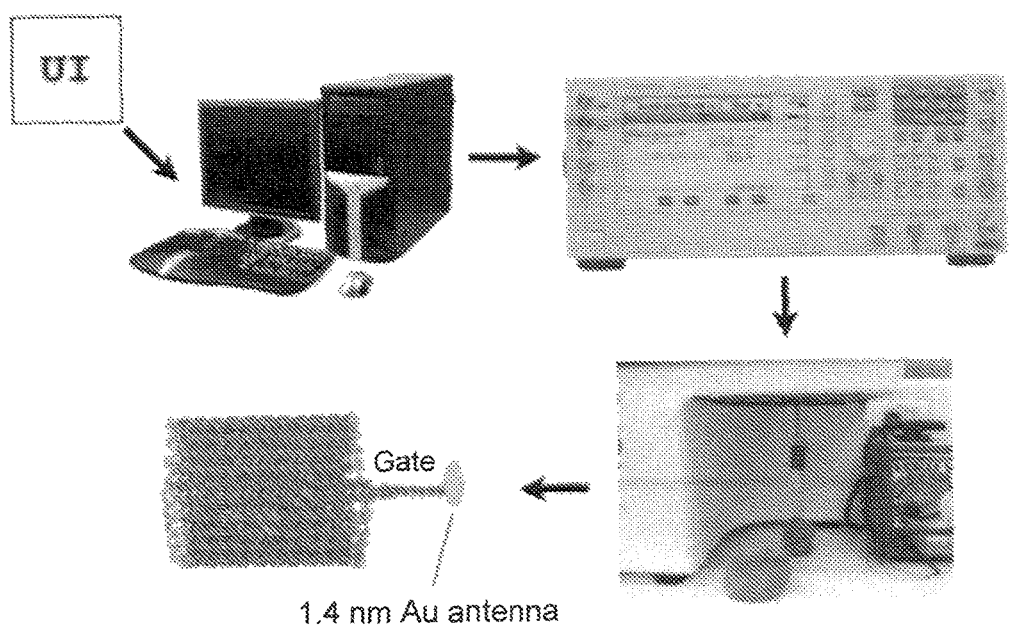
FIG. 14 depicts the setup for controlling an antenna-labeled nanorobot with electromagnetic field (EMF). The bottom left panel is a scheme of a nanorobot conjugated to the gold antenna through its gate strands. The bottom right panel depicts a copper coil used to generate the electromagnetic field. Upper right panel is the radio frequency (RF) signal generator that feeds 1 GHz RF into the coil, and this generator is controlled by the computer at the top left panel. UI, user interface.

The nanorobots of the present invention may be used in methods for controlling a DNA origami device by electronic remote control. The nanorobot is conjugated to a metal quantum dot, nanoparticle or a nanocrystal antenna (Hamad-Schifferli et al., 2002) (FIG. 14). The antenna-labeled nanobots were made by linking nanorobots with 1.4 nm-size gold nanocrystals functionalized with N-hydroxysuccinimidyl group, through reaction of the gold nanocrystals to amine-modified oligos serving as the device gates. The reaction itself was done in PBS in room temperature for 1 hour.

More specifically, the antenna is conjugated to the gate DNA strands controlling the device's state such that instead of opening when sensing a certain molecule, the device would open when an electromagnetic field (EMF) is applied to it, via inductive coupling of the antenna and subsequent heating of the gate until it melts (i.e. the two hybridized DNA strands that hold the robot closed dissociate from each other). The melting of the gate is reversible such that when an EMF is turned off, the device goes back to the off state (i.e. the two DNA strands re-hybridize).

Figure 15:
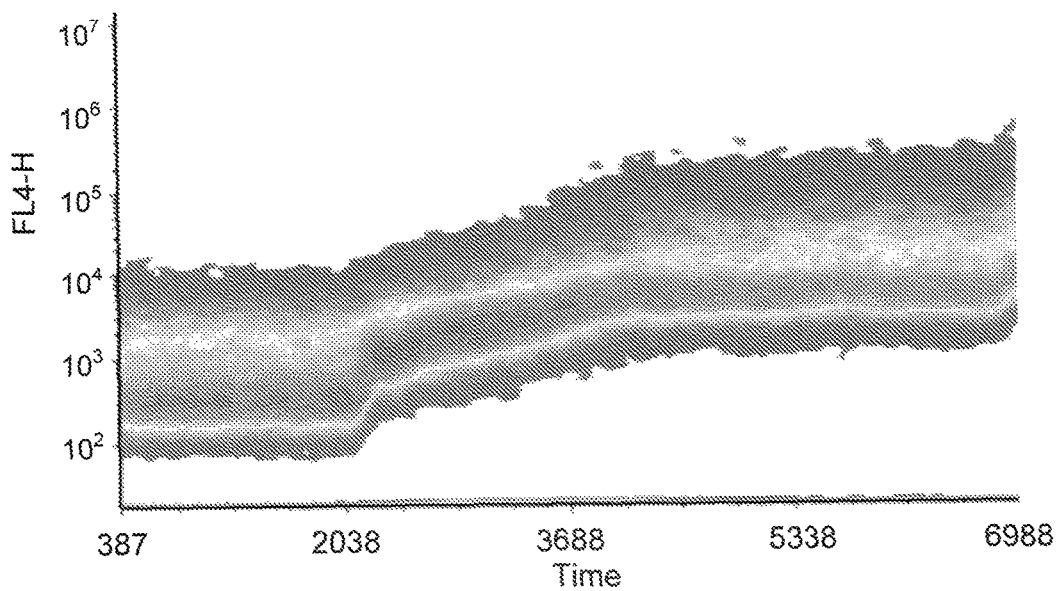
FIG. 15 shows a real time flow cytometric analysis of cells incubated with antenna-labeled DNA origami devices. At time=2038 the EMF is turned on, the DNA origami devices switch to on state and engage the cells with a fluorescent antibody. Color scale means cell density. X-axis shows time in $10^{-1}$ second units.
Figure 16:
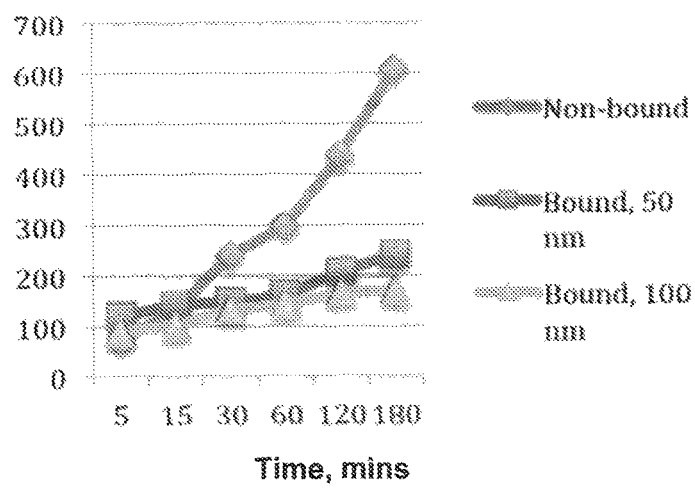
FIG. 16 shows the internalization of a fluorescent antibody by a target cell, when the antibody is not bound to any origami structure (diamonds), or when it is bound to 50 (squares) or 100 (triangles) nm-wide structure. X axis represents time in minutes; Y axis is fluorescence (arbitrary units).
Figure 17A:
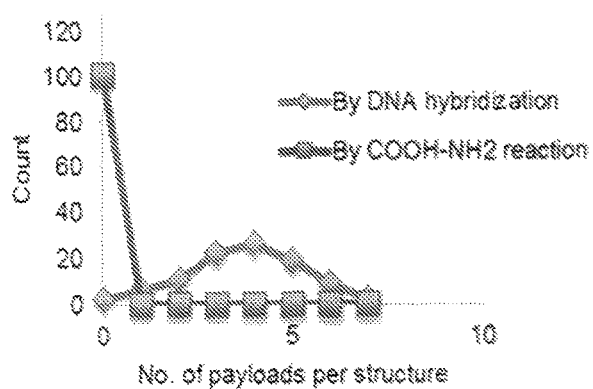
FIGS. 17A-B show that chemical reactions are prevented inside DNA origami structures. (A) a payload (5 nm gold nanoparticle, functionalized with either a DNA strand or carboxyl groups on its surface) is loaded inside a DNA origami structure by either hybridizing it with a complementary staple strand (diamonds), or by carbodiimide-aided conjugation of the carboxyl groups with amine-modified staple strands (squares). The former occurs normally while the latter does not. Structures were counted in TEM (B).
Figure 17B:
Figure 18:
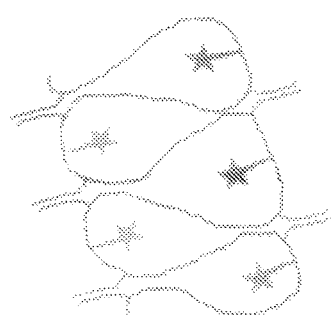
FIG. 18 depicts a schematic representation of a multimodal DNA origami device that consists of a 2D sheet (blue long folded continues line) folded into compartments, each compartment controlled separately by a dsDNA gate (small colored arms protruding outwards). A different payload (drug, protein, nucleic acid, nanoparticle etc.) is attached inside every compartment (colored stars).

A real time flow cytometric analysis of cells incubated with DNA origami devices configured as described above show that when the EMF is turned on, the DNA origami devices switch to on state and engage the cells with a fluorescent antibody (FIG. 15). The cells are freshly isolated insect cells. The robots (0.1 pmol) were mixed with the cells in a 0.5 ml volume, and data was acquired in real time in the fluorescent activated cell sorting (FACS) machine. At the designated time point, EMF was activated which led to the robots opening and the loaded antibody attaching to the cells—which as a result increased in fluorescence measured by the FACS.

Example 3

A Method for Programmable Prevention of Internalization of Cell Surface Binding Molecules We present a system that prevents or inhibits the internalization of a molecule binding to a cell surface receptor. This is affected by the attachment of a large 2D sheet, 2D band or 3D shape of DNA origami (up to 1 micron in one dimension) to the molecule that binds to a cell surface receptor. The size of the DNA structure can vary according to cell type, based on the known data regarding the size of clathrin-coated pits for endocytosis (ranging from 25 to ~180 nm). Cell surface receptors normally undergo internalization by endocytosis; however, the process cannot occur or is drastically hindered by the addition of the DNA molecule.

The size of the DNA origami attachment object can be programmed to yield a specific rate of internalization of the molecule it is attached to. The DNA origami attachment object can be decorated with molecules that further modify its ability to prevent/inhibit internalization (e.g., negatively-charged polysaccharides, negatively-charged proteins, polymers, nanoparticles etc.).

In this experiment we demonstrate the internalization of a fluorescent antibody by a target cell, when the antibody is not bound to any origami structure, or when it is bound to 50 or 100 nm-wide structure (FIG. 15). A fluorescently-tagged antibody was linked to a DNA origami structure via an amine-modified staple oligonucleotide. The structure is either a closed robot (50 nm) or an open one (100 nm). For this experiment, robot state was predetermined, however it is understood that the robot state (and therefore its internalization-modifying effect) can be determined by environmental cues. Cell fluorescence was acquired after washing the cells from surface bound molecules, leaving only cell-internalized molecules representing the phagocytosis of the antibody. Cells were U937 macrophage cell line. While an unmodified antibody was internalized very efficiently by the U937 cells, attaching it to the DNA origami structure suppressed this internalization (by ~88% at closed state, 96% at open state, no significant differences were found between state-driven effects). This shows that DNA origami can be used as a modification that can be linked to molecules (chemicals, biologicals, and inorganic compounds) to modulate how they are taken up by living cells.

Example 4

A Method for Increasing Vaccine Shelf Life

Preliminary experiments conducted in our laboratory showed that certain chemical reactions, such as carboxyl-amine condensation, do not occur when the reaction is fixed inside a hollow DNA origami structure, while proceeding normally on the outside (FIGS. 16A-B). This led to the hypothesis that the folding of a large amount of DNA into a very limited 3D space, about $10^3$-$10^4$ fold smaller, creates an extremely unusual chemical nanoenvironment within that space.

The consequence of this unusual chemical nanoenvironment is the protection of macromolecules from degradation caused by chemical reactions such as dehydration (e.g., by carbodiimide), oxidation, hydrolysis, etc.

We present a method for extending the shelf life of an active agent by increasing its resistance to spontaneous or catalyzed chemical degradation in solution in ambient conditions. These active agents could be drugs, small molecule chemicals, vaccines, proteins, antibodies, RNA or other nucleic acid therapeutic drugs. Examples of vaccines with extremely short shelf life are listed in Table 1.

The method is based on addition of a hollow DNA origami tube-like structure to vaccines. The vaccine molecule can be either attached or not attached to the structure Attachment of the vaccine to the structure can occur either at the middle part of the structure, at the edge of the structure or anywhere in between.

The structure can have any length up to 500 nm and internal diameter of between 2-100 nm.

TABLE 1 vaccines with limited stability

| Vaccine | Disease | Stability in 25° C. |
|---|---|---|
| DUKORAL | Cholera | 14 days |
| HAVRIX | Hepatitis A | 72 hours |
| ENGERIX | Hepatitis B | 72 hours |
| CERVARIX | HPV | 1-7 days |
| SYNFLORIX | Pneumococcus | 1-3 days |
| ROTATEQ | Rotavirus | 12-48 hours |
| TYPHERIX | Typhoid | 72 hours |
| VARIVAX | Varicella | 6 hours at 27° C. |

The structure is decorated internally or externally with additional molecules or particles (proteins, nanoparticles, lipids, etc.), which may alter the natural charge density of the DNA origami structure.

The DNA origami structure is added to the active agent such that inside the structure certain chemical reactions cannot occur due to folding and packing of many negative charges into a very small space.

The DNA origami structure can be designed using an algorithm for crystal growth that minimizes asymmetric branching.

Example 5

Multimodal DNA Origami Devices

We present a novel design of DNA origami devices, which can respond to different cues by generating different outputs, rather than turn one molecule on or off. This DNA origami device can control multiple payloads separately by means of being designed as a multichamber container with each chamber separate and independent from others.

The device has the general design shown in FIG. 18.

The device consists of a 2D sheet (blue) folded into compartments, each compartment controlled separately by a dsDNA gate. A different payload (drug, protein, nucleic acid, nanoparticle etc.) is attached inside every compartment.

The design of the device is such that only when a gate controlling a particular compartment opens, the compartment unfolds to expose its particular payload. Furthermore, the gates are such that each gate recognizes a particular cue (molecule, chemical or physical condition, RF signal etc.), and they are reversible. The two or more compartments can open simultaneously when the cues opening their gates exist simultaneously.

Example 6

Glucose-sensitive DNA Origami Device

Nanobots that open or close at physiologically relevant glucose concentrations were prepared as described above, i.e. nanorobots in which one of the staple strands comprises an aptamer domain capable of binding glucokinase having a first configuration, i.e. a configuration at glucose concentration ranging between 0-4.5 mM, but incapable of binding to the glucokinase having a second configuration, i.e. a glucose concentration ranging between 5-10 mM; and another of the staple strands comprises a latch domain linked to the glucokinase.

Figure 19A:
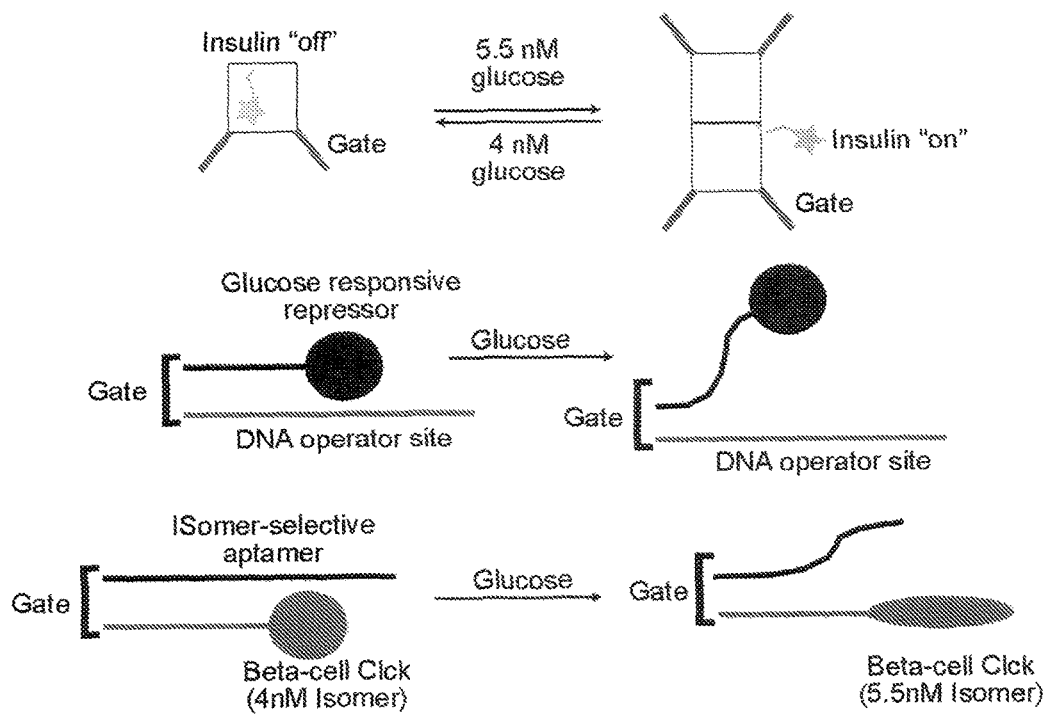
FIGS. 19A-B depict glucose-sensitive nanorobots and their function. A. A scheme of the structure of glucose-sensitive nanorobots having insulin as a cargo and a gate comprising a glucose-binding protein and an oligonucleotide, the former being capable of binding the latter only at certain glucose concentrations. The glucose-binding protein may be a glucose responsive repressor, a DNA-binding protein that binds a DNA operator site of a certain sequence (being part of the gate) at low—but not at a high—glucose concentration. Alternatively, the glucose-binding protein may be a glucokinase (Beta-cell G1cK) that is bound by an iso-selective aptamer (being part of the gate) that binds to it at low—but not at a high—glucose concentration. When the gate opens at high glucose concentration, the nanorobot opens and insulin is exposed. B. An agarose gel that shows that insulin bound to DNA robots successfully activates the insulin receptor on liver cells. pAkt—phosphorylated serine/threonine kinase akt. Actin is shown for (a stable) reference. Three left-most lanes, empty robots lacking insulin; three middle lanes, robots loaded with insulin that are constantly open; three right-most lanes, robots loaded with insulin that are opened by an external DNA key.

The concept of how the nanorobots react to different glucose concentrations is shown in FIG. 19A. The nanorobots of the invention also carry a fluorophores-quencher pair (using the bright tCY5 or CY5.5 fluorescent dyes and dark quencher compatible with these wavelengths) located such that the pair reports the robot state, i.e. when the robot is closed, signal is quenched and no fluorescence is emitted, however when the robot is open, it emits fluorescence.

Figure 19B:
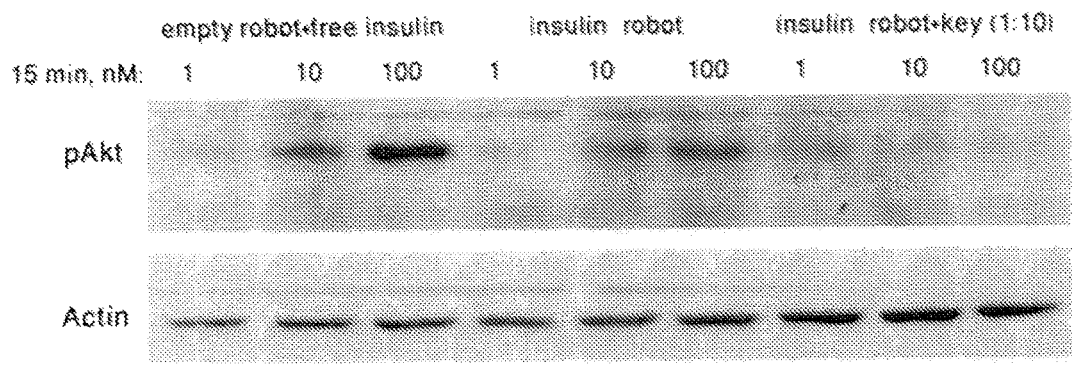

An in vitro experiment shows that insulin bound to DNA robots successfully activates the insulin receptor on liver cells (FIG. 19B). Robots loaded with insulin (insulin bound to DNA complementary to loading sequence through the second-terminal lysine residue) were either constantly open or closed but activated with an external DNA key opening their gates. Akt phosphorylation measured in liver cells activated with both robot types showed insulin-dependent activation. The purpose of this experiment was to verify that insulin bound to the DNA origami chassis can still activate insulin receptors and lead to the proper signal in the target cells.

Example 7

Treatment of Diabetes

An accepted diabetes type I animal is used as disclosed for example in Buschard (1996) Acta Pathologia, Microbiologica Et Immunologica Scandinavia 104: 609-604. For example, spontaneously diabetic BB rats, NOD mice, or virus-induced diabetes in mice may be used.

The nanorobot of the invention as described in Example 6, which is sensitive to glucose concentration, is administered to the experimental animal at different stages of the disease and at different regiments.

A glucose tolerance test is performed in which glucose is provided to the animals and blood samples are taken afterward to determine how quickly it is cleared from the blood in the presence or absence of glucose-sensitive nanorobots of the invention.

As stated above, the nanorobots of the invention also carry a fluorophores-quencher pair located such that the pair reports the robot state, i.e. when the robot is closed, signal is quenched and no fluorescence is emitted, however when the robot is open, it emits fluorescence. Thus, in addition to glucose measurement, we measure robot-generated fluorescence in the blood to correlate a change in glucose levels with the response of the robots.

It is expected that robots loaded with insulin will activate cells in vivo in the rodent models of type I diabetes. It is expected that a lower frequency of administration of the insulin-loaded robots may be obtained as compared with the regiment of free insulin administration and that the administration regiment is independent on the feeding schedule of the animals, since the robots intrinsically provide the insulin to the cells at relevant glucose levels.

Example 8

Figure 20B:
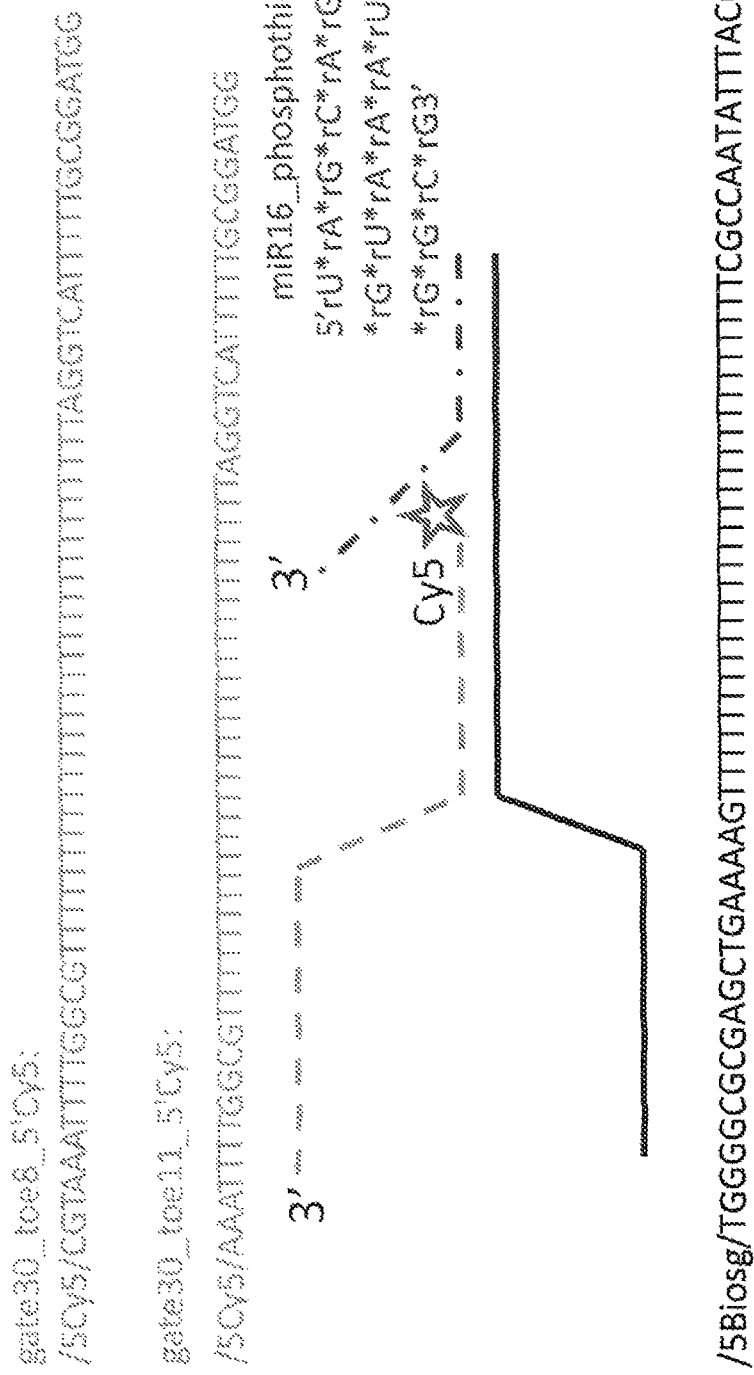

Asimov Monotype Nanobots—Closure of Active Nanobots in Response to External Cue Robots were folded using the scheme shown in FIGS. 20A-B. Gate strands (dashed lines; SEQ ID NOs: 281 and 282) were tagged with CY5 fluorescent dye. Complementary strands (dash-dotted lines; SEQ ID NO: 283) were designed to contain an either 8-nt or 11-nt toehold region that hybridizes with a damage indicator molecule (dotted line). In this experiment, microRNA-16 (miR-16; SEQ ID NO: 284) was selected. miR-16 leaks from damaged cells and enables identification of the damaged cell type (as miR-16 concentration depends on cell type).

Robots were loaded with biotin, such that open robots engaged and stained streptavidin-coated microbeads. High bead fluorescence indicates open robots. Low fluorescence indicates closed robots. A decrease in fluorescence therefore represents a process of robot closure.

Presence of miR-16 in varying concentrations successfully displaced the black strand from the orange strand (as shown above), and induced a decrease in microbead fluorescence. This closure of robots resulted from hybridization of the dashed and dash-dotted strands (dash-dotted is not shown here but the process symmetrically occurs on the bottom side of the robot—the dash-dotted strand is just the top side).

Figure 20C:
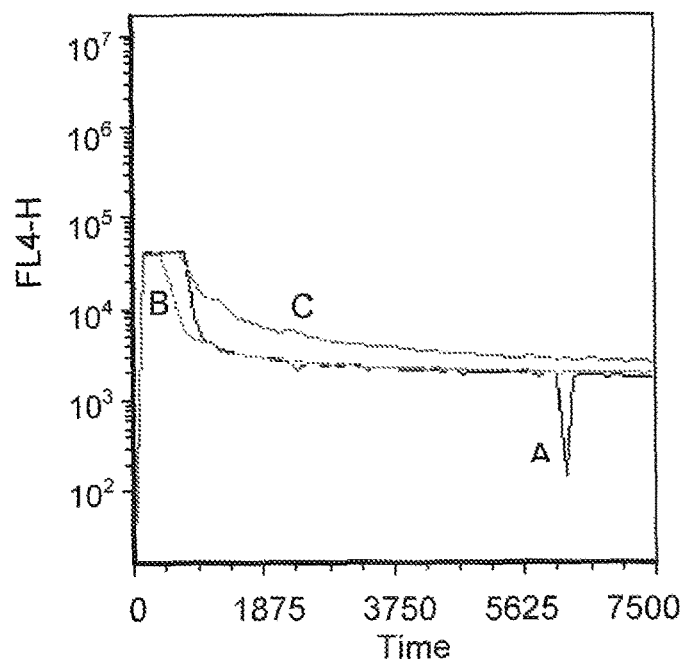
Figure 20D:
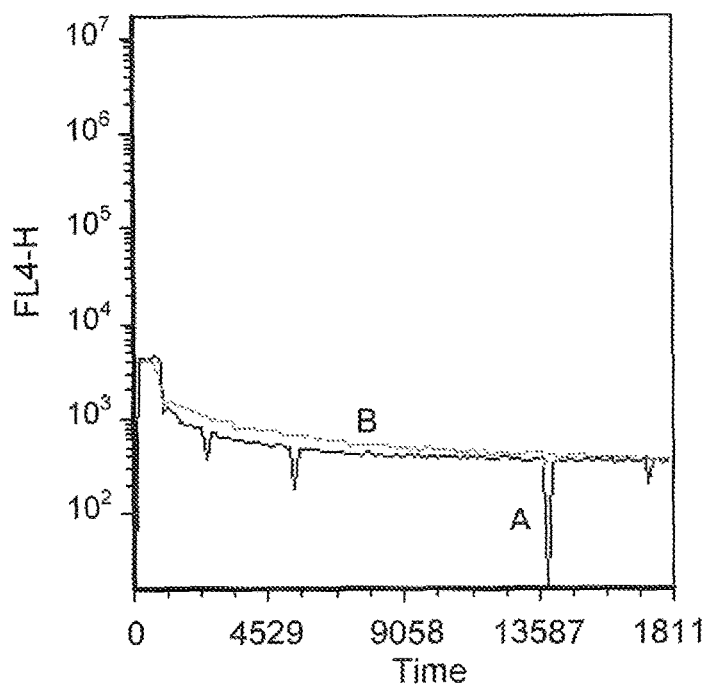

Robots closing in response to miR-16 at varying concentrations are shown in FIG. 20C. Open robots expose biotin and therefore attach and tag streptavidin-coated microbeads. Closed robots cannot attach to the beads. In response to miR-16, a decrease in fluorescence can be seen. This results from free biotin in the solution competing more successfully with robots being closed rather than the robots that are completely open. A comparison between the kinetics of the robots having an 8nt or lint toehold shows that it is possible to tune the response speed, which is critical because in some applications one want it to be more permissive and in other more restrictive.

REFERENCES

Bell, N. A., Engst, C. R., Ablay, M., Divitini, G., Ducati, C., Liedl, T., Keyser, U. F., DNA origami nanopores. *Nano Letters*, 2012, 12, 512-517

Cherepanova, N. A., Minero, A. S., Rakhimova, A. R., Gromova, E. S., Mechanism of CpG DNA methyltransferases M.SssI and Dnmt3a studied by DNA containing 2-aminopurine. *Nucleosides, nucleotides & nucleic acids*, 2011, 30, 619-631

Christensen, S. R., Kashgarian, M., Alexopoulou, L., Flavell, R. A., Akira, S., Shlomchik, M. J., Toll-like receptor 9 controls anti-DNA autoantibody production in murine lupus. *The Journal of experimental medicine*, 2005, 202, 321-331

Dietz, H., Douglas, S. M., Shih, W. M., Folding DNA into twisted and curved nanoscale shapes. *Science*, 2009, 325, 725-730

Douglas, S. M., Dietz, H., Liedl, T., Högberg, B., Graf, F., Shih, W. M., Self-assembly of DNA into nanoscale three-dimensional shapes. *Nature*, 2009a, 459, 414-418

Douglas, S. M., Marblestone, A. H., Teerapittayanon, S., Vazquez, A., Church, G. M., Shih, W. M., Rapid prototyping of 3D DNA-origami shapes with caDNAno. *Nucleic Acids Research*, 2009b, 37, 5001-5006

Douglas, S. M., Bachelet, I., Church, G. M., A logic-gated nanorobot for targeted transport of molecular payloads. *Science*, 2012, 335, 831-834

Hamad-Schifferli, K., Schwartz, J. J., Santos, A. T., Zhang, S., Jacobson, J. M., Remote electronic control of DNA hybridization through inductive coupling to an attached metal nanocrystal antenna. *Nature*, 2002, 415, 152-155

Hemmi, H., Takeuchi, O., Kawai, T., Kaisho, T., Sato, S., Sanjo, H., Matsumoto, M., Hoshino, K., Wagner, H., Takeda, K., Akira, S., A Toll-like receptor recognizes bacterial DNA. *Nature*, 2000, 408, 740-745

Jabbari, K., Bernardi, G. Cytosine methylation and CpG, TpG (CpA) and TpA frequencies. *Gene*, 2004, 333, 143-149

Jones, P. A., Functions of DNA methylation: islands, start sites, gene bodies and beyond. *Nature reviews. Genetics*, 2012, 13, 484-492

Jungmann, R., Scheible, M., Simmel, F. C., Nanoscale imaging in DNA nanotechnology. *Wiley Interdisciplinary Reviews: Nanomedicine and Nanobiotechnology*, 2012, 4, 66-81

Jungmann, R., Steinhauer C., Scheible M., Kuzyk, A., Tinnefeld, P., Simmel, F. C., Single-molecule kinetics and super-resolution microscopy by fluorescence imaging of transient binding on DNA origami. *Nano Letters*, 2010, 10, 4756-4761

Kim I., Kim S. H., Lee Y. S., Yun E. K., Lee H. S., Kim J. W., Ryu K. S., Kang P. D., Lee I. H., Immune stimulation in the silkworm, *Bombyx mori* L., by CpG oligodeoxynucleotides. *Archives of insect biochemistry and physiology*, 2004, 55, 43-48

Kuzyk, A., Schreiber, R., Fan, Z., Pardatscher, G, Roller, E., Hogele, A., Simmel, F. C., Govorov, A. O., Liedl, T., DNA-based self-assembly of chiral plasmonic nanostructures with tailored optical response. *Nature*, 2012, 483, 311-314

Krieg, A. M., Yi, A., Matson, S., Waldschmidt, T. J., Bishop, G. A., Teasdale, R., Koretzky, G. A., Kilnman, D. M., CpG motifs in bacterial DNA trigger direct B-cell activation. *Nature*, 1995, 374, 546-549

Lee, J. G., Lee, S. H., Park, D. W., Lee, S. H., Yoon, H. S., Chin, B. R., Kim, J. H., Kim, J. R., Baek, S. H., Toll-like receptor 9-stimulated monocyte chemoattractant protein-1 is mediated via JNK-cytosolic phospholipase A2-ROS signaling. *Cellular signalling*, 2008, 20, 105-111

Lee, S., Hong, J., Choi, S. Y., Oh, S. B., Park, K., Kim, J. S., Karin, M., Lee, S. J., CpG oligodeoxynucleotides induce expression of proinflammatory cytokines and chemokines in astrocytes: the role of c-Jun N-terminal kinase in CpG ODN-mediated NF-kappaB activation. *Journal of neuroimmunology*, 2004, 153, 50-63

Rothemund, P. W., Folding DNA to create nanoscale shapes and patterns. *Nature*, 2006, 440, 297-302

Schüller, V. J., Heidegger, S., Sandholzer, N., Nickels, P. C., Suhartha, N. A., Endres, S., Bourquin, C., Liedl, T., Cellular immunostimulation by CpG-sequence-coated DNA origami structures. *ACS Nano*, 2011, 5, 9696-9702

Schreiber, R., Kempter, S., Holler, S., Schüller, V., Schiffels, D., Simmel, S. S., Nickels, P. C., Liedl, T., DNA origami-templated growth of arbitrarily shaped metal nanoparticles. *Small*, 2011, 7, 1795-1799

Silveira, H., Gabriel, A., Ramos, S., Palma, J., Felix, R., Custódio, A., Collins, L. V., CpG-containing oligodeoxynucleotides increases resistance of *Anopheles* mosquitoes to *Plasmodium* infection. *Insect biochemistry and molecular biology*, 2012, 42, 758-765

Steinhauer, C., et al., DNA origami as a nanoscopic ruler for super-resolution microscopy. *Angewandte Chemie International Edition.*, 2009, 48, 8870-8873

Sun, R., et al., Hemocytic immune responses triggered by CpG ODNs in shrimp *Litopenaeus vannamei. Fish & shellfish immunology*, 2013, 34, 38-45

Sung, H. H., Yang, C. W., Lin, Y. H., Chang, P. T., The effect of two CpG oligodeoxynucleotides with different sequences on haemocytic immune responses of giant freshwater prawn, *Macrobrachium rosenbergii. Fish & shellfish immunology*, 2009, 26, 256-263

---

The invention claimed is:

1. A nucleic acid origami device comprising a scaffold strand and a plurality of staple strands, having the structure A, B C or D, wherein:

in the structure A:

(i) one of the staple strands comprises either (a) an aptamer domain capable of binding to a binding partner; (b) an oligonucleotide capable of binding a DNA binding protein; or (c) an oligonucleotide attached to a nano-antenna capable of receiving an electromagnetic field, or one of the staple strands comprises an aptamer domain of (a) and another of the staple strands comprises an oligonucleotide of (b) or (c);

(ii) another of the staple strands comprises a latch domain hybridized or bound to said aptamer domain of (a) or oligonucleotide of (b) or (c), the latch domain sequence being selected such that the aptamer domain of (a) is capable of binding to the binding partner such that the binding partner displaces the latch domain, or the latch domain is capable of hybridizing with an external oligonucleotide selected such that the external oligonucleotide displaces the aptamer domain; said latch domain is linked to a binding partner that is selected such that it has a first configuration under a first condition and a different second configuration under a different second condition, and the aptamer of (a) or the oligonucleotide of (b) is capable of binding to the binding partner having the first configuration but incapable of binding to the binding partner having the second configuration such that the latch domain is displaced from the aptamer of (a) or the oligonucleotide of (b) when the binding partner transitions from the first to the second configuration; or the nano-antenna of (c), upon receipt of said electromagnetic field, undergoes inductive coupling and subsequent heating thereby displacing the latch domain from the oligonucleotide of (c); and (iii) the aptamer domain of (a) or the oligonucleotide of (b) or (c), and the latch domain, when hybridized or bound to one another, hold the device in a closed configuration; and the device transitions to an open configuration when said aptamer domain or oligonucleotide, and the latch domain, are not hybridized or bound to one another, in the structure B:

(i) one of the staple strands comprises a first aptamer domain capable of binding to a first binding partner;

(ii) another of the staple strands comprises a second aptamer domain capable of binding to a second binding partner;

(iii) still another of the staple strands comprises a first latch domain hybridized to the first aptamer domain, the sequence of the first latch domain being selected such that the first aptamer domain is capable of binding to the first binding partner such that the first binding partner displaces the first latch domain, or the first latch domain is capable of hybridizing with an external oligonucleotide selected such that the external oligonucleotide displaces the first aptamer domain;

(iv) yet another of the staple strands comprises a second latch domain hybridized to the second aptamer domain, the second latch domain sequence being selected such that the second aptamer domain is capable of binding to the second binding partner such that the second binding partner displaces the second latch domain, or the second latch domain is capable of hybridizing with an external oligonucleotide selected such that the external oligonucleotide displaces the second aptamer domain; and (v) said nucleic acid origami device is in a closed configuration when the first aptamer domain is hybridized to the first latch domain and/or the second aptamer domain is hybridized to the second latch domain; and the device transitions to an open configuration when the first aptamer domain is not hybridized to the first latch domain and the second aptamer domain is not hybridized to the second latch domain, in the structure C:

(i) two of the staple strands each comprises a latch domain linked to an oligonucleotide capable of hybridizing with an external oligonucleotide; and said nucleic acid origami device is in an open configuration when each oligonucleotide capable of hybridizing with an external oligonucleotide is not hybridized to said external oligonucleotide; and the device transitions to a closed configuration when each oligonucleotide capable of hybridizing with an external oligonucleotide is hybridized to each one of said external oligonucleotide, in the structure D;
- (i) one of the staple strands comprises an intrinsic oligonucleotide capable of hybridizing with an external soluble oligonucleotide and an oligonucleotide linked to a latch domain;
- (ii) two of the staple strands each comprises a latch domain linked to a first or a second oligonucleotide, wherein the first oligonucleotide is capable of hybridizing to the second oligonucleotide and to the intrinsic oligonucleotide;
- (iii) each one of the first and second oligonucleotide is hybridized to one intrinsic oligonucleotide and is selected such that the intrinsic oligonucleotide is capable of hybridizing to the external soluble oligonucleotide such that the external soluble oligonucleotide displaces the intrinsic oligonucleotide and the first and second oligonucleotide hybridize to each other; and
- (iv) said nucleic acid origami device is in an open configuration when each one of the first and second oligonucleotide is hybridized to said intrinsic oligonucleotide; and the device transitions to a closed configuration when the first and second oligonucleotide is not hybridized to said intrinsic oligonucleotide and is instead hybridized to each other, wherein
said nucleic acid origami device is either alkylated, acylated or hydroxylated, or interacts with a compound capable of non-covalently binding to the major- or minor-groove of a double stranded nucleic acid, and therefore is resistant to nucleases, and/or
said nucleic acid origami device lacks TLR9 recognition elements or the TLR9 recognition elements of said nucleic acid origami device are masked or modified and therefore said nucleic acid origami device is non-immunogenic.

2. The nucleic acid origami device of claim 1, wherein said device is non-immunogenic and/or resistant to nucleases.

3. The nucleic acid origami device of claim 1, wherein said nucleic acid origami device is methylated DNA.

4. The nucleic acid origami device of claim 1, wherein said compound capable of non-covalently binding to the major- or minor-groove of a double stranded nucleic acid is selected from the group consisting of netropsin, distamycin, an oligoamide, a sugar-oligoamide conjugate and a bis-amidine.

5. The nucleic acid origami device of claim 1, wherein one or more further staple strands each comprises a handle domain bound to a payload, optionally via a linker.

6. The nucleic acid origami device of claim 5, wherein said linker comprises an oligonucleotide having a sequence complementary to the sequence of the handle domain and optionally comprising a further domain comprising a recognition site for enzymatic cleavage, and the payload is bound to the handle domain through the hybridization of the oligonucleotide to the handle domain, or wherein said linker comprises a protein capable of binding a small molecule.

7. The nucleic acid origami device of claim 6, wherein said linker comprises an oligonucleotide having a sequence complementary to the sequence of the handle domain and a further domain comprising a recognition site for enzymatic cleavage, and the payload is bound to the handle domain through the hybridization of the oligonucleotide to the handle domain, said further domain comprises a peptide linker comprising a protease recognition site for cleavage by a protease.

8. The nucleic acid origami device of claim 5, wherein said payload is a drug selected from the group consisting of insulin, an antibody or a fragment thereof, a cell surface receptor ligand or a biologically active fragment thereof, a small molecule, a nucleic acid such as an oligonucleotide, a nuclease, an aptamer, a lipid, a glycan, a protein, a glycoprotein, a glycolipid, a nanoparticle, a fluorophore, a radioactive compound, a nano-antenna and a liposome.

9. The nucleic acid origami device of claim 5, wherein the plurality of staple strands are selected such that at least one of the one or more staple strands comprising a payload is positioned on an inner surface of the nucleic acid origami device when the device is in the closed configuration; and the transition to the open configuration causes said payload to be positioned on an outer surface of the nucleic acid origami device or; wherein one of the staple strands comprises a handle domain positioned on an outer surface of the device when the device is in the closed configuration; and the transition to the open configuration causes said payload to be positioned on an inner surface of the nucleic acid origami device.

10. The nucleic acid origami device of claim 1, wherein:
- (i) in the nucleic acid origami device having the structure A or B, the plurality of staple strands are selected such that the nucleic acid origami device comprises a first domain and a second domain, wherein the first domain comprises said aptamer domain of (a) capable of binding to a binding partner; said oligonucleotide of (b) capable of binding a DNA binding protein; or said oligonucleotide of (c), attached to a nano-antenna; and the second domain comprises said latch domain of structure A or said first or second latch domain of structure B,
wherein a first end of the first domain is attached to a first end of the second domain by at least one single-stranded nucleic acid hinge and the second end of the first domain is attached to the second end of the second domain by the hybridization or binding of each one of said aptamer domains or oligonucleotides to said latch domains, respectively; or
- (ii) in the nucleic acid origami device having the structure C or D, the plurality of staple strands are selected such that the nucleic acid origami device comprises a first domain and a second domain, wherein each one of said first and second domains comprises one of said latch domains linked to a first or a second oligonucleotide, wherein the first oligonucleotide is capable of hybridizing to the second oligonucleotide, the intrinsic oligonucleotide or an external oligonucleotide,
wherein a first end of the first domain is attached to a first end of the second domain by at least one single-stranded nucleic acid hinge and the second end of the first domain is not attached to the second end of the second domain.

11. The nucleic acid origami device of claim 10, wherein
- (i) the plurality of staple strands in the nucleic acid origami device having the structure A or B are selected such that the second end of the first domain becomes unattached to the second end of the second domain if said aptamer domain is contacted by and binds to its respective binding partner and/or if said nano-antenna receives an electromagnetic field and undergoes inductive coupling and subsequent heating;
- (ii) the plurality of staple strands in the nucleic acid origami device having the structure C are selected such that the second end of the first domain becomes attached to the second end of the second domain if each one of said latch domains is hybridized to a different one of said external oligonucleotides; or (iii) the plurality of staple strands in the nucleic acid origami device having the structure D are selected such that the second end of the first domain becomes attached to the second end of the second domain if the latch domains are hybridized to each other.

12. The nucleic acid origami device of claim 1, wherein said binding partner is an antigen selected from the group consisting of a tumor associated antigen; a cell-membrane receptor; a secreted or membrane bound growth factor; a hormone; a cytokine; a ligand; a chemokine; a bacterial, viral or parasitic antigen; a lipid; an oligonucleotide; a sugar, an enzyme or a DNA binding protein.

13. The nucleic acid origami device of claim 1, comprising a scaffold strand and a plurality of staple strands, having the structure A or D, wherein in Structure A:

(i) one of the staple strands comprises either (a) an aptamer domain capable of binding to a glucokinase having a first configuration but incapable of binding to the glucokinase having a second configuration; or (b) an oligonucleotide comprising a nucleotide sequence of a glucose responsive regulatory element capable of binding a glucose response factor having a first configuration but incapable of binding to the glucose response factor having a second configuration;

(ii) another of the staple strands comprises a latch domain linked to the glucokinase, and the aptamer of (a) is capable of binding to the glucokinase having the first configuration but incapable of binding to the glucokinase having the second configuration such that the latch domain is displaced from the aptamer of (a) when the binding partner transitions from the first to the second configuration; or another of the staple strands comprises a latch domain linked to the glucose response factor and the oligonucleotide of (b) is capable of binding to the glucose response factor, having the first configuration but incapable of binding to the glucose response factor having the second configuration such that the latch domain is displaced from the oligonucleotide of (b) when the glucose response factor transitions from the first to the second configuration;

(iii) the aptamer domain of (a) or the oligonucleotide of (b), and the latch domain, when bound to one another, hold the device in a closed configuration; and the device transitions to an open configuration when said aptamer domain of (a) or oligonucleotide of (b), and the latch domain, are not hybridized or bound to one another; and (iv) a further staple strand comprises a handle domain bound to insulin, optionally via a linker, wherein said nucleic acid origami device is either alkylated, acylated or hydroxylated, or interacts with a compound capable of non-covalently binding to the major- or minor-groove of a double stranded nucleic acid, and therefore is resistant to nucleases, and/or said nucleic acid origami device lacks TLR9 recognition elements or the TLR9recognition elements of said nucleic acid origami device are masked or modified and therefore said nucleic acid origami device is non-immunogenic; wherein in Structure D:

(i) one of the staple strands comprises an intrinsic oligonucleotide capable of hybridizing with an external soluble oligonucleotide and an oligonucleotide linked to a latch domain;

(ii) two of the staple strands each comprises a latch domain linked to a first or a second oligonucleotide, wherein the first oligonucleotide is capable of hybridizing to the second oligonucleotide and to the intrinsic oligonucleotide;

(iii) each one of the first and second oligonucleotide is hybridized to one intrinsic oligonucleotide and is selected such that the intrinsic oligonucleotide is capable of hybridizing to the external soluble oligonucleotide such that the external soluble oligonucleotide displaces the intrinsic oligonucleotide and the first and second oligonucleotide hybridize to each other;

(iv) said nucleic acid origami device is in an open configuration when each one of the first and second oligonucleotide is hybridized to said intrinsic oligonucleotide; and the device transitions to a closed configuration when each one of the first and second oligonucleotide is not hybridized to said intrinsic oligonucleotide and is instead hybridized to each other; and (v) a further staple strand comprises a handle domain bound to a drug, optionally via a linker, wherein said nucleic acid origami device is either alkylated, acylated or hydroxylated, or interacts with a compound capable of non-covalently binding to the major- or minor-groove of a double stranded nucleic acid, and therefore is resistant to nucleases, and/or said nucleic acid origami device lacks TLR9 recognition elements or the TLR9 recognition elements of said nucleic acid origami device are masked or modified and therefore said nucleic acid origami device is non-immunogenic.

14. A multimodal nucleic acid origami device comprising at least two inter-connected nucleic acid origami devices each independently according to claim 1.

15. A pharmaceutical composition comprising a nucleic acid origami device of claim 1 and a pharmaceutically acceptable carrier.

16. The nucleic acid origami device of claim 3, wherein said nucleic acid origami device is methylated at CpG dinucleotides.

17. The nucleic acid origami device of claim 6, wherein said small molecule is selected from the group consisting of a cyclooxygenase protein capable of binding paracetamol, a sodium channel subunit capable of binding tetrodotoxin and an anti-digoixin antibody capable of binding digoxin.

18. The nucleic acid origami device of claim 9, wherein the handle domain is bound to a payload selected from the group consisting of an oligonucleotide and a liposome.

19. The nucleic acid origami device of claim 15, wherein said enzyme is a glucokinase and said aptamer domain of (a) is capable of binding to the glucokinase having the first configuration but is incapable of binding to the glucokinase having the second configuration; or the DNA binding protein is a glucose response factor and said oligonucleotide of (b) is a glucose responsive regulatory element capable of binding to the glucose response factor having the first configuration but incapable of binding to the glucose response factor having the second configuration.

* * * * *